United States Patent
Gupta et al.

(10) Patent No.: US 11,358,978 B2
(45) Date of Patent: Jun. 14, 2022

(54) PROCESS FOR PREPARING SUPRAMOLECULAR PLATINUM-BASED COMPOUNDS

(71) Applicant: AKAMARA THERAPEUTICS, INC., Philadelphia, PA (US)

(72) Inventors: Nimish Gupta, Delhi (IN); Arindam Sarkar, Delhi (IN); Heeralal Bassi, Delhi (IN); Pradip Dutta, Delhi (IN)

(73) Assignee: Akamara Therapeutics, Inc., Philadelphia, PA (US)

( * ) Notice: Subject to any disclaimer, the term of this patent is extended or adjusted under 35 U.S.C. 154(b) by 715 days.

(21) Appl. No.: 15/575,090

(22) PCT Filed: May 18, 2016

(86) PCT No.: PCT/IB2016/052901
§ 371 (c)(1),
(2) Date: Nov. 17, 2017

(87) PCT Pub. No.: WO2016/185402
PCT Pub. Date: Nov. 24, 2016

(65) Prior Publication Data
US 2020/0016113 A1    Jan. 16, 2020

(30) Foreign Application Priority Data
May 19, 2015    (IN) ........................... 1418/DEL/2015

(51) Int. Cl.
| | | |
|---|---|---|
| C07F 15/00 | (2006.01) | |
| A61K 47/54 | (2017.01) | |
| A61K 47/69 | (2017.01) | |
| A61K 9/51 | (2006.01) | |
| A61K 31/28 | (2006.01) | |

(52) U.S. Cl.
CPC ........ *C07F 15/0013* (2013.01); *A61K 9/5115* (2013.01); *A61K 9/5161* (2013.01); *A61K 9/5192* (2013.01); *A61K 31/28* (2013.01); *A61K 47/543* (2017.08); *A61K 47/6929* (2017.08)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,737,323 A | 4/1988 | Martin et al. |
| 4,897,355 A | 1/1990 | Eppstein et al. |
| 5,171,678 A | 12/1992 | Behr et al. |
| 5,885,613 A | 3/1999 | Holland et al. |

FOREIGN PATENT DOCUMENTS

| | | |
|---|---|---|
| JP | 7247250 A | 9/1995 |
| JP | 2002-528458 A | 5/2000 |
| RU | 2074861 C1 | 3/1997 |
| WO | 90/08157 A1 | 7/1990 |
| WO | 96/14057 A1 | 5/1996 |
| WO | 96/37194 A1 | 11/1996 |
| WO | 2006/110804 A2 | 10/2006 |
| WO | 2010/091192 | 8/2010 |
| WO | 2014/199352 | 12/2014 |
| WO | 2014/201376 | 12/2014 |

OTHER PUBLICATIONS

Tromp et al., The β-glucuronyl-based prodrug strategy allows for its application on β-glucuronyl-platmum conjugates. Bioorganic & medicinal chemistry letters. Aug. 16, 2004;14(16):4273-4276.
Szoka et al, Procedure for preparation of liposomes with large internal aqueous space and high capture by reverse-phase evaporation. Proceedings of the national academy of sciences. Sep. 1, 1978;75(9):4194-4198.
Sengupta et al: "Cholesterol-tethered platinum II-based supramolecular nanoparticle increases antitumor efficacy and reduces nephrotoxicity", Proceedings of the national academy of sciences, vol. 109, No. 28, Jun. 25, 2012 (Jun. 25, 2012), pp. 11294-11299.
Saouma CT. Synthetic strategies to improve the cytotoxicity of platinum-based cancer therapeutics (Doctoral dissertation, Massachusetts Institute of Technology), 2005, 78 pgs.
Santos et al., Study of the pilot production process of long-circulating and pH-sensitive liposomes containing cisplatin. Journal of liposome research. Mar. 1, 2011;21(1):60-69.
Roberts, Water soluble DACH, Pt(II) complexes: Problems of purification; Stability of complexes with nitrogen-containing ligands., Inorg. Chim. Acta, 1988, 153(2), 123-127.
Rieger, Pharmaceutical Dosage Forms, Marcel Dekker, Inc., NY, NY, 1988, p. 285.
Rademaker-Lakhai et al, A Phase I and pharmacological study of the platinum polymer AP5280 given as an intravenous infusion once every 3 weeks in patients with solid tumors. Clinical Cancer Research. May 15, 2004;10(10):3386-3395.
Paschke et al.. Cholic acid-carboplatin compounds (CarboChAPt) as models for specific drug delivery: synthesis of novel carboplatin analogous derivatives and comparison of the cytotoxic properties with corresponding cisplatin compounds. Journal of inorganic biochemistry. Apr. 1, 2003;94(4):335-342.
Olson et al., Preparation of liposomes of defined size distribution by extrusion through polycarbonate membranes. Biochimica et Biophysica Acta (BBA)-Biomembranes. Oct. 19, 1979;557(1):9-23.
Mukhopadhyay et al, Conjugated platinum (IV)—peptide complexes for targeting angiogenic tumor vasculature. Bioconjugate chemistry. Sep. 11, 2007;19(1):39-49.
Mayhew et al, Characterization of liposomes prepared using a microemulsifier. Biochimica et Biophysica Acta (BBA)-Biomembranes. Aug. 22, 1984;775(2):169-174.
Lin, Improved targeting of platinum chemotherapeutics: the antitumour activity of the HPMA copolymer platinum agent AP5280 in murine tumour models. European Journal of Cancer. Jan. 1, 2004;40(2):291-297.

(Continued)

*Primary Examiner* — Joseph R Kosack
(74) *Attorney, Agent, or Firm* — BakerHostetler

(57) ABSTRACT

The present invention is in relation to the fields of nanotechnology and cancer therapeutics. In particular, the present disclosure relates to improved methods for preparing lipid-conjugated platinum compounds with high purity and good yields. The present disclosure also relates to nanoparticles comprising lipid-conjugated platinum compounds with high drug loading efficiency for use in chemotherapy, and to methods for producing said nanoparticles.

23 Claims, 26 Drawing Sheets

(56) References Cited

OTHER PUBLICATIONS

Leite et al., Encapsulation of cisplatin in long-circulating and pH-sensitive liposomes improves its antitumor effect and reduces acute toxicity. International journal of nanomedicine. 2012;7:5259-5269.

Kim et al., Preparation of multivesicular liposomes. Biochimica et Biophysica Acta (BBA)-Biomembranes. Mar. 9, 1983;728(3):339-348.

Karanth et al, pH-Sensitive liposomes-principle and application in cancer therapy, Journal of pharmacy and pharmacology 59.4 (2007): 469-483.

Haxton, Polymeric drug delivery of platinum-based anticancer agents. Journal of pharmaceutical sciences. Jul. 1, 2009;98(7):2299-2316.

Gonzalez, Platinum complexes for multi-parametric assays using microarray systems. Journal of inorganic biochemistry. Jan. 1, 2012;106(1):43-45.

Fukunaga et al, Liposome entrapment enhances the hypocalcemic action of parenterally administered calcitonin. Endocrinology. Aug. 1, 1984;115(2):757-761.

Felgner et al, Lipofection: a highly efficient, lipid-mediated DNA-transfection procedure. Proceedings of the National Academy of Science. Nov. 1, 1987;84(21):7413-7417.

Dhar et al., Targeted delivery of cisplatin to prostate cancer cells by aptamer functionalized Pt(IV) prodrug-PLGA-PEG nanoparticles, Proceedings of the national academy of sciences, Nov. 11, 2008, 105(45), 17356-17361.

De Carvalho et al, Antitumor effectiveness and toxicity of cisplatin-loaded long-circulating and pH-sensitive liposomes against Ehrlich ascitic tumor. Experimental Biology and Medicine Aug. 2012;237(8):973-984.

Bangham, Diffusion of univalent ions across the lamellae of swollen phospholipids. Journal of molecular biology. Aug. 1, 1965;13(1):238-IN27.

MeOH:DCM(20:80)

MeOH:DCM(10:90)

MeOH:DCM(20:80)  MeOH:DCM(10:90)

PROCESS FOR PREPARING SUPRAMOLECULAR PLATINUM-BASED COMPOUNDS

RELATED APPLICATIONS

This application is the National Stage Application of International Patent Application No. PCT/IB2016/052901, filed May 18, 2016, which claims benefit under one or more of 35 U.S.C. § 119(a)-119(d) of Indian Patent Application No. 1418/DEL/2015, filed May 19, 2015, the content of both applications are incorporated herein by reference in their entirety.

TECHNICAL FIELD

The present invention is in relation to the fields of nanotechnology and cancer therapeutics. In particular, the present disclosure relates to the synthesis of lipid-conjugated platinum compounds, and further relates to methods for preparing lipid-conjugated platinum compounds with high purity and good yields. The present disclosure also relates to nanoparticles comprising lipid-conjugated platinum compounds with high drug loading efficiency for use in chemotherapy, and to methods for producing said nanoparticles.

BACKGROUND

Platinum-based chemotherapeutic agents are used as first line of therapy in over 70% of all cancers. Cisplatin undergoes rapid formation of cis-$[Pt(NH_3)_2Cl(OH_2)]^+$ and cis-$[Pt(NH_3)_2(OH_2)]^{2+}$ resulting in nephrotoxicity. Further, aquation of both carboplatin and oxaliplatin are significantly slower, resulting in decreased potency. In the recent past, considerable progress has been made wherein, Dhar et al. (PNAS, 2008, 105, 17356) generated a platinum (IV) complex (c,t,c-$[Pt(NH_3)_2(O_2CCH_2CH_2CH_2CH_2CH_3)_2Cl_2]$ that is hydrophobic enough for encapsulation into PLGA-b-PEG nanoparticles. However, the pro-drug in this case has to be intracellularly processed into cisplatin. Furthermore, alternative strategies based on conjugation of platinum to polymers (eg a polyamidoamine dendrimer-platinum complex) resulted in a 200-550 fold reduction in cytotoxicity than free cisplatin. This was a result of strong bonds formed between the polymer and platinum (J. Pharm. Sci., 2009, 98, 2299). Another example is AP5280, a N-(2-hydroxypropyl) methacrylamide copolymer-bound platinum that is less potent than carboplatin. Here, the platinum is held by an aminomalonic acid chelating agent coupled to the COOH-terminal glycine of a tetrapeptide spacer (Clin. Can. Res., 2004, 10, 3386; Eur. J. Can., 2004, 40, 291). Further, WO 2010/091192 A2 (Sengupta et al.) discloses biocompatible conjugated polymer nanoparticles including a copolymer backbone, a plurality of sidechains covalently linked to said backbone, and a plurality of platinum compounds dissociably linked to said backbone.

Lipid-based oxaliplatin, cisplatin and carboplatin molecular frameworks have been an attractive area of research for anticancer drug development due to their ability to form nanoparticles and provide enhanced permeation and retention (EPR) effect. However, reports on lipid-conjugated platinum drugs are extremely rare. This is due to the problems associated with low yielding synthetic methods and difficulty purifying these compounds. Achieving good yields in lipid-to-platinum coupling (complexation) reactions remains challenging due to the large solubility difference between the lipid-based ligands and the platinum precursors. Lipid-containing ligands are more soluble in organic solvents, whereas the platinum precursors are more soluble in water. To improve solubility of the reactants, mixtures of organic and aqueous solvents have been used in most of the reported complexation reactions, particularly if the lipid is water-insoluble (e.g., cholesterol, see Table 1, Ref. 1). Even so, this solubility issue results in incomplete reactions. Thus, purification of the desired platinum complex from unreacted starting materials becomes difficult. These reactions also suffer from drawbacks such as complicated multi-step procedures (see Table 1, Ref. 3), higher reaction temperatures (see Table 1, Ref. 2, 3), and complicated workup procedures (see Table 1, Ref. 2), etc.

TABLE 1

Comparative studies of the literature-reported procedures for the synthesis of lipid-conjugated platinum complexes

| Ref. No. | Reference | Procedure for aquation of Pt | Temperature (° C.) | Procedure for complexation |
|---|---|---|---|---|
| 1 | PNAS, 2012, 109, 11294 | $PtCl_2(NH_3)_2$ + $AgNO_3$ (1:1) [solvent = water] | RT | DMF-water mixture |
| 2 | Journal of Inorganic Biochemistry 2012, 106, 43-45 | $PtCl_2(en)$ + KI = $PtI_2(en)$ [solvent = water] (en = ethylene diamine) | 65 | Water |
| 3 | Journal of Inorganic Biochemistry 94 (2003) 335-342 | Multistep | 70 | Reflux in water ethanol mixture |

Further purification of Pt-based compounds to obtain a product that meets U.S. Food & Drug Administration (FDA) requirements is known to be a complex and challenging process. Purification of the final lipid-conjugated platinum active pharmaceutical ingredients (API) has been problematic because they are difficult to crystallize due to their large size and amphiphilic nature. Pt(IV)-peptide conjugates have been purified by reverse phase high-performance liquid chromatography (HPLC); however, final purity by HPLC analytical methods has not been reported (Mukhopadhyay, S. et al., Bioconjug. Chem., 19, 39-49 (2008)). For a few other cases, it has been reported that the Pt(IV) complexes decompose on the column and could not be purified (Saouma, C. T., Synthetic strategies to improve the cytotoxicity of platinum-based cancer therapeutics. 1-78 (2005) at <http://dspace.mit.edu/handle/1721.1/36279#files-area>). Similarly another method reported for purification of Pt(II) complexes does not demonstrate the final purity by HPLC (Tromp, R. et al., Bioorg. Med. Chem. Lett., 14, 4273-6 (2004)). Problems with purification of Pt(II) compounds, especially those containing nitrogen-containing ligands, has been reported (Roberts, J. D., Inorg. Chim. Acta, 153, 123-127 (1988)). In this case, the post-purification product was biologically less active.

The present invention aims to overcome the drawbacks of the prior art and provide an improved synthetic procedure to obtain reasonably good purity of the crude lipid-conjugated platinum compounds (APIs) with high yields. Certain aspects of the present invention also provide a robust preparative HPLC method for purification of lipid-conjugated platinum compounds. Certain aspects of the present invention provide for stable, potent and safer nano-platinates in cancer chemotherapy.

SUMMARY

The present disclosure provides synthetic strategies for the preparation of lipid-conjugated platinum compounds. One aspect of the present invention provides a method for preparing a lipid-conjugated platinum compound, wherein the method comprises: reacting a water-soluble salt of a lipid with a water-soluble platinum compound in a substantially aqueous solution to obtain the lipid-conjugated platinum compound as a precipitate. Another aspect provides a method for further purifying the lipid-conjugated platinum compound using HPLC. Another aspect provides a method for preparing nanoparticles comprising the disclosed lipid-conjugated platinum compounds.

BRIEF DESCRIPTION OF THE DRAWINGS

In order that the invention may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure.

DETAILED DESCRIPTION

Figure 1:
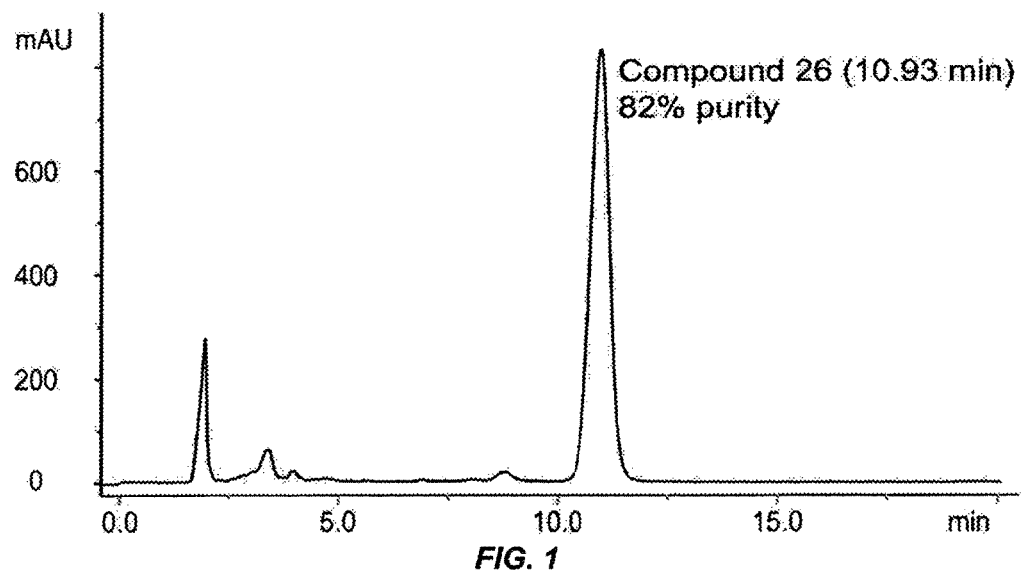
FIG. 1 shows an HPLC profile of compound 26 (RT: 10.93 min) on C18 column before water/acetone wash. The purity of the compound is 82%. Mobile phase: 100% methanol. Detection: 210 nm, UV.

The present invention provides a process for a simple and cost-effective procedure for the lipid functionalization of platinum compounds, which forms a reasonably pure lipid-conjugated platinum compound in good yield from the reaction mixture itself. Once formed, immediate precipitation of the lipid-conjugated platinum compound thermodynamically drives the reaction toward the direction of complexation, thus leading to higher yields. Other advantages of certain exemplary embodiments of the disclosed process include mild reaction conditions, such that the reaction can be completed at room temperature and one atmosphere of pressure within a few hours. In certain exemplary embodiments, water is used as the only solvent. In certain exemplary embodiments, the lipid-conjugated platinum compound is precipitated from the reaction mixture to give crude product in ≥50%, ≥60%, ≥70%, ≥80% or ≥90% yield, or in the range of 70% to 90% yield. In certain exemplary embodiments, the lipid-conjugated platinum compound has a crude purity of ≥50%, ≥60%, ≥70%, ≥80% or ≥90%. In certain exemplary embodiments, the crude products are subsequently purified using semi-preparative or preparative high-performance liquid chromatography (HPLC) to >99.5% purity, meeting United States Food and Drug Administration (FDA) requirements.

Certain exemplary embodiments of the present invention provide a method for preparing a lipid-conjugated platinum compound, wherein the method comprises: reacting a water-soluble salt of a lipid with a water-soluble platinum compound in a substantially aqueous solution to obtain the lipid-conjugated platinum compound as a precipitate. Certain exemplary embodiments further comprise the step of filtering or centrifuging the reaction mixture to separate the precipitate from the substantially aqueous solution, and optionally washing the precipitate with water. Without being bound by theory, the disclosed methods provide for a product that precipitates out because it is insoluble in aqueous solution while the reactants remain in solution, thus allowing for ease of product purification by simply filtering or centrifuging the reaction mixture.

Certain exemplary embodiments further comprise the step of purifying the lipid-conjugated platinum compound using HPLC. HPLC is used to further improve the purity of the lipid-conjugated platinum compound to >99.5% in accordance with FDA guidelines. HPLC methods were first optimized on an analytical column and then transferred to larger scale on a preparative column to obtain gram quantities of ≥99.5% pure lipid-conjugated platinum compound. The HPLC methods disclosed herein (see Examples below) are very robust and indifferent to starting purity of the lipid-conjugated platinum compound. Compounds with starting purity from 20-90% have been purified successfully using the disclosed methods. The HPLC purification process is also high yielding (e.g., ≥50%, ≥60%, ≥70%, ≥80% or ≥90% yield for different lipid-functionalized platinum compounds). Lipid-conjugated platinum compounds are difficult to purify by recrystallization, but the HPLC purification methods disclosed herein advantageously overcome that difficulty.

In certain exemplary embodiments, the HPLC purification method uses a preparative reverse-phase column. In certain exemplary embodiments, the column comprises an $NH_2$ stationary phase, a Phenyl stationary phase, or a C18 stationary phase. In certain exemplary embodiments, the column comprises $NH_2$ or Phenyl as the stationary phase, and the lipid-conjugated platinum compound is eluted using a gradient method. In certain exemplary embodiments, the gradient method comprises eluting with a mobile phase comprising a mixture of water and methanol, wherein elution begins with the mixture having a higher percentage of water and linearly progresses over time to the mixture having a higher percentage of methanol. In certain exemplary embodiments, the column comprises C18 as the stationary phase, and the lipid-conjugated platinum compound is eluted using an isocratic method. In certain exemplary embodiments, the isocratic method comprises eluting with a mobile phase comprising 98% methanol and 2% water.

The term "substantially aqueous solution" is defined as a solution comprising mostly water, e.g. at least 90% water, at least 95% water, at least 98% water, at least 99% water, and 100% water. At least 99% water may include any amount of water 99% or greater and up to 100%, e.g. 99.3% water, 99.5% water, 99.8% water, 99.9% water, and 100% water.

In certain exemplary embodiments, the water-soluble salt of a lipid and the water-soluble platinum compound are reacted at room temperature. The term "room temperature" is used in the conventional sense, in that no external heating or cooling element is applied to the reaction. Room temperature can include temperatures in the range of, e.g. 10° C. to 40° C., 20° C. to 30° C., 22° C. to 28° C., and about 25° C. In certain exemplary embodiments, the water-soluble salt of a lipid and the water-soluble platinum compound are reacted at one atmosphere of pressure. One atmosphere of pressure may include a value within a range of pressures, e.g. 790-650 mmHg, 780-690 mmHg, 770-730 mmHg, and about 760 mmHg.

In certain exemplary embodiments, the water-soluble salt of a lipid is selected from the group consisting of: a lithium salt, a sodium salt, a potassium salt, a rubidium salt, a cesium salt, a magnesium salt, a calcium salt, a strontium salt, a barium salt, and any combination thereof. In some embodiments, the water-soluble salt of a lipid may be provided by reacting a lipid with a base selected from the group consisting of: LiOH, NaOH, KOH, RbOH, CsOH, Mg(OH)2, Ca(OH)2, Sr(OH)2, Ba(OH)2, and any combination thereof.

In some embodiments, the water-soluble salt of a lipid can be an acid salt. The acid for producing the acid salt can be an inorganic or organic acid. Exemplary organic acids for producing the water-soluble salt of the lipid include, but are not limited to, trifluoroacetic acid (TFA), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-methylenebis(3-hydroxy-2-ene-1-carboxylic acid), glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Exemplary organic acids for producing the water-soluble salt of the lipid include, but are not limited to, hydrochloric acid, hydrobromic acid, perchloric acid, nitric acid, thiocyanic acid, sulfuric acid, phosphoric acid, and the like.

In some embodiments of the various aspects disclosed herein, the platinum moiety is a platinum (II) or platinum (IV) compound. In some embodiments, the platinum (II) compound is selected from the group comprising of DACH-platinum, cisplatin, oxaliplatin, carboplatin, paraplatin, sartraplatin, and various combinations thereof. In some embodiments, the platinum containing compound is Pt(II) compound, Pt(IV) compound or halide containing platinum compound. In a preferred embodiment, the platinum compounds are oxaliplatin.

The term "lipid" is used in the conventional sense and includes compounds of varying chain length, from as short as about 2 carbon atoms to as long as about 28 carbon atoms. Additionally, the compounds may be saturated or unsaturated and in the form of straight- or branched-chains or in the form of unfused or fused ring structures. Exemplary lipids include, but are not limited to, fats, waxes, sterols, steroids, bile acids, fat-soluble vitamins (such as A, D, E, and K), monoglycerides, diglycerides, phospholipids, glycolipids, sulpholipids, aminolipids, chromolipids (lipochromes), glycerophospholipids, sphingolipids, prenollipids, saccharolipids, polyketides, and fatty acids.

Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis 25 13-docosenoic acid; cluytyl alcohol; coenzyme Q10 (CoQ10); Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Laurie acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; γ-Linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, γ-linolenic acid; and any combinations thereof.

In certain exemplary embodiments, the lipid is cholesterol or derivatives thereof. In some embodiments, the lipid is α-tocopherol.

In certain exemplary embodiments, the water-soluble salt of a lipid further comprises a linker covalently attached to the lipid. As used herein, the term "linker" means an organic moiety that can connect two parts of a compound. Linkers typically comprise a direct bond to an atom such as oxygen or sulfur, a unit such as $NR^1$, $C(O)$, $C(O)NH$, $C(O)O$, $NHC(O)O$, $OC(O)O$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkenylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaiyl, alkylheteroaryl, alkenylheteroaryl, alkynylhereroaryl, where one or more methylenes can be interrupted or terminated by O, S, S(O), $SO_2$, $NR^1$, $C(O)$, $C(O)NH$, $C(O)O$, $NHC(O)O$, $OC(O)O$, $SO_2NH$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In certain exemplary embodiments, the linker covalently attached to the lipid is represented by Formula I:

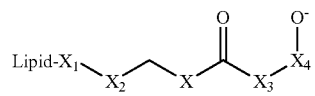

Wherein:

X is NH;

$X_1$ is selected from the group consisting of COOH, $CONH_2$, $O-(CH_2)_n-OH$, $NH_2$ and OH;

$X_2$ is $(CH_2)_n$ or CO;

$X_3$ is selected from the group consisting of $(CH_2)_n$, $CH_2-NH$ and $C_4H_8$;

$X_4$ is CO or $-CH-CH_3$;

and wherein n=0-2.

In certain exemplary embodiments, the linker covalently attached to the lipid is represented by Formula II:

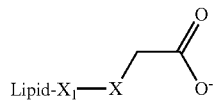

Wherein,

X is NH or N—CH$_2$COO$^-$;

X$_1$ is selected from the group consisting of —(CH$_2$)$_n$OH, —(CH$_2$)$_n$NHCOOH, —(CH$_2$)$_n$CONH(CH$_2$)$_n$OH, (CH$_2$)$_n$O (CH$_2$)$_n$OH, (CH$_2$)$_n$C=O, —(CH$_2$)$_n$NHCO(CH$_2$)$_n$OH and (CH$_2$)$_n$—COOH; wherein n=0-2.

In certain exemplary embodiments, the linker covalently attached to the lipid is represented by Formula III:

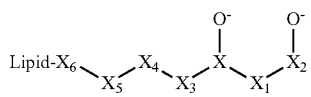

Wherein,

X is selected from the group consisting of S$^+$, C, S$^+$=O, N$^+$H and P=O;

X$_1$ is selected from the group consisting of —CH, —CH$_2$ and —CH$_2$O;

X$_2$ is C=O;

X$_3$ is CH, CH$_2$ or O; and

X$_4$, X$_5$, X$_6$ is —CH$_2$O or O.

In certain exemplary embodiments, the linker covalently attached to the lipid is represented by Formula IV:

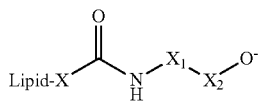

Wherein,

X is CH$_2$OH;

X$_1$ is (CH$_2$)$_n$, wherein n=0-2; and

X$_2$ is C=O.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH) O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O) NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

Linkers according to the present invention include moieties comprising two or more carbon molecules such as, for example, ethylenediamine, ethyleneglycol, glycine, beta-alanine and polyethylene glycol (PEG) of molecular weight about 44 to about 200 kD. Further, it is to be understood from the present disclosure that the platinum moiety and/or the lipid may be modified to comprise functional groups for linking to the linker molecule.

In some embodiments of the various aspects disclosed herein, the linker is —X—$CH_2$—$X_2$—$X_1$—, wherein X is NH; $X_1$ is C(O)O, C(O)NH, O($CH_2$)—O, NH, or O; $X_2$ is $(CH_2)_n$ or C(O); and n is 0, 1, 2, 3, 4, or 5.

In some other embodiments, the linker is —$(CH_2)_nO$—, —$(CH_2)_nNHC(O)O$—, —$(CH_2)_nOC(O)NH$—, —$(CH_2)_nC(O)NH(CH_2)_mO$—, —$(CH_2)_nO(CH_2)_mO$—, —$(CH_2)_nO(O)$—, —$(CH_2)_nNHC(O)(CH_2)_mO$—, or —$(CH_2)_nC(O)O$—; and n and m are independently 0, 1, 2, 3, 4, or 5.

In still some other embodiments, the linker is —$X_3$-$X_4X_5$-$X_6$—, wherein $X_3$ is CH, $CH_2$, or O; and $X_4$, $X_5$ and $X_6$ are independently same or different and are —$CH_2O$— or O.

In yet some other embodiments, the linker is —$CH_2O$—.

In some embodiments, the linker is selected from the group consisting of a bond, —O—, $NHCH_2CH_2NHC(O)$—, —$NHCH_2CH_2NHC(O)O$—, —$NHCH_2CH_2$—, —$NHCH_2CH_2O$—, —$NHCH_2C(O)$—, —$NHCH_2C(O)O$—, —$NHCH_2C(O)OCH_2CH_2CH_2$—, —$NHCH_2C(O)OCH_2CH_2CH_2O$—, —$NHCH_2C(O)NH$—, —$CH_2CH_2$—, —$CH_2CH_2O$—, —$CH_2CH_2NHC(O)$—, —$CH_2CH_2NHC(O)O$—, —$CH_2CH_2O$—, —$CH_2C(O)NHCH_2CH_2$—, —$CH_2C(O)NHCH_2CH_2O$—, —$CH_2CH_2OCH_2CH_2$—, —$CH_2CH_2OCH_2CH_2O$—, —$CH_2C(O)$—, —$CH_2C(O)O$—, —$CH_2CH_2CH_2$—, —$CH_2CH_2CH_2O$—, =CH—CH=$CH_2$—, =CH—CH=$CHCH_2O$—, —CH=$CHCH_2$—, —CH=$CHCH_2O$—, —$OCH_2CH_2O$—, —$CH_2$—, —$CH_2O$—, —$NHC(O)CH_2$—, —$NHC(O)CH_2O$—, —$C(O)CH_2$—, —$C(O)CH_2O$—, —$OC(O)CH_2$—, —$OC(O)CH_2O$—, —$C(O)CH_2CH_2C(O)NHCH_2CH_2$—, —$OC(O)CH_2CH_2C(O)NHCH_2CH_2$—, —$C(O)CH_2CH_2C(O)NHCH_2CH_2O$—, —$OC(O)CH_2CH_2C(O)NHCH_2CH_2O$—, —$C(O)CH_2CH_2C(O)NHCH_2CH_2NHC(O)$—, —$OC(O)CH_2CH_2C(O)NHCH_2CH_2NHC(O)$—, —$OC(O)CH_2CH_2C(O)NHCH_2CH_2NHC(O)$—, —$OC(O)CH_2CH_2C(O)NHCH_2CH_2NHC(O)O$—, and any combinations thereof.

In certain exemplary embodiments, the water-soluble salt of a lipid may be provided by reacting a lipid or a linker covalently attached to a lipid with a base selected from the group consisting of: LiOH, NaOH, KOH, RbOH, CsOH, $Mg(OH)_2$, $Ca(OH)_2$, $Sr(OH)_2$, $Ba(OH)_2$, and any combination thereof. In some embodiments, a lipid or a linker covalently attached to a lipid is reacted with LiH to provide the water-soluble salt of the lipid.

In certain exemplary embodiments, the water-soluble platinum compound is represented by Formula V:

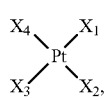

Wherein, $X_1$, $X_2$, $X_3$ and $X_4$ are independently selected from the group consisting of halide, alkyl, amino, alkylamino, dialkylamino, hydroxyl, $H_2O$, alkoxy, thiol, thioalkyl, O-acyl, and any combinations thereof.

$X_1$ and $X_2$ may be monodentate or bidentate ligands. In some embodiments, $X_1$ and $X_2$ are amino, e.g. $NH_3$ or diaminocyclohexyl (DACH). In some embodiments, $X_3$ and $X_4$ are each $H_2O$. In certain exemplary embodiments, the water-soluble platinum compound is provided by reacting a platinum compound of Formula V, wherein $X_1$ and $X_2$ comprise a bidentate amino ligand and $X_3$ and $X_4$ each comprise a halide, with $AgNO_3$ and $H_2O$. In some embodiments of this step, $X_1$ and $X_2$ are DACH and $X_3$ and $X_4$ are each Cl.

The disclosed methods of the present invention may be used to synthesize various lipid-conjugated platinum compounds. In certain exemplary embodiments, the lipid-conjugated platinum compound is represented by Formula V:

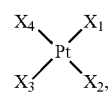

Wherein, $X_1$, $X_2$, $X_3$ and $X_4$ are independently selected from the group consisting of halide, alkyl, amino, alkylamino, dialkylamino, hydroxyl, alkoxy, thiol, thioalkyl, O-acyl, and any combinations thereof.

In some embodiments, the lipid-conjugated platinum compounds disclosed herein are represented by Formula (VI):

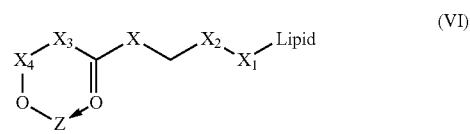

Wherein,

X is NH;

$X_1$ is selected from a group comprising COOH, $CONH_2$, O—$(CH_2)_n$—OH, $NH_2$ and OH;

$X_2$ is $(CH_2)_n$ or CO;

$X_3$ is selected from a group comprising $(CH_2)_n$, $CH_2$—NH and $C_4H_8$;

$X_4$ is CO or —CH—$CH_3$;

Z is a platinum compound according to Formula V, wherein the platinum forms a part of Formula VI ring; and n is 0, 1, or 2.

In some other embodiments, the lipid-conjugated platinum compounds disclosed herein are represented by Formula (VII):

Wherein,

X is NH or N—$CH_2COO$;

$X_1$ is selected from a group comprising —$(CH_2)_nOH$, —$(CH_2)_nNHCOOH$, —$(CH_2)_nCONH(CH_2)_nOH$, $(CH_2)_nO(CH_2)_nOH$, $(CH_2)_nC$=O, —$(CH_2)_nNHCO(CH_2)_nOH$ and $(CH_2)_n$ COOH;

Z is a platinum compound according to Formula V, wherein the platinum forms a part of Formula VII ring; and n is 0, 1, or 2.

In some embodiments, the lipid-conjugated platinum compounds disclosed herein are represented by Formula (VIII):

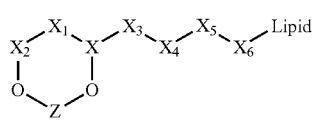

(VIII)

Wherein,

X is selected from a group comprising $S^+$, C, $S^+$=O, $N^+H$ and P=O;

$X_1$ is selected from a group comprising —CH, —$CH_2$ and —$CH_2O$;

$X_2$ is C=O;

$X_3$ is selected from CH, $CH_2$ or O;

$X_4$, $X_5$, $X_6$ is selected from —$CH_2O$ or O

Z is a platinum compound according to Formula V, wherein the platinum forms a part of Formula VIII ring.

In some embodiments, the lipid-conjugated platinum compounds disclosed herein are represented by Formula (IX):

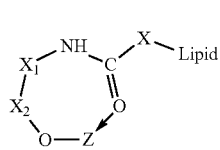

(IX)

Wherein,

X is $CH_2OH$;

$X_1$ is $(CH_2)_n$;

$X_2$ is C=O;

Z is a platinum compound according to Formula V, wherein the platinum forms a part of Formula IX ring; and n is 0, 1, or 2.

Exemplary compounds of Formula (VI) include, but are not limited to, the following compounds: All Formula (VI) compounds contain a nitrate ($NO_3^-$) counter ion which is not shown in the figures.

Compound 1

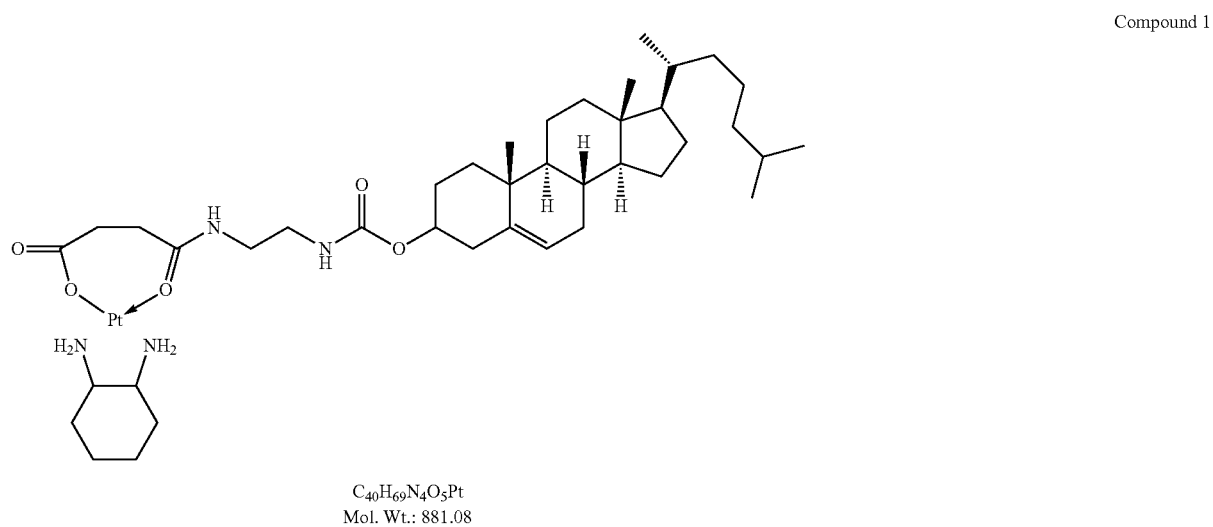

$C_{40}H_{69}N_4O_5Pt$
Mol. Wt.: 881.08

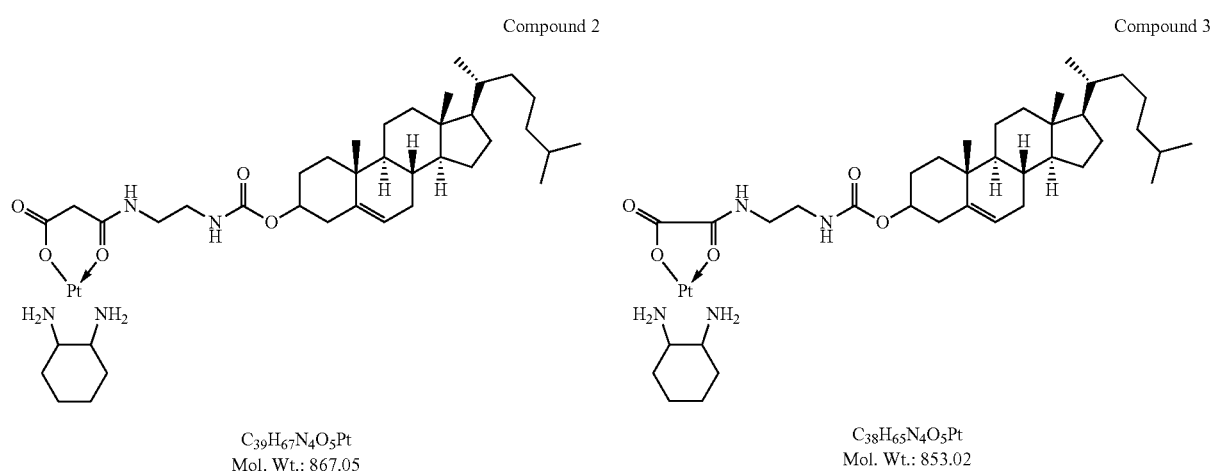

Compound 2

$C_{39}H_{67}N_4O_5Pt$
Mol. Wt.: 867.05

Compound 3

$C_{38}H_{65}N_4O_5Pt$
Mol. Wt.: 853.02

Compound 4
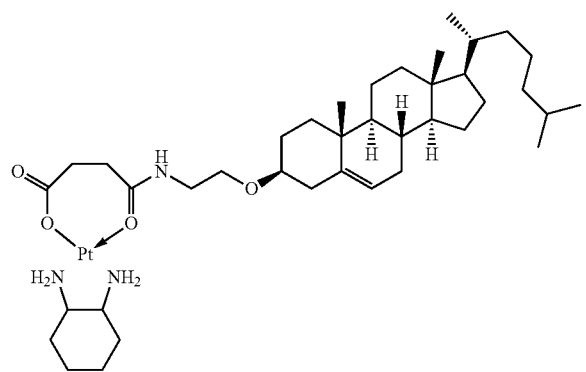
C<sub>39</sub>H<sub>68</sub>N<sub>3</sub>O<sub>4</sub>Pt
Mol. Wt.: 838.05
Compound 5
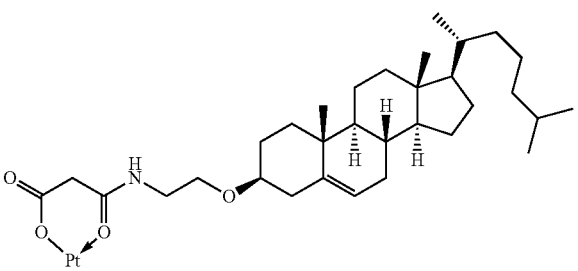
C<sub>38</sub>H<sub>66</sub>N<sub>3</sub>O<sub>4</sub>Pt
Mol. Wt.: 824.03
Compound 6
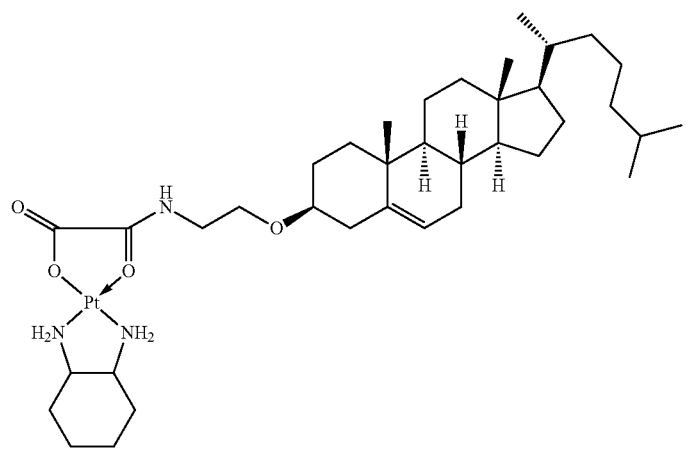
C<sub>37</sub>H<sub>64</sub>N<sub>3</sub>O<sub>4</sub>Pt
Mol. Wt.: 810.00
Compound 7
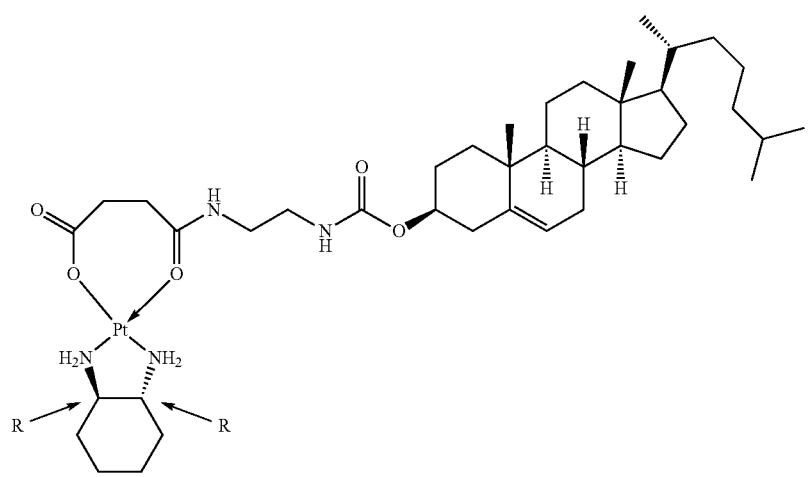
C<sub>40</sub>H<sub>69</sub>N<sub>4</sub>O<sub>5</sub>Pt
Mol. Wt.: 881.08

-continued
Compound 8
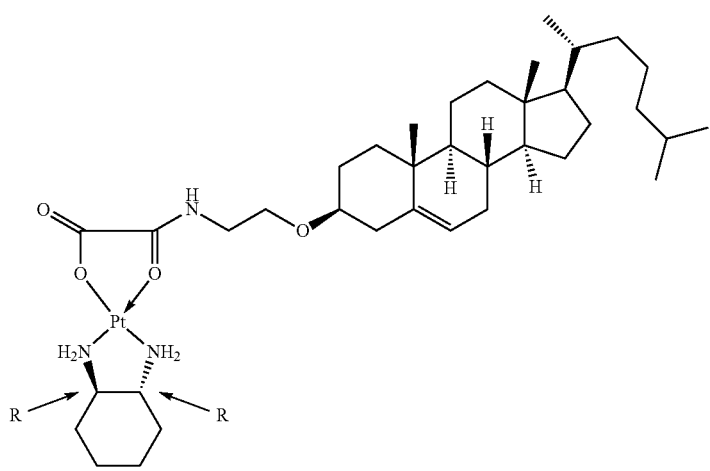
C₃₇H₆₄N₃O₄Pt
Mol. Wt.: 810.00
Compound 9
Compound 10
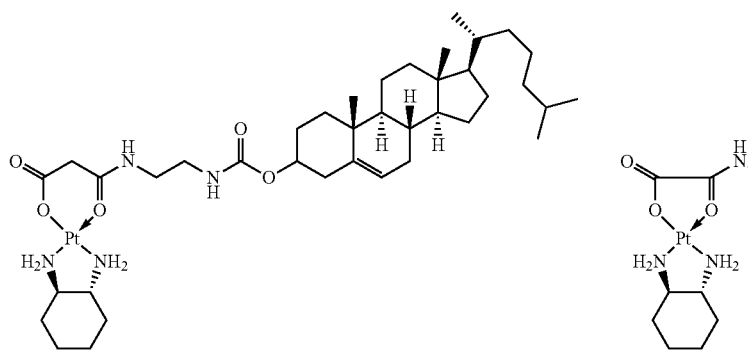
C₃₉H₆₇N₄O₅Pt
Mol. Wt.: 867.05
C₃₉H₆₅N₄O₅Pt
Mol. Wt.: 853.02
Compound 11
Compound 12
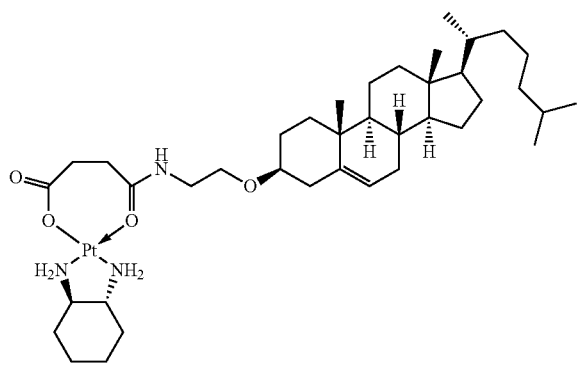
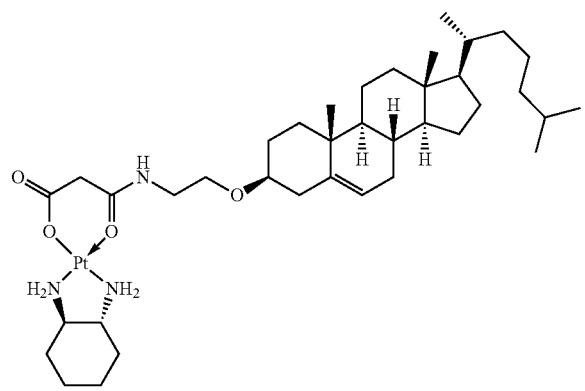
C₃₉H₆₈N₃O₄Pt
Mol. Wt.: 838.05
C₃₈H₆₆N₃O₄Pt
Mol. Wt.: 824.03

-continued
Compound 13
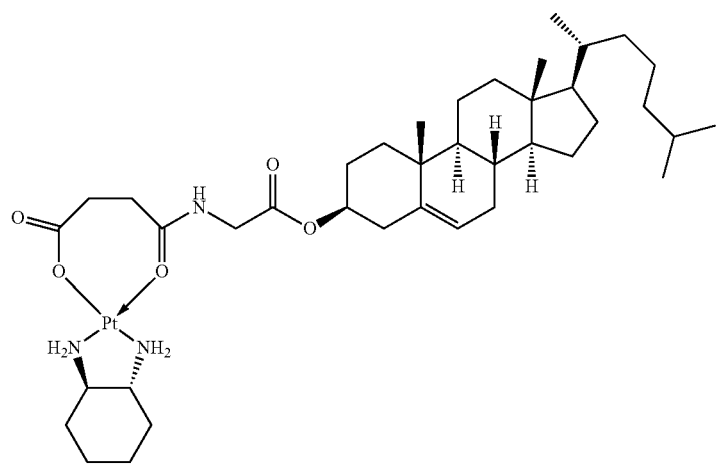
C₃₉H₆₆N₃O₅Pt
Mol. Wt.: 852.04
Compound 14
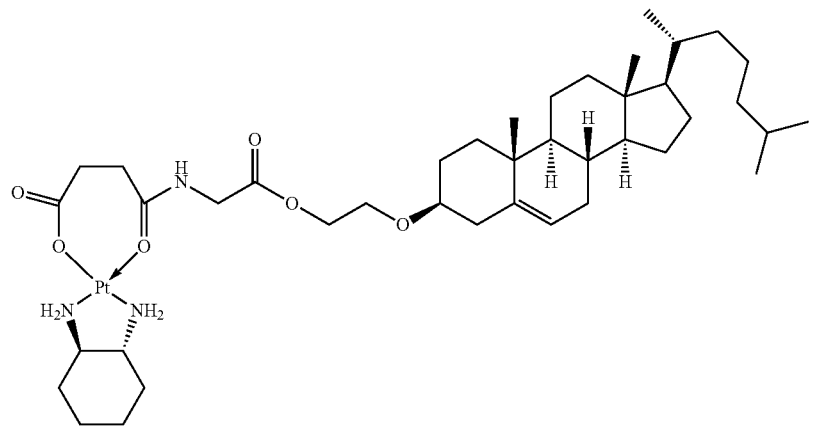
C₄₁H₇₀N₃O₆Pt
Mol. Wt.: 896.09
Compound 15
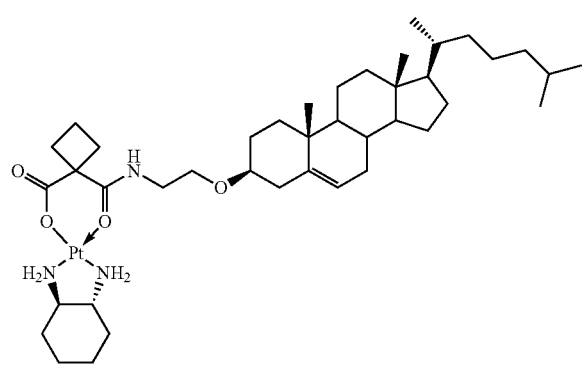
C₄₁H₆₈N₃O₄Pt
Mol. Wt.: 862.07
Compound 16
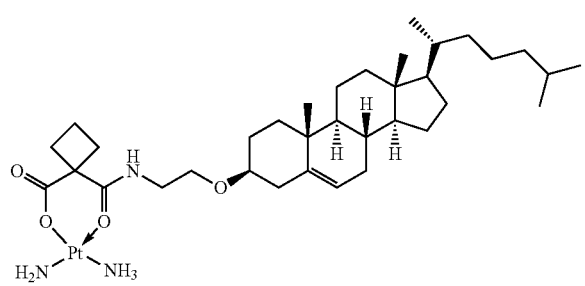
C₃₅H₆₂N₃O₄Pt
Mol. Wt.: 783.96

-continued
Compound 17
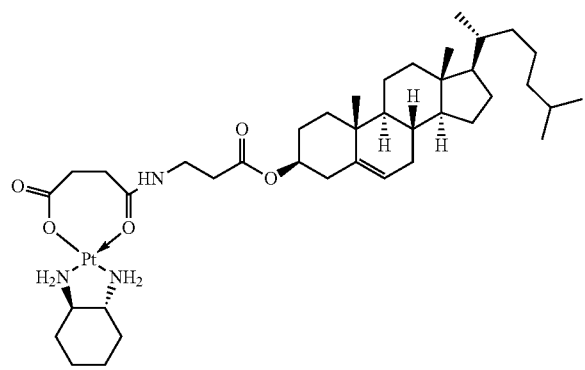
C$_{40}$H$_{68}$N$_3$O$_5$Pt
Mol. Wt.: 866.06
Compound 18
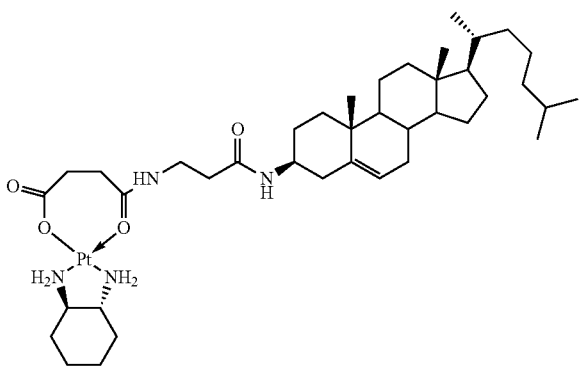
C$_{40}$H$_{69}$N$_4$O$_4$Pt
Mol. Wt.: 865.08
Compound 19
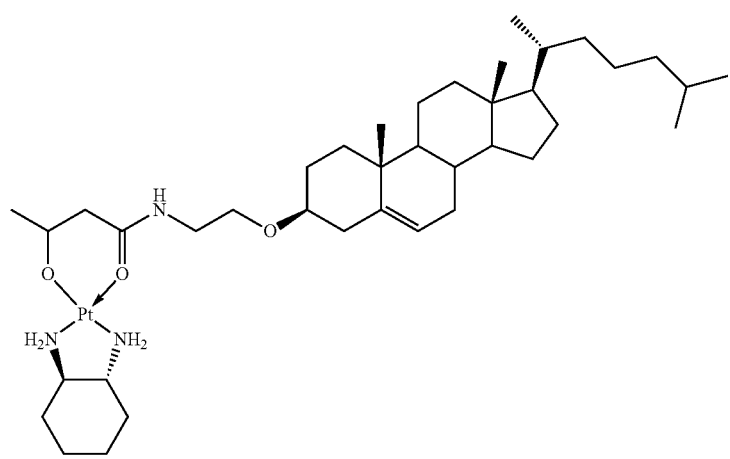
C$_{39}$H$_{68}$N$_3$O$_3$Pt
Mol. Wt.: 82205
Compound 20
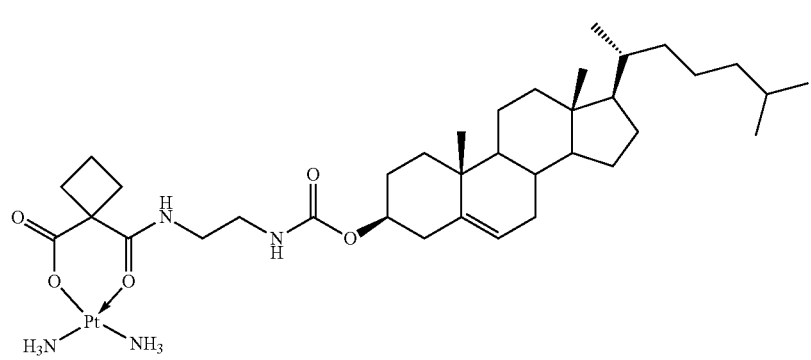
C$_{36}$H$_{63}$N$_4$O$_5$Pt
Mol. Wt.: 826.99

-continued
Compound 21
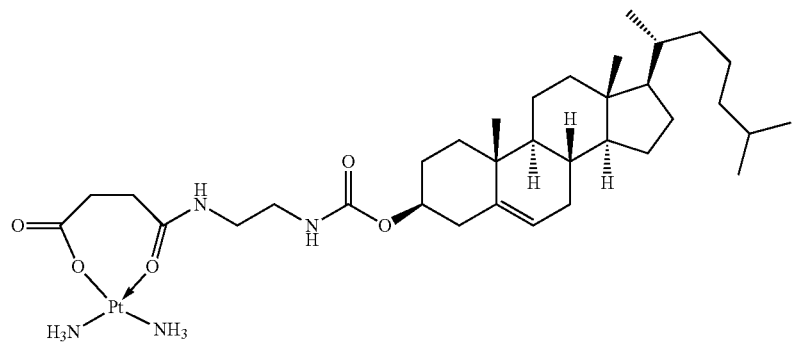
C$_{34}$H$_{61}$N$_4$O$_5$Pt
Mol. Wt.: 800.43
Exemplary compounds of Formula (VII) include, but are not limited to, the following compounds:
Compound 25
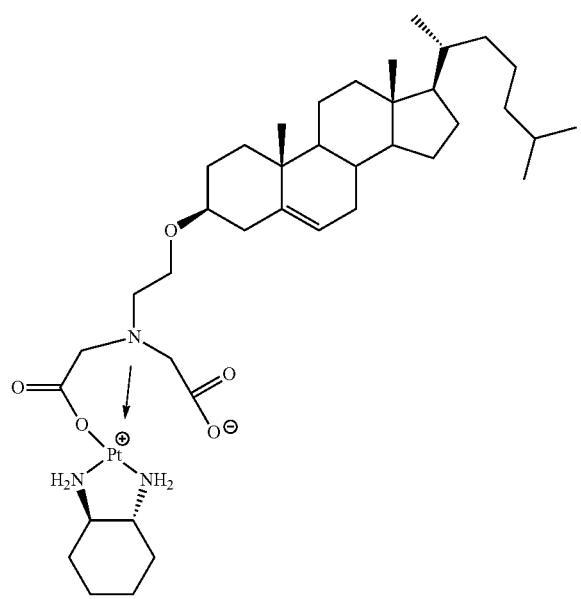
Compound 26
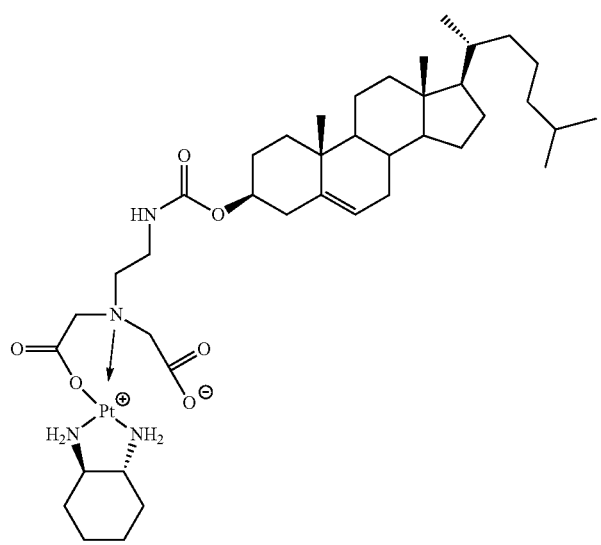
Compound 27
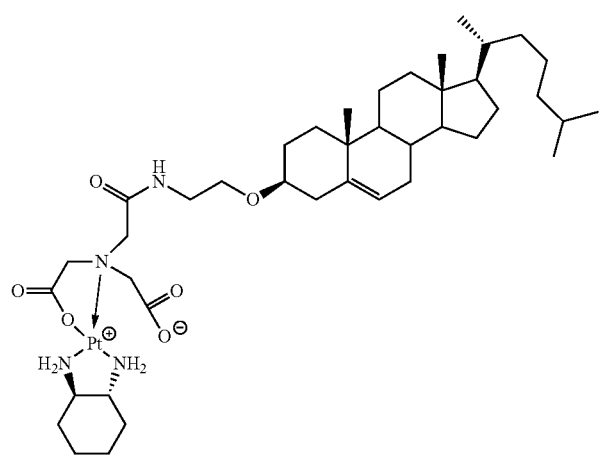
Compound 28
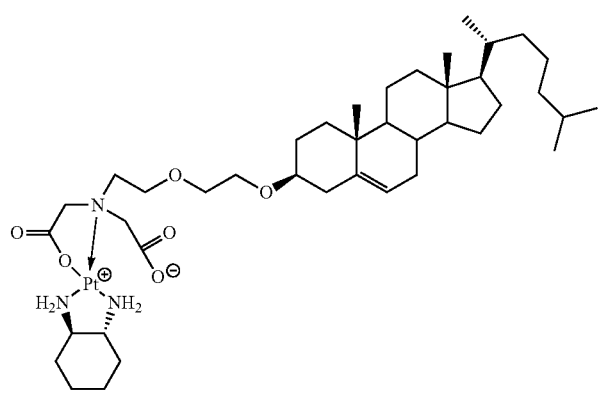

-continued
Compound 29
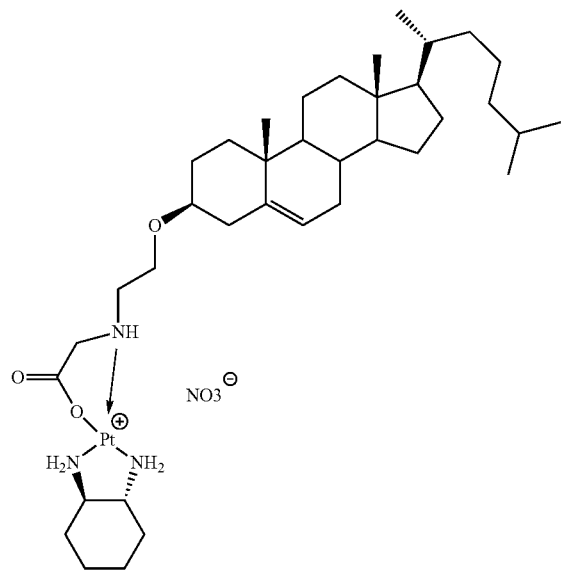
Compound 38
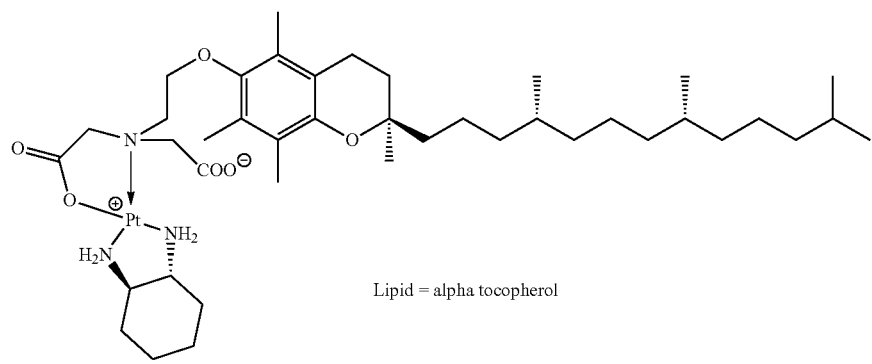
Lipid = alpha tocopherol
Compound 39
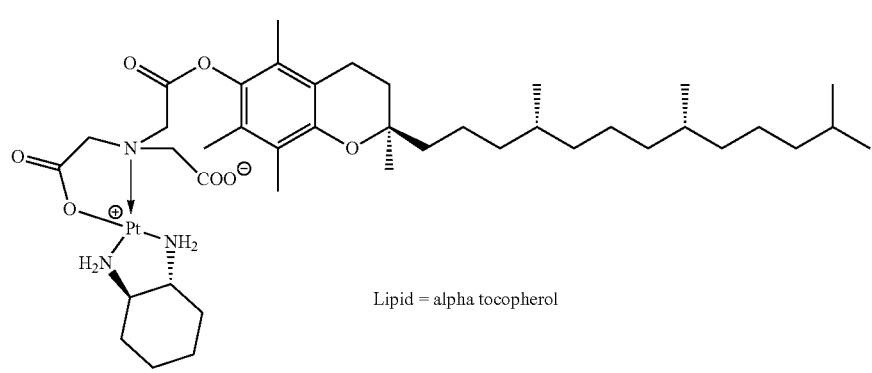
Lipid = alpha tocopherol Compound 40
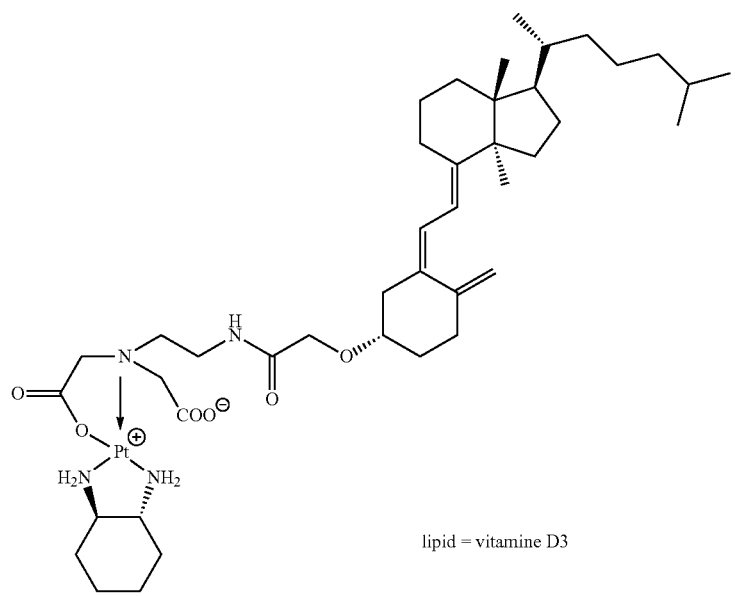
lipid = vitamine D3
Compound 41
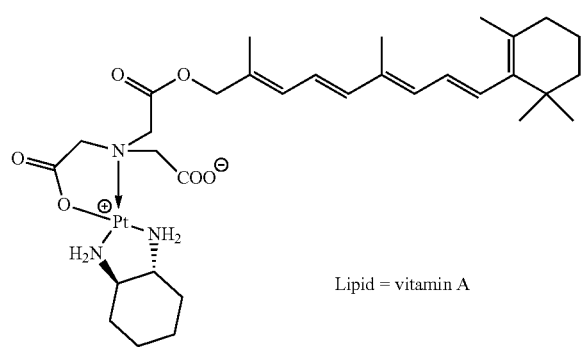
Lipid = vitamin A
Compound 42
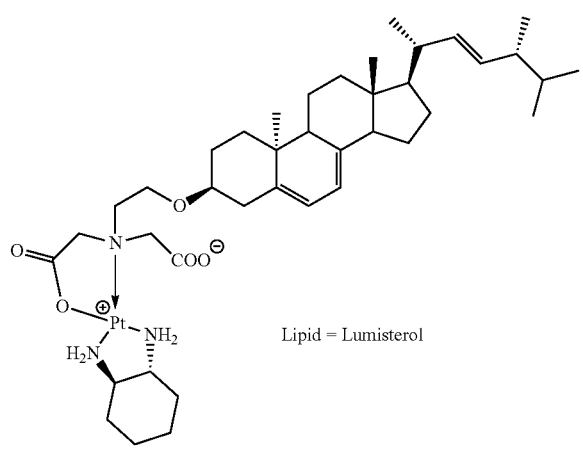
Lipid = Lumisterol
Exemplary compounds of Formula (VIII) include, but are not limited to, the following compounds:
Compound 66
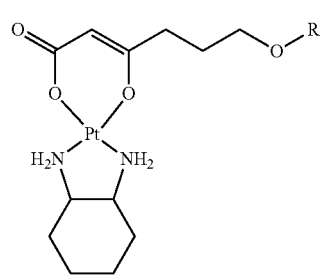
R = Lipid, Aromatic
-continued
Compound 67
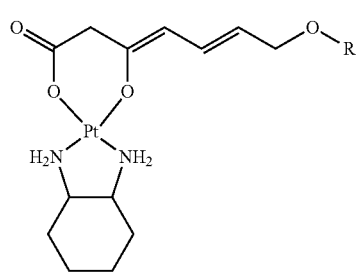
R = Lipid, Aromatic Compound 68
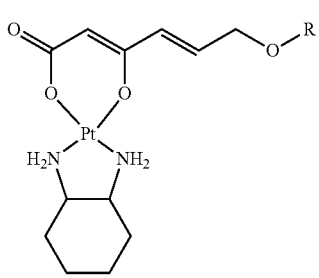
R = Lipid, Aromatic
Compound 69
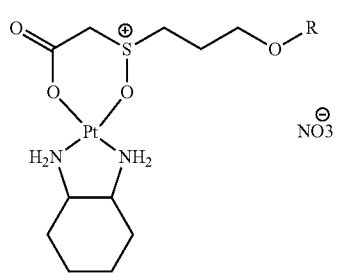
R = Lipid, Aromatic
Compound 70
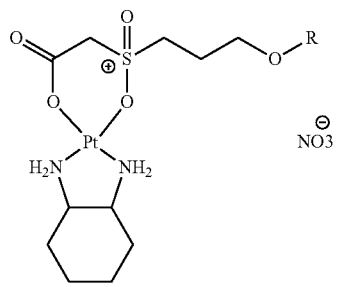
R = Lipid, Aromatic
Compound 72
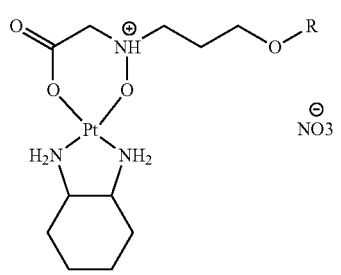
R = Lipid, Aromatic
Compound 71
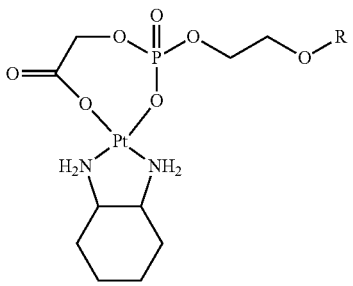
R = Lipid, Aromatic
Exemplary compounds of Formula (IX) include, but are not limited to, the following compounds.
Compound 22
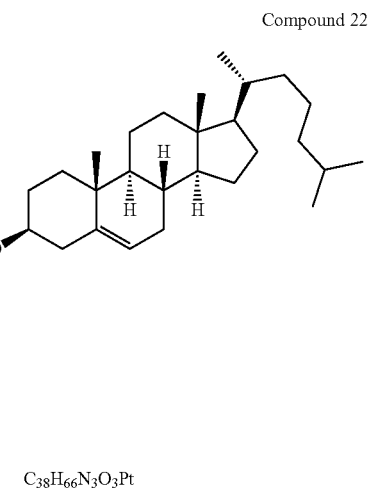
$C_{38}H_{66}N_3O_3Pt$
Mol. Wt.: 810.00
The disclosure also provides the following compounds:
Compound 23
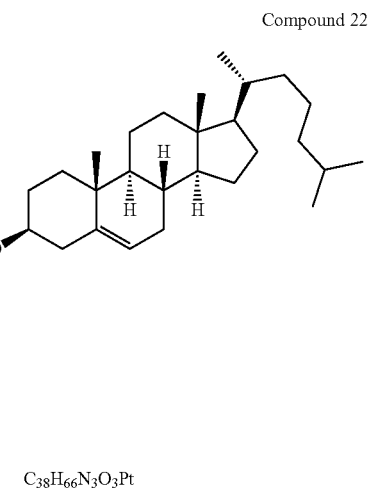
$C_{39}H_{65}N_3O_6Pt$
MW = 867.03

-continued

Compound 30

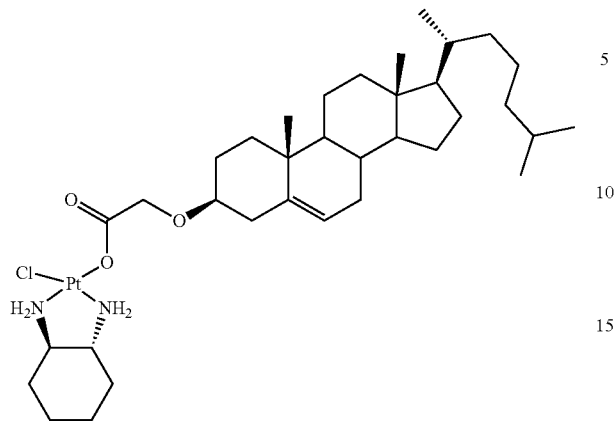

In some embodiments of the various aspects disclosed herein, the platinum compound of Formula (V) is selected from a group comprising Compounds 43-65 and 73-85 and Compound 95. In a preferred embodiment, the Pt compound is DACH-Pt.

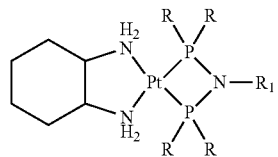

Compound 43

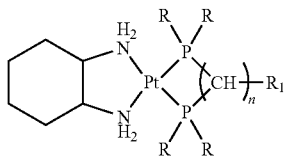

n = 1, 2
Compound 44 (n = 1 and
Compound 45 (n = 2)

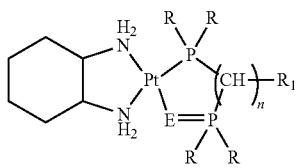

R = Alkyl or Aryl
Compounds 46 (E = O),
47 (E = S) and 48 (E = Se)

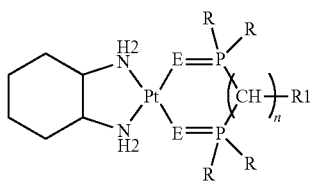

R = Alkyl or Aryl
Compounds 49 (E = O),
50 (E = S) and 51 (E = Se)

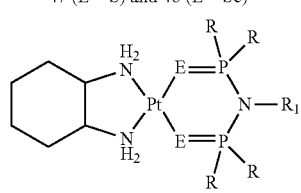

R = Alkyl or Aryl
Compounds 52 (E = O),
53 (E = S) and 54 (E = Se)

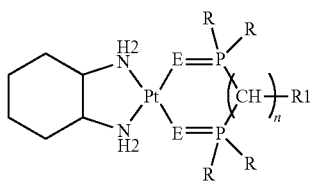

R = Alkyl or Aryl
Compounds 55 (E = O),
56 (E = S) and 57 (E = Se)

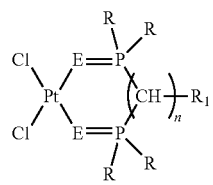

R = Alkyl or Aryl; n = 1, 2
Compounds 58 (E = O),
59 (E = S) and 60 (E = Se)

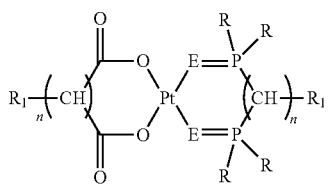

R = Alkyl or Aryl; n = 0, 1
Compounds 61 (E = S) and
62 (E = Se)

Compound 63
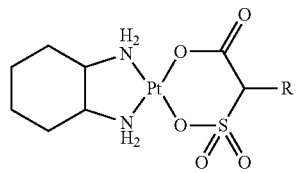
Compound 64
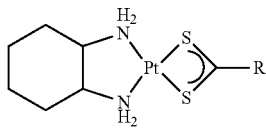
Compound 65
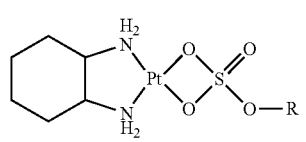
Compound 73
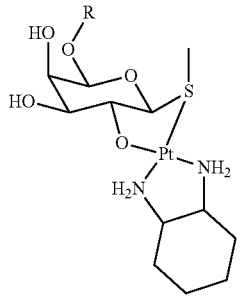
R = Aryl, Alkyl, Lipid
Compound 74
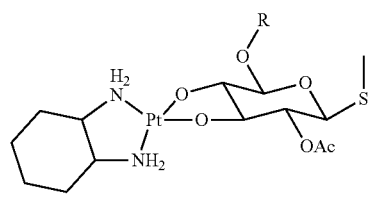
R = Aryl, Alkyl, Lipid
Compound 75
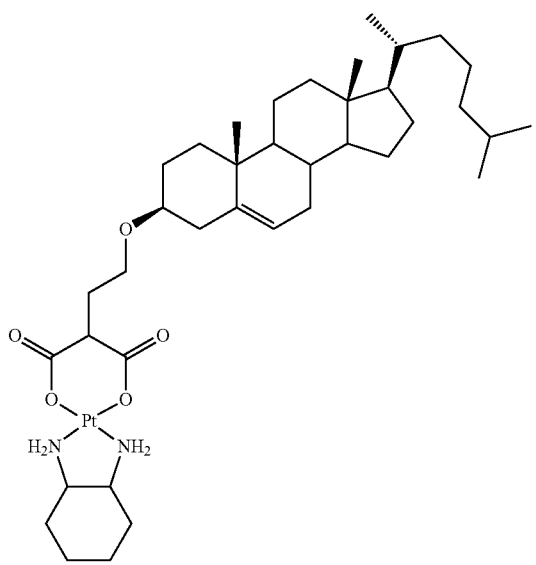

-continued

Compound 76

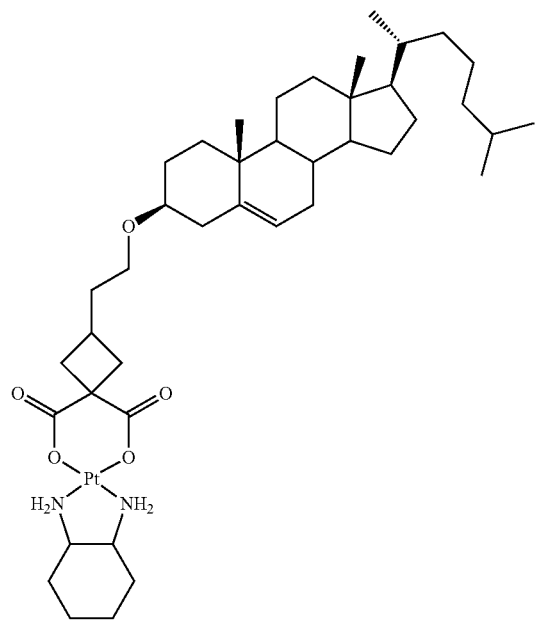

Compound 77

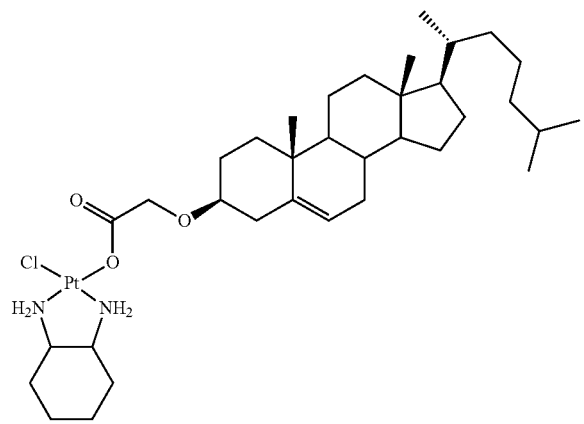

Compound 79

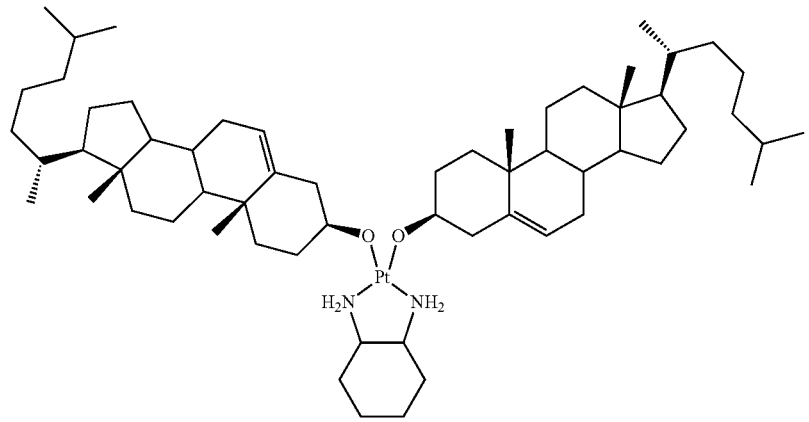

In the above compounds, R₁ is a -linker-lipid and n is 1 unless defined otherwise.

Some exemplary embodiments of the present invention provide nanoparticles comprising the disclosed lipid-conjugated platinum compounds, and methods for producing said nanoparticles. The disclosed methods advantageously provide high encapsulation efficiency, high drug loading, uniform size, and good stability. In certain exemplary embodiments, methods are disclosed for producing stable lyophilized pegylated amphiphilic supra-molecular self-assembly of a Compound 25 formulation with high drug loading efficiency for use in chemotherapy. To clarify the characteristics of the present invention, some examples of its implementation with different mol % of active and inactive pharmaceutical ingredients are described below in the Examples. It should be understood that although the Examples describe formulations comprising Compound 25, any lipid-conjugated platinum compound described in the present disclosure may be substituted to produce nanoparticles of the present invention.

In certain exemplary embodiments, a method is disclosed for preparing a nanoparticle, wherein the method comprises: mixing a platinum compound comprising a platinum moiety and a lipid connected to said platinum moiety with a co-lipid in the presence of solvent to obtain the nanoparticle. In certain exemplary embodiments, the platinum compound is prepared according to the methods disclosed herein. In certain exemplary embodiments, the solvent is selected from the group comprising chloroform, methanol, dichloromethane, ethanol, and any combinations thereof. In certain exemplary embodiments, the co-lipid is selected from the group consisting of Soy-phosphatidyl choline (fully hydrogenated), 1,2-Distearoyl-sn-Glycero-3-Phosphoethalonamine-N-[Methoxy(Polyethylene glycol)-2000], dioleoyl phosphatidylcholine (DOPC), DSPE-PEG-OMe, dioleoyl phosphatidylethanolamine (DOPE), dipalmitoyl phosphatidyl choline (DPPC) and any combination thereof. In certain exemplary embodiments, the method for preparing a nanoparticle further comprises the steps of drying, incubation and optional addition of a stabilizer. In certain exemplary embodiments, the stabilizer is selected from the group consisting of DSPE-PEG-OMe, DSPE-PEG-NH₂, PEG, inorganic salt, carbohydrate, and any combinations thereof. In certain exemplary embodiments, the inorganic salt is selected from the group consisting of ammonium chloride, potassium chloride, sodium chloride, disodium hydrogen phosphate, sodium dihydrogen phosphate, and any combination thereof. In certain exemplary embodiments, the carbohydrate is selected from the group consisting of glucose, dextrose, sucrose, trehalose, mannitol, lactose and any combinations thereof. In certain exemplary embodiments, the co-lipids comprise soy-phosphatidyl choline (hydrogenated) (HSPC) and 1,2-Distearoyl-sn-Glycero-3-Phosphoethalonamine-N-[Methoxy(Polyethylene glycol)-2000] (DSPE-$PEG_{2000}$). In certain exemplary embodiments, the mol % ratio of the platinum compound (Pt) and the co-lipids (Pt:HSPC:DSPE-$PEG_{2000}$) is about 30-32:55-60:4-5, or from about 30:55:4 to about 32:60:5. In certain exemplary embodiments, the mol % ratio of the platinum compound (Pt) and the co-lipids (Pt:HSPC:DSPE-PEG2000) is about 4-5:30-32:55-60, or from about 4:30:55 to about 5:32:60. In certain exemplary embodiments, the co-lipids comprise soy-phosphatidyl choline (hydrogenated) (HSPC), cholesterol (CHOL) and 1,2-Distearoyl-sn-Glycero-3-Phosphoethalonamine-N-[Methoxy(Polyethylene glycol)-2000](DSPE-$PEG_{2000}$) In certain exemplary embodiments, the mol % ratio of the platinum compound (Pt) and the co-lipids (Pt:HSPC:CHOL:DSPE-$PEG_{2000}$) is about 20-35:60-70:3-15:1-5, or from about 20:60:3:1 to about 35:70:15:5. In certain exemplary embodiments, the mol % ratio of the platinum compound (Pt) and the co-lipids (Pt:HSPC:CHOL:DSPE-$PEG_{2000}$) is about 1-5:20-35:60-70:3-15, or from about 1:20:60:3:1 to about 5:35:70:15. In some embodiments, mol % ratio HSPC:CHOL:Pt:DSPE-PEG2000 is 55:3:38:4 mol %.

In certain exemplary embodiments, the co-lipid is DOPE. The mol % of the platinum compound (Pt) and the DOPE lipid can range from 20-35:30-50. In certain embodiments, the mol % of the platinum compound (Pt) and the DOPE lipid can range from 22.5-27.5:35-50. In embodiments, the mol % of the platinum compound (Pt) and the DOPE lipid is about 40:25. In certain exemplary embodiments, the co-lipids comprise DOPE, soy-phosphatidyl choline (hydrogenated) (HSPC), cholesterol (CHOL) and 1,2-Distearoyl-sn-Glycero-3-Phosphoethalonamine-N-[Methoxy(Polyethylene glycol)-2000] (DSPE-$PEG_{2000}$). In some embodiments, the co-lipids are DOPE and HSPC and mol % ratio of DOPE and HSPC is about 30-50:25-35 or from about 30:25 to about 50:35. In some embodiments, the co-lipids are DOPE and cholesterol and mol % ratio of DOPE to cholesterol is about 30-50:1-5 or from about 30:1 to about 50:5. In some embodiments, the co-lipids are DOPE and DSPE-$PEG_{2000}$ and mol % ratio of DOPE to DSPE-$PEG_{2000}$ is about 30-50:1-10 from about 30:1 to 50:4. In certain exemplary embodiments, the mol % ratio of the platinum compound (Pt) and the co-lipids (Pt:DOPE:HSPC:CHOL:DSPE-$PEG_{2000}$) is about 20-40:30-50:25-35:3-15:1-5. In one embodiment, Pt:DOPE:HSPC:CHOL:DSPE-$PEG_{2000}$ mol % ratio is about 25:40:28:3:4.

Certain exemplary embodiments relate to the synthesis of a series of platinum based nanoparticles wherein, the diaminocyclohexyl-Pt (DACH-Pt) has a monocarboxylated covalent bond through a carboxylic acid and a co-ordination bond with amide oxygen. Dicarbonyl molecules (dicarboxylic acids) such as succinic acid, malonic acid and oxalic acid are used which eventually form seven, six and five member rings with platinum (II) respectively. The linker between the platinum ring and cholesterol helps in forming linkages selected from a group comprising carbamate linkage (compounds 1, 2, 3), ether linkage (compounds 6, 4, 5) or the likes or any combinations thereof. Therefore, some of the embodiments of the present disclosure relates to compounds represented by the general backbone: lipid-linker-dicarbonyl. These molecules are used to complex platinum compounds such as DACH-Pt, oxaliplatin, cisplatin, platinum containing carbenes or other platinates and platinum compounds, through covalent and/or coordination bonds.

In an embodiment of the present disclosure, several variants of platinum based compounds such as racemates, diastereomers and the likes are also provided (for example, Compounds 1-6).

In an embodiment of the present disclosure, any molecule that has two carbonyl groups may be used. In one embodiment, the dicarbonyl molecule is a dicarboxylic acid, such as, for example, succinic acid, malonic acid or oxalic acid.

The disclosure also provides particles comprising one or more of the platinum based compounds described herein. Generally, the particle disclosed herein can be of any shape or form, e.g., spherical, rod, elliptical, cylindrical, capsule, or disc; and these particles can be part of a network or an aggregate.

In some embodiments, the particle is a microparticle or a nanoparticle. As used herein, the term "microparticle" refers to a particle having a particle size of about 1 μm to about 1000 μm. As used herein, the term "nanoparticle" refers to particle having a particle size of about 0.1 nm to about 1000 nm. Generally, the particles have any size from nm to millimeters. In some embodiments, the particles can have an average diameter ranging from about 5 nm to about 5000 nm. In some embodiments, the particles have an average diameter of from about 50 nm to about 2500 um, from about 100 nm to about 2000 nm, from about 150 nm to about 1700 nm, from about 200 nm to about 1500 nm, or about 260 nm. In some embodiments, the particles have an average diameter of about 30 nm to about 150 nm or about 50 nm to about 250 um. In some embodiments, the particles have an average diameter of about 100 nm to about 1000 nm, from about 200 nm to about 800 nm, from about 200 nm to about 700 nm, or from about 300 nm to about 700 nm.

In some embodiments, the particle has an average size of about 50 to about 1000 nm. In a further embodiment, the nanoparticles of the present invention are in the range of about 50 to about 500 nm. In another embodiment, the nanoparticles of the present invention are in the range of about 50 to about 200 nm. In one embodiment, the particle has a size of about 50 to about 100 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 125, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In addition to the platinum compounds disclosed herein, the particle can comprise co-lipids and/stabilizers. Additional lipids can be included in the particles for a variety of purposes, such as to prevent lipid oxidation, to stabilize the bilayer, to reduce aggregation during formation or to attach ligands onto the particle surface. Any of a number of additional lipids and/or other components can be present, including amphipathic, neutral, cationic, anionic lipids, and programmable fusion lipids. Such lipids and/or components can be used alone or in combination. One or more components of particle can comprise a ligand, e.g., a targeting ligand.

In some embodiments, the particle further comprises a phospholipid. Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, ß,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myristoyl phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and ß-acyloxyacids, can also be used In some embodiments, the phospholipid in the particle is selected from the group consisting of 1,2-Didecanoyl-sn-glycero-3-phosphocholine; 1,2-Dierucoyl-sn-glycero-3-phosphate (Sodium Salt); 1,2-Dierucoyl-sn-glycero-3-phosphocholine; 1,2-Dierucoyl-sn-glycero-3-phosphoethanolamine; 1,2-Dierucoyl-sn-glycero-3 [Phospho-rac-(1-glycerol) (Sodium Salt); 1,2-Dilinole oyl-sn-glycero-3-phosphocholine; 1,2-Dilauroyl-sn-glycero-3-phosphate (Sodium Salt); 1,2-Dilauroyl-sn-glycero-3-phosphocholine; 1,2-Dilauroyl-sn-glycero-3 phosphoethanolamine; 1,2-Dilauroyl-sn-glycero-3[Phospho-rac-(1-glycerol) (Sodium Salt); 1,2-Dilauroyl-sn-glycero-3[Phospho-rac-(1-glycerol) (Ammonium Salt); 1,2-Dilauroyi-sn-glycero-3-phosphoserine (Sodium Salt); 1,2-Dimyristoyl-sn-glycero-3-phosphate (Sodium Salt); 1,2-Dimyristoyl-sn-glycero-3-phosphocholine; 1,2-Dimyristoyl-sn-glycero-3-phosphoethanolamine; 1,2-Dimyristoyl-sn-glycero-3[Phospho-rac-(1-glycerol) (Sodium Salt); 1,2-Dimyristoyl-sn-glycero-3[Phospho-rac-(1-glycerol) (Ammonium Salt); 1,2-Dimyristoyl-sn-glycero-3[Phospho-rac-(1-glycerol) (Sodium/Ammonium Salt); 1,2-Dimyristoyl-sn-glycero-3-phosphoserine (Sodium Salt); 1,2-Dioleoyl-sn-glycero-3-phosphate (Sodium Salt); 1,2-Dioleoyl-sn-glycero-3-phosphocholine; 1,2-Dioleoyl-sn-glycero-3-phosphoethanolamine; 1,2-Dioleoyl-sn-glycero-3 [Phospho-rac-(1-glycerol) (Sodium Salt); 1,2-Dioleoyl-sn-glycero-3-phosphoserine (Sodium Salt); 1,2-Dipalmitoyl-sn-glycero-3-phosphate (Sodium Salt); 1,2-Dipalmitoyl-sn-glycero-3-phosphocholine; 1,2-Dipalmitoyl-sn-glycero-3-phosphoethanolamine; 1,2-Dipalmitbyl-sn-glycero-3 [Phospho-rac-(1-glycerol) (Sodium Salt); 1,2-Dipalmitoyl-sn-glycero-3[Phospho-rac-(1-glycerol) (Ammonium Salt); 1,2-Dipalmitoyl-sn-glycero-3-phosphoserine (Sodium Salt); 1,2-Distearoyl-sn-glycero-3-phosphate (Sodium Salt); 1,2-Distearoyl-sn-glycero-3-phosphocholine; 1,2-Distearoyl-sn-glycero-3-phosphoethanolamine; 1,2-Distearoyl-sn-glycero-3[Phospho-rac-(1-glycerol) (Sodium Salt); 1,2-

Distearoyl-sn-glycero-3[Phospho-rac-(1-glycerol) (Ammonium Salt); 1,2-Distearoyl-sn-glycero-3-phosphoserine (Sodium Salt); Egg-PC; Hydrogenated Egg PC; Hydrogenated Soy PC; 1-Myristoyl-sn-glycero-3-phosphocholine; 1-Palmitoyl-sn-glycero-3-phosphocholine; 1-Stearoyl-sn-glycero-3-phosphocholine; 1-Myristoyl-2-palmitoyl-sn-glycero 3-phosphocholine; 1-Myristoyl-2-stearoyl-sn-glycero-3-phosphocholine; 1-Palmitoyl-2-myristoyl-sn-glycero-3-phosphocholine; 1-Palmitoyl-2-oleoyl-sn-glycero-3-phosphocholine; 1-Palmitoyl-2-oleoyl-sn-glycero-3-phosphoethanolamine; 1-Palmitoyl-2-oleoyl-sn-glycero-3[Phospho-rac-(1-glycerol)] (Sodium Salt); 1-Palmitoyl-2-stearoyl-sn-glycero-3-phosphocholine; 1-Stearoyl-2-myristoyl-sn-glycero-3-phosphocholine; 1-Stearoyl-2-oleoyl-sn-glycero-3-phosphocholine; and 1-Stearoyl-2-palmitoyl-sn-glycero-3-phosphocholine. In some embodiments, the phospholipid is SPOC, egg PC, or Hydrogenated Soy PC (HSPC). In one, the phospholipid in the composition is HSPC. In some embodiments, the lipid is DOPE.

In some embodiments, the particle further comprises a polyethylene glycol (PEG). The PEG can be included in the particle by itself or conjugated with a component present in the particle. For example, the PEG can be conjugated with the platinum based compound or a co-lipid/stabilizer component of the particle. In some embodiments, the PEG is conjugated with a co-lipid component of the particle. Without limitations, the PEG can be conjugated with any co-lipid. For example, the PEG conjugated co-lipid can be selected from the group consisting of PEG conjugated diacylglycerols and dialkylglycerols, PEG-conjugated phosphatidylethanolamine, PEG conjugated to phosphatidic acid, PEG conjugated ceramides (see, U.S. Pat. No. 5,885,613), PEG conjugated dialkylamines, PEG conjugated 1,2-diacyloxypropan-3-amines, and PEG conjugated to 1,2-distearoyl-sn-glycem-3-phosphoethanolamine (DSPE), and any combinations thereof. In some embodiments, the PEG-conjugated lipid is 1,2-distearoyl-sn-glycem-3-phosphoethanolamine-N-[amino(polyethylene glycol)-2000] (DSPE-PEG$_{2000}$).

In some embodiments, the particle further comprises a surfactant. Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In some embodiments, the particle can further comprise a cationic lipid. Exemplary cationic lipids include, but are not limited to, N,N-dioleyl-N,N-dimethylammonium chloride (DODAC), N,N-distearyl-N,N-dimethylammonium bromide (DDAB), N-(1-(2,3 dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3 dioleoyl)propylamine (DODMA), 1,2-DiLinoleyloxy-N,N-dimethylaminopropane (DLinDMA), 1,2-Dilinolenyloxy-N,N-dimethylaminopropane (DLenDMA), 1,2 Dilinoleylcarbamoyloxy-3-dimethylaminopropane (DLin-C-DAP), 1,2-Dilinoleyoxy-3 (dimethylamino)acetoxypropane (DLin-DAC), 1,2-Dilinoleyoxy-3-morpholinopropane (DLin MA), 1,2-Dilinoleoyl-3-dimethylaminopropane (DLinDAP), 1,2-Dilinoleylthio-3 dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis (2-hydroxydodecyl) amino)ethyl)(2-hydroxydodecyl) amino)ethyl)piperazin-1-yl)ethylazanediyl)di.dodecan-2-ol (Tech Gi), or a mixture thereof.

In some embodiments, the particle further comprises a non-cationic lipid. The non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoylphosphatidyethanolamine (SOPE), cholesterol, or a mixture thereof.

The conjugated lipids that inhibit aggregation of particles can also be included in the particles disclosed herein. Such lipids include, but are not limited to, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl (C12), a PEG-dimyristyloxypropyl (C14), a PEG-dipalmityloxypropyl (C16), or a PEG-distearyloxypropyl (Cis). The conjugated lipid that prevents aggregation of particles can be from 0.01 mol % to about 20 mol % or about 2 mol % of the total lipid present in the particle.

In some embodiments, the particle is in the form of a liposome, vesicle, or emulsion. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their nonpolar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

A liposome composition can be prepared by a variety of methods that are known in the art. See e.g., U.S. Pat. Nos. 4,235,871, 4,897,355 and 5,171,678; published PCT applications WO 96/14057 and WO 96/37194; Feigner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757, content of all of which is incorporated herein by reference in its entirety.

The liposomes can be prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, content of which is incorporated herein by reference in its entirety.

Without wishing to be bound by a theory, nanoparticles disclosed herein have higher uptake of platinum in cancer cells relative to cisplatin and oxaliplatin. In some embodiments, the nanoparticles disclosed herein have about 25%, about 50%, about 75%, about 1-fold, about 5-folds, about 10-folds, about 15-folds, about 20-folds, about 25-folds or higher platinum uptake in cancer cells relative to cisplatin or oxaliplatin at equivalent dosage.

In addition, the nanoparticles disclosed herein also have higher accumulation of platinum in tissue, such as, but not limited to a tumor, relative to cisplatin and oxaliplatin when dosed at equivalent amount. For example, the nanoparticles disclosed herein have about 25%, about 50%, about 75%, about 1-fold, about 5-folds, about 10-folds, about 15-folds, about 20-folds, about 25-folds or higher platinum accumulation tissue relative to cisplatin or oxaliplatin when dosed at equivalent amounts.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims Further, unless otherwise required by context, singular teens shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The singular terms "a," "an," and "the" include plural referents unless context clearly indicates otherwise Similarly, the word "of" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean ±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "substituted", whether preceded by the term "optionally" or not, refers to the replacement of hydrogen radicals in a given structure with the radical of a specified substituent. When more than one position in any given structure can be substituted with more than one substituent selected from a specified group, the substituent can be either the same or different at every position. As used herein, the term "substituted" is contemplated to include all permissible substituents of organic compounds In a broad aspect, the permissible substituents include acyclic and cyclic, branched and unbranched, carbocyclic and heterocyclic, aromatic and nonaromatic substituents of organic compounds. Heteroatoms such as nitrogen can have hydrogen substituents and/or any permissible substituents of organic compounds described herein which satisfy the valencies of the heteroatoms.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the disclosed embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Schematic Representation of an Exemplary Synthetic Procedure

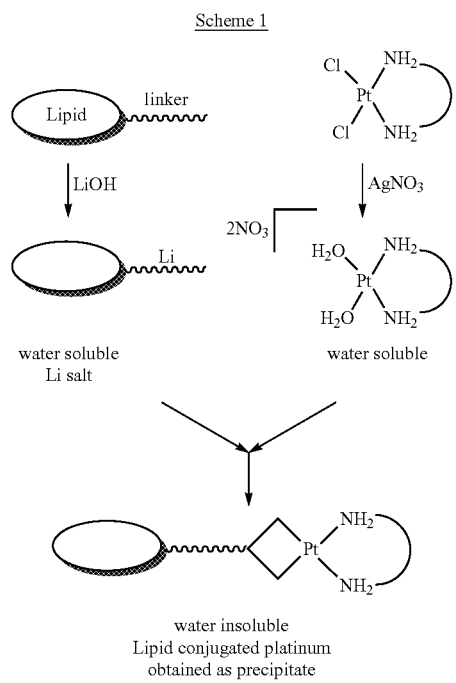

Similar procedures were used for the synthesis of compounds 25-28 and other lipid-5 conjugated platinum compounds. These exemplary procedures worked well for all of the 49 compounds. Introducing extra washing steps helped to increase the purity of compound 26 up to 93% (Table 2).

TABLE 2

Yield and purity of compounds prepared using embodiments of the invention

| Compound | Purity of crude product obtained after optimization of the procedure | Purity after three extra water washes and one acetone wash (1 mL water/0.5 mL acetone per 20 mg compound) | Yield of crude product obtained after optimization of the procedure |
| --- | --- | --- | --- |
| 25 | >70% |  | 75% |
| 26 | >70% | 93% | 65% |
| 27 | >70% |  | 65% |
| 28 | >70% |  | 70% |

Figure 2:
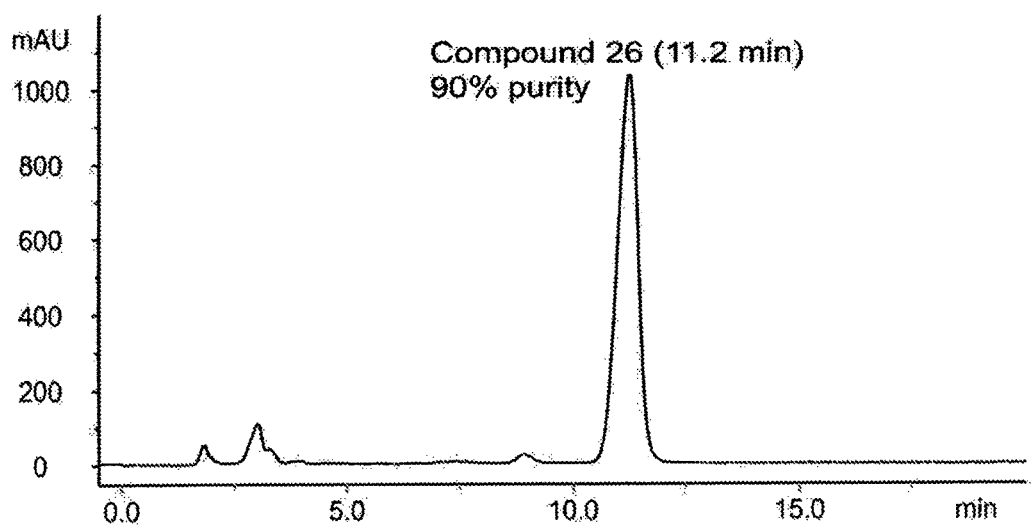
FIG. 2 shows an HPLC profile of compound 26 (RT: 11.2 min) on C18 column after water/acetone wash. The purity of the compound is 90%. Mobile phase: 100% methanol. Detection: 210 nm, UV.

FIG. 1 shows the HPLC profile of compound 26 before water and acetone wash and FIG. 2 shows the HPLC profile of compound 26 after water and acetone wash. This is the maximum purity achieved by washing.

Detailed methods for synthesizing the exemplary compounds above are described in International patent application PCT/US2014/042339, published as WO/2014/201376, which is incorporated herein by reference.

Example 2: Improved Synthetic Routes to Intermediate 6 of Compound 25

A multi-step synthesis of Compound 25 can be found in WO/2014/201376. Reduction in the number of steps for ligand synthesis would help to increase the yield of the Compound 25 (API). The referenced procedure involves six steps to reach Intermediate 6, whereas procedures disclosed herein will take two steps to reach same intermediate. Overall yield of intermediate 6 is 13% in the referenced procedure (Scheme 1). A significant increase in the yield of intermediate 6 was observed (50%) in the new route (Scheme 5).

Scheme 2: Previous synthetic steps for compound 25

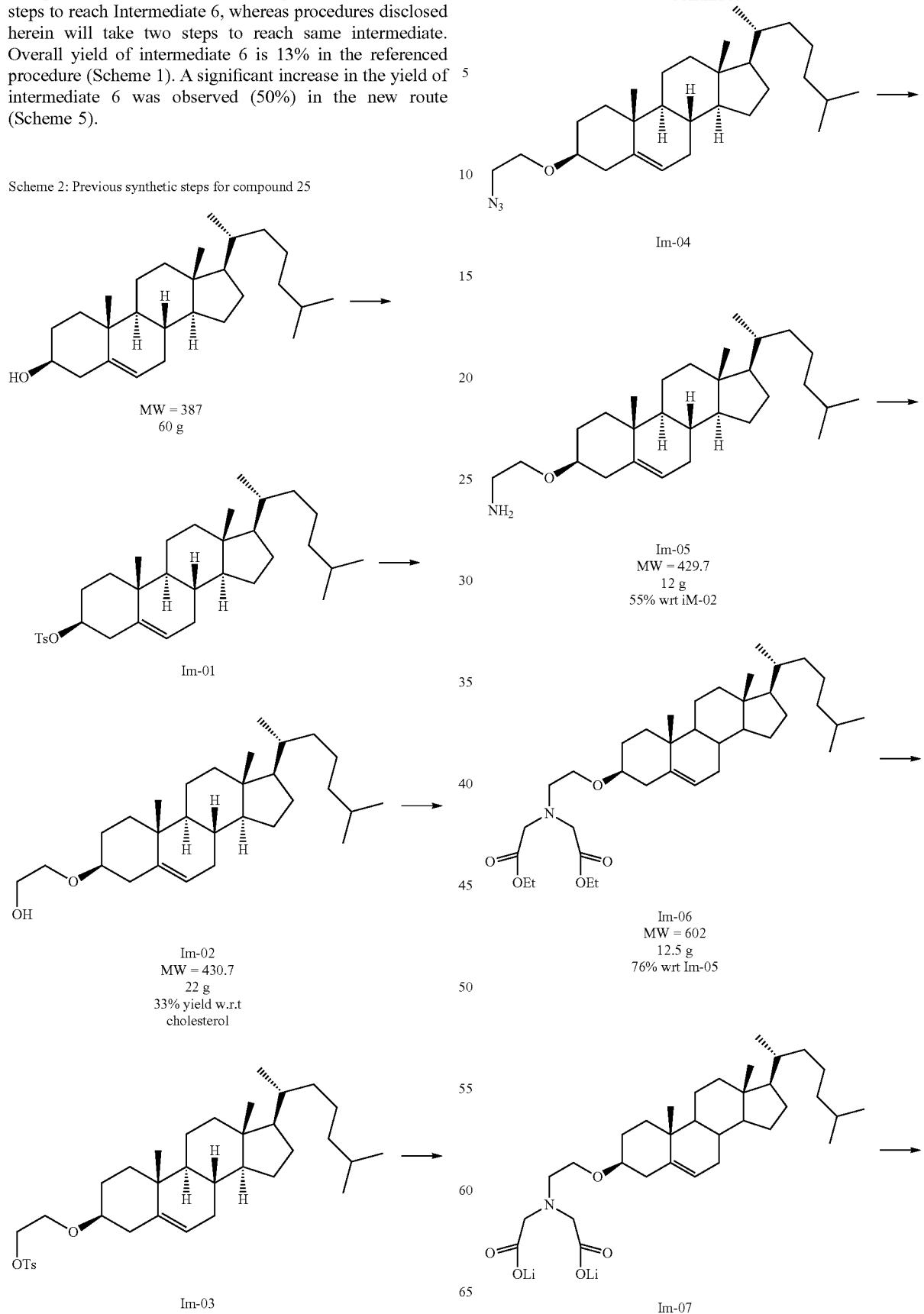

-continued
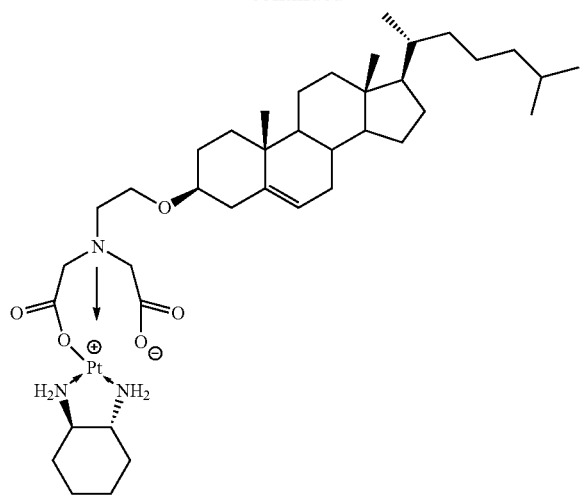
compound 25
MW = 853
15 g crude
83% wrt Im-06
Scheme 3A. Route 1 for the synthesis of intermediate 6 in less number of steps
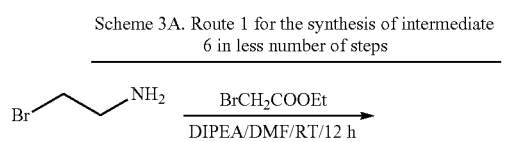
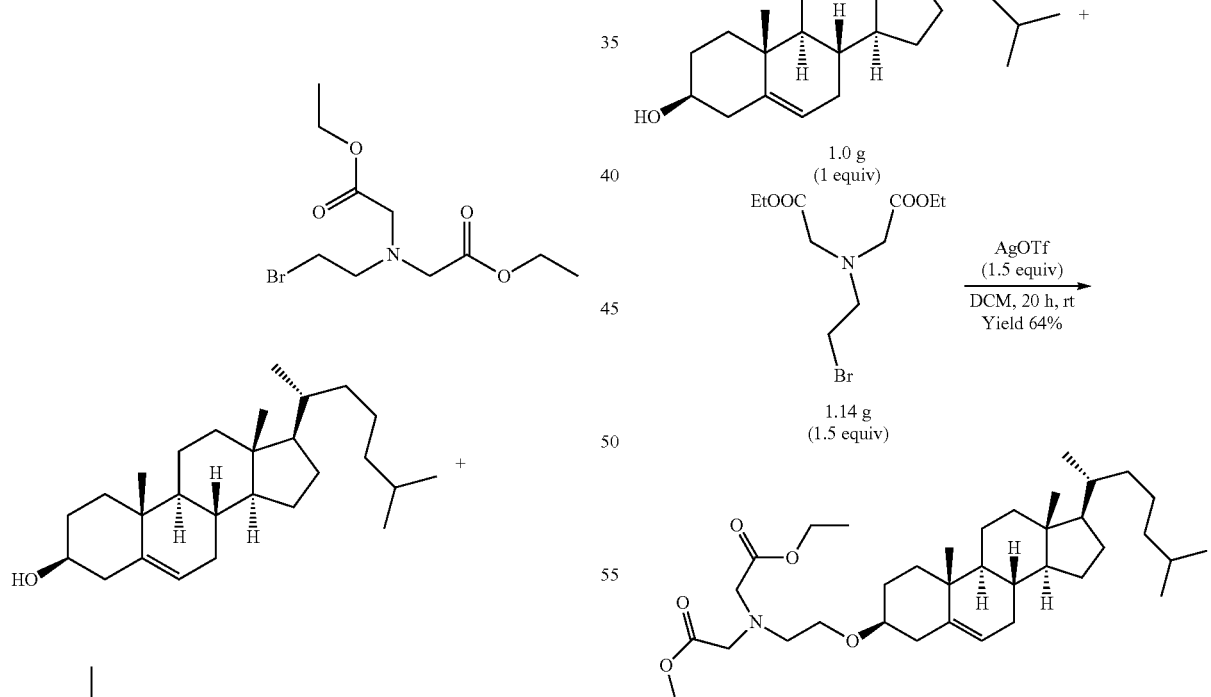
-continued
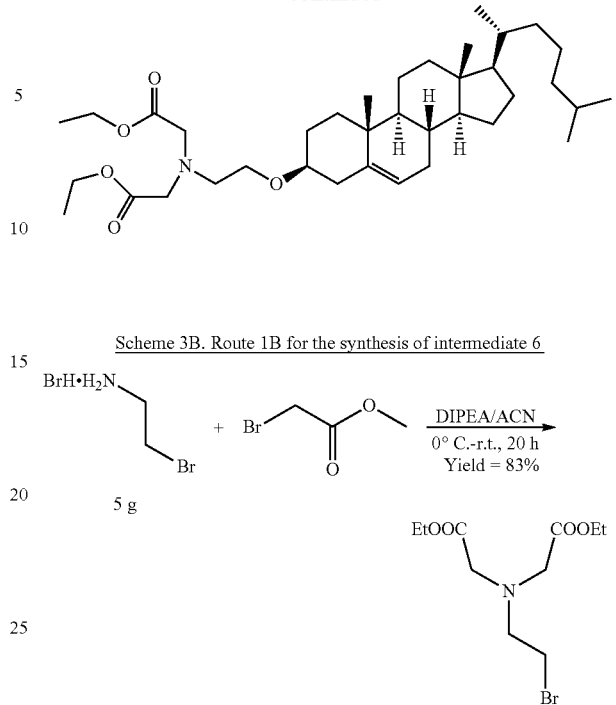
Experimental Detail for Route 1B (Scheme 3B):
2-bromo ethyl amine hydrobromide salt (5.0 g, 25 mmol) was added portion wise to the mixture of bromo ethyl acetate (8.6 ml, 75 mmol), DIPEA (17.5 ml, 100 mmol) and 30 ml dry acetonitrile at 0° C. The mixture was stared at RT for 20 h and then filtered and concentrated on rota vapour. Column chromatography was performed (eluting with ethyl acetate: hexane=1:3) to yield 5.6 g (77%) tertiary bromodiester amine.

To a solution of cholesterol (1.0 g, 2.59 mmol) in anhydrous CH$_2$Cl$_2$ (freshly distilled) (15 ml) at 25° C. was stirred at rt under N2 atmosphere for 10 min. Next AgOTf (1.0 g, 3.88 mmol) was added and stirring was continued for 10 min. Then a solution of tertiary bromo diester amine (1.14 g, 3.88 mmol) in 5 ml DCM was allowed to drip on to the reaction mixture dropwise. After stirring for 20 h at rt, the mixture was neutralized with Et3N and diluted with Chloroform and filtered. It was concentrated and purified by column chromatography (ethyl acetate/hexanes). Yield=1.0 g (64%).

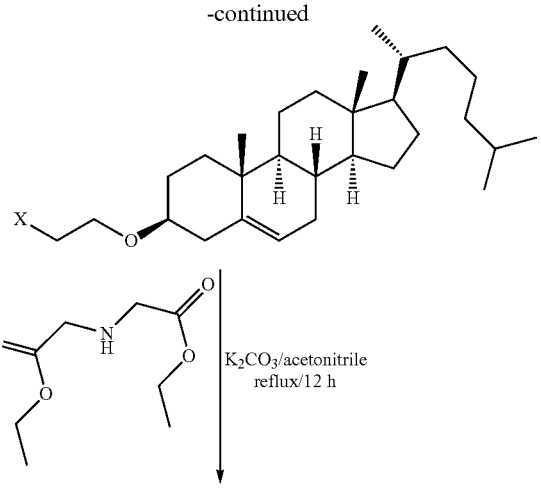

Scheme 4. Alternative route 2 for the synthesis of intermediate 6

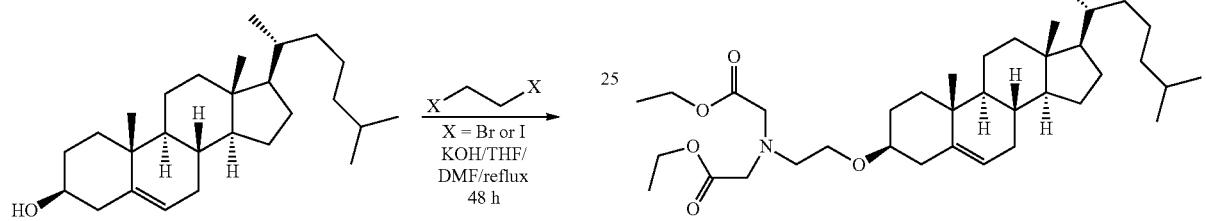

Scheme 5. Alternative Route 3 for the synthesis of intermediate 6

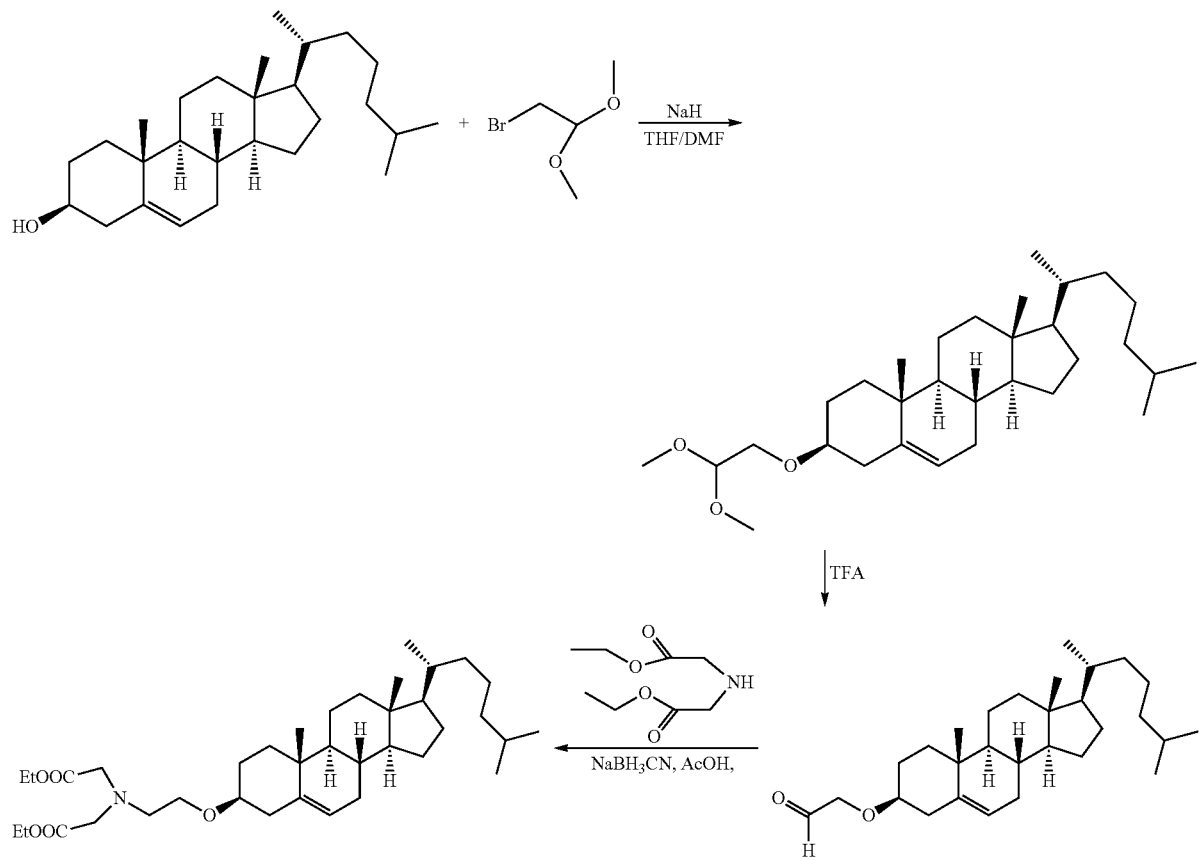

Experimental detail for Route 3 (Scheme 5):

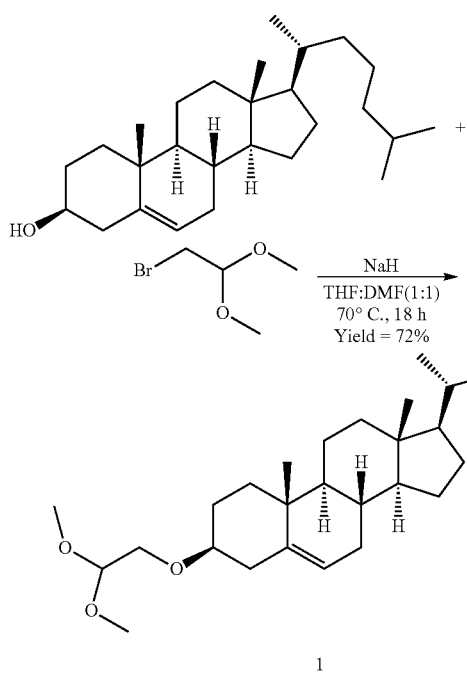

Experimental Procedure:
Cholesterol (10 g, 25.86 mmol) was dissolved in 100 ml dry DMF/THF (1:1) and 60% sodium hydride (w/w) in mineral oil (6.2 g, 155.17 mmol) was added, followed by stirring for 10 min. 2-bromo-1,1-dimethoxy ethane (9.2 ml, 78 mmol) was added dropwise, and the reaction mixture was stirred at 70° C. under reflux for 18 h. The reaction mixture was cooled and quenched by the addition of water. The organic layer was extracted with ethyl acetate, washed several times with water, dried over $Na_2SO_4$ filtered and concentrated and the reaction product was purified by silica gel flash chromatography in 3% EtOAc/Hexane. Yield=8.8 g (72%).

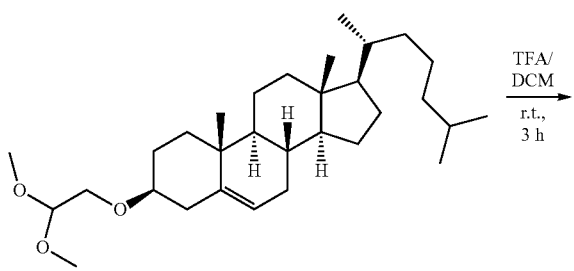

Experimental Procedure:
TFA (2 ml) was added to a solution of compound 1 (0.350 g, 0.737 mmol) in 2 ml DCM and the mixture was stirred at room temperature for 3 h. The mixture was neutralized with 1 N NaOH, extracted twice with DCM and dried over sodium sulfate, filtered and concentrated which was used directly in the next step.

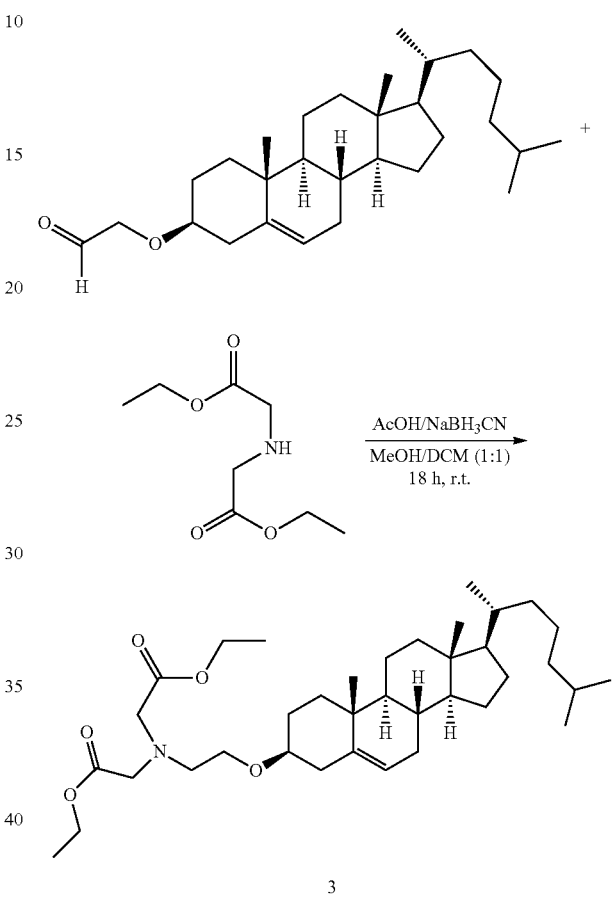

Experimental Procedure:
Compound 2 was dissolved in 3.2 ml of MeOH:DCM (1:1) containing diethyl iminodiacetate (0.161 ml, 0.9 mmol), AcOH (0.214 ml, 3.74 mmol), and $NaBH_3CN$ (0.093 g, 1.48 mmol) were added in succession. The mixture was stirred for 18 h at room temperature, diluted with EtOAc, washed twice with $NaHCO_3$ and water, dried over $Na_2SO_4$, filtered and concentrated. The crude was purified by flash column chromatography on silica gel using EtOAc/Hennes system. Yield=72%.

Scheme 6. Alternative route 4 for the synthesis of intermediate 6

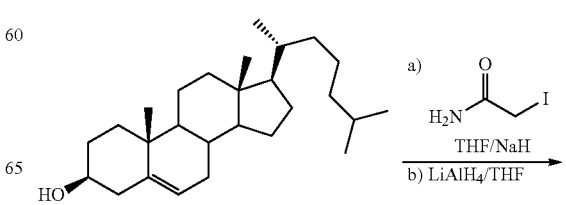

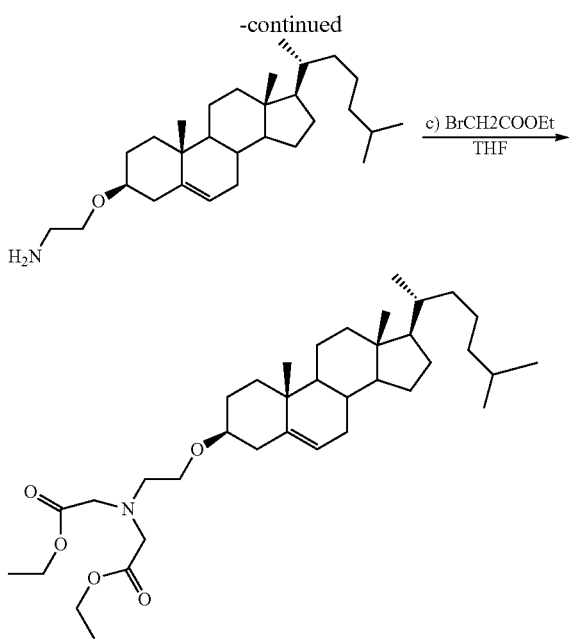

Scheme 7. Alternative route 5 for the synthesis of intermediate 6

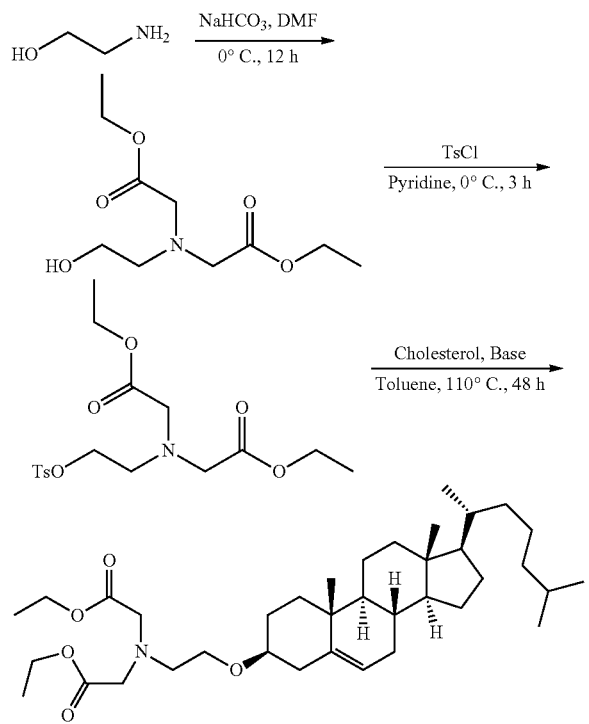

Example 3: HPLC Purification and Analysis

The lipid-conjugated platinum compounds of the present disclosure may be subsequently purified by preparatory reverse-phase HPLC. The compounds can be purified on a column having a C18 stationary phase, a $NH_2$ stationary phase, or a Phenyl stationary phase. Some of the compounds have been found to be unstable on C18, C8, Cyano, and PFP stationary phases resulting in wrong estimation of purity. Therefore, estimation of purity is done either on an $NH_2$ column or a Phenyl column where the compound has been found to be stable.

Purification on a C18 column involves an isocratic method with the mobile phase comprising 98% methanol and 2% water. UV absorbance at 210 nm is monitored. The compound peak is collected, pooled and solvent is removed by evaporation and lyophilization to obtain >99.5% pure compound in powder form.

Purification on an $NH_2$ or a Phenyl column involves a gradient method starting with a higher percentage of water linearly progressing over time to a higher percentage of methanol. UV absorbance at 210 nm is monitored. The compound peak is collected, pooled and solvent is removed by evaporation and lyophilization to obtain >99.5% pure compound in powder form.

The analytical method for purity estimation is done using an $NH_2$ or a Phenyl stationary phase. The compound is dissolved in methanol (>1 mg/mL). The analysis is done with a water/methanol gradient and a UV/PDA detector at 210 nm. The purity is measured by calculating the percentage of compound peak area from the total peak area. To account for ghost peaks, the analysis is done after overlaying the chromatogram from a pure methanol injection.

Figure 3:
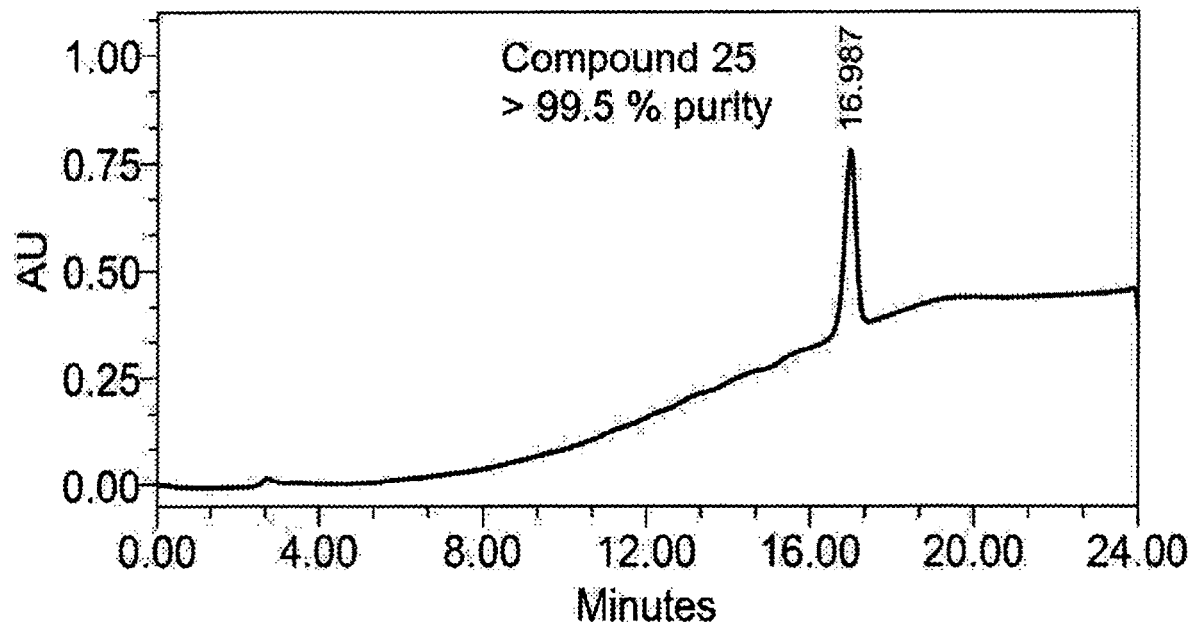
FIG. 3 shows an example analytical profile of compound 25 after HPLC purification. The purity is >99.5%. The purity is calculated after overlaying the blank spectra (not shown).
Figure 4:
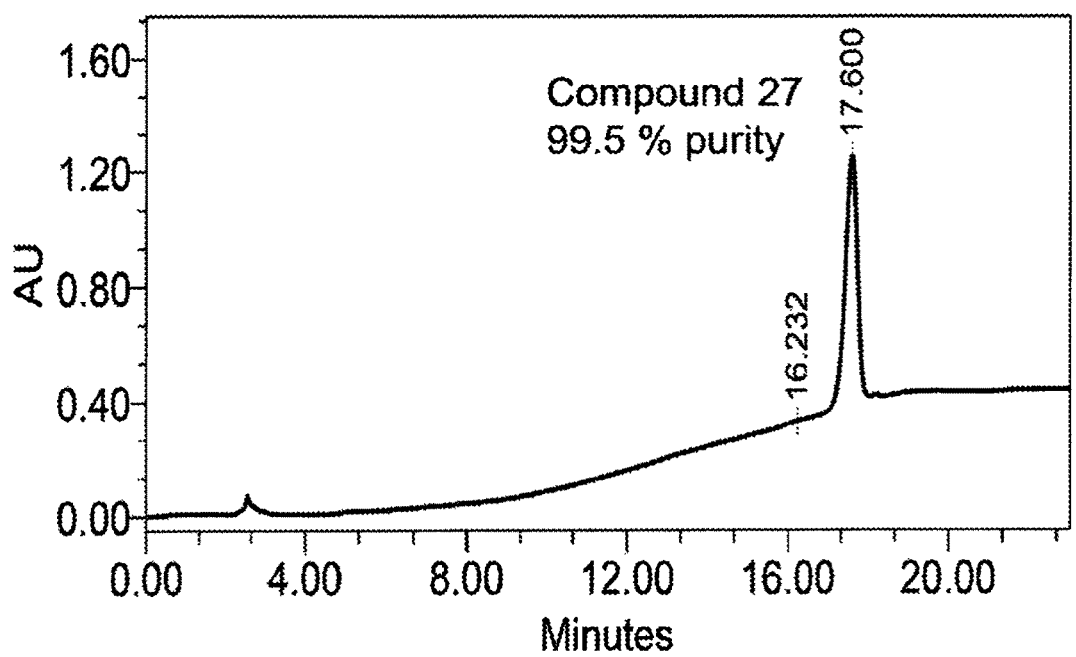
FIG. 4 shows an example analytical profile of compound 27 after HPLC purification. The purity is 99.5%. The purity is calculated after overlaying the blank spectra (not shown).
Figure 5:
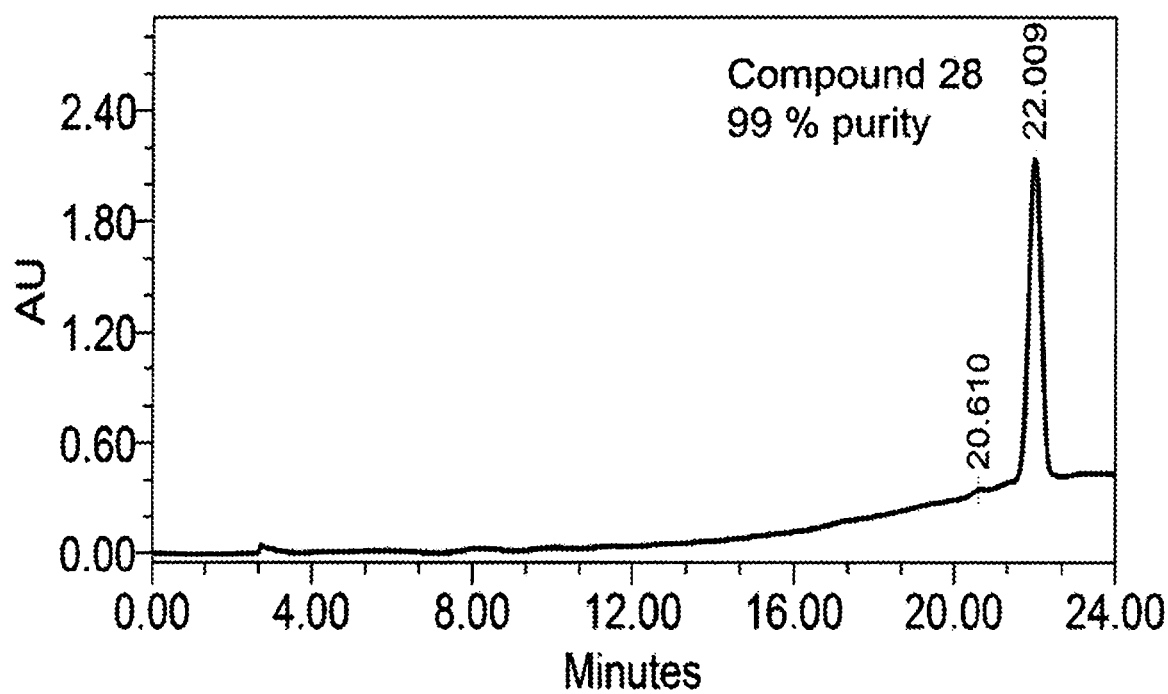
FIG. 5 shows an example analytical profile of compound 28 after HPLC purification. The purity is 99%. The purity is calculated after overlaying the blank spectra (not shown).
Figure 6:
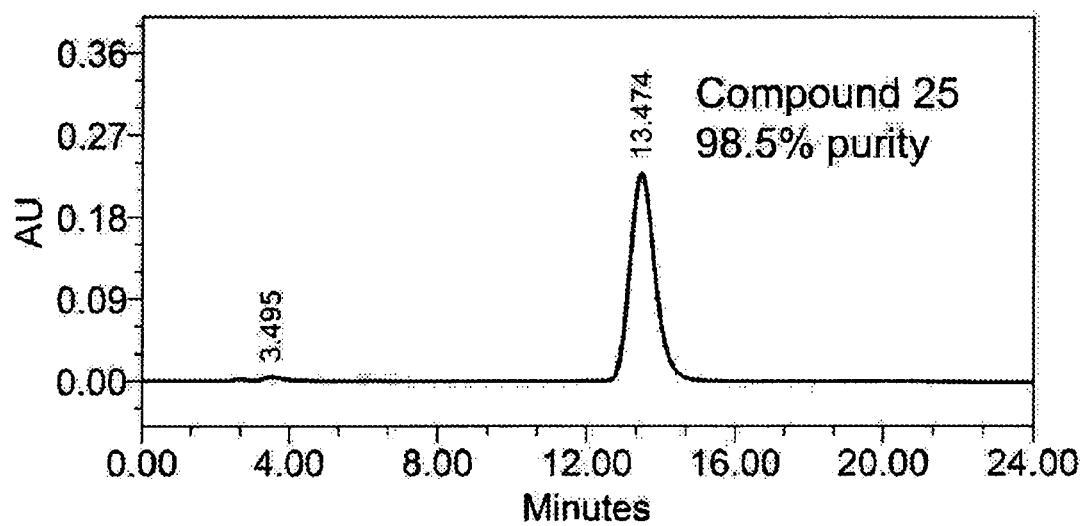
FIGS. 6A and 6B show an example analytical profile of compound 25 after HPLC purification. The purity is 98.5% on C18 column (FIG. 6A) but ~100% on amino column (FIG. 6B) proving the degradation of the compound on C18 column. This result highlights the choice of analysis method for purity.
Figure 6:
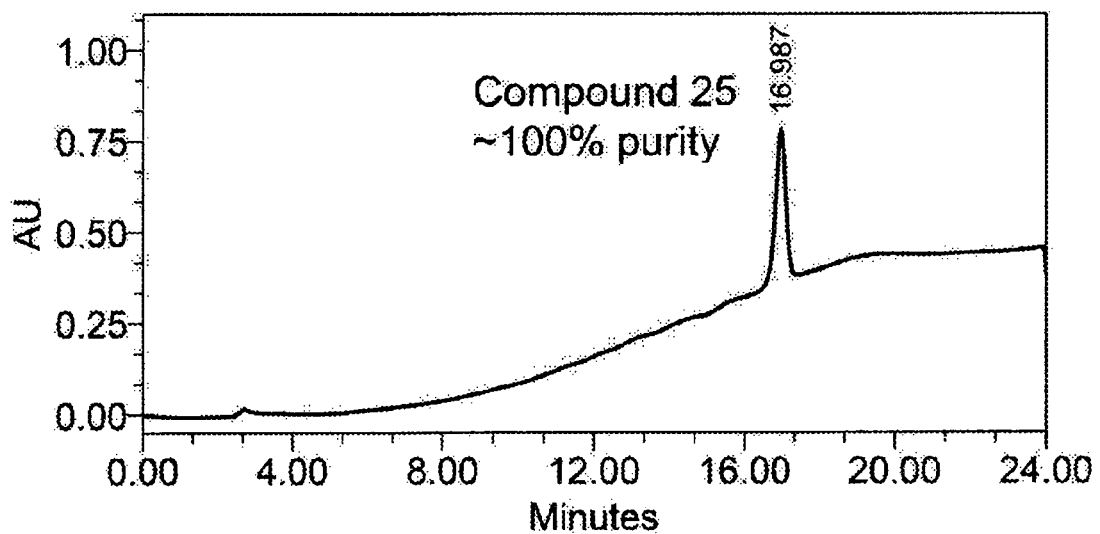
Figure 7:
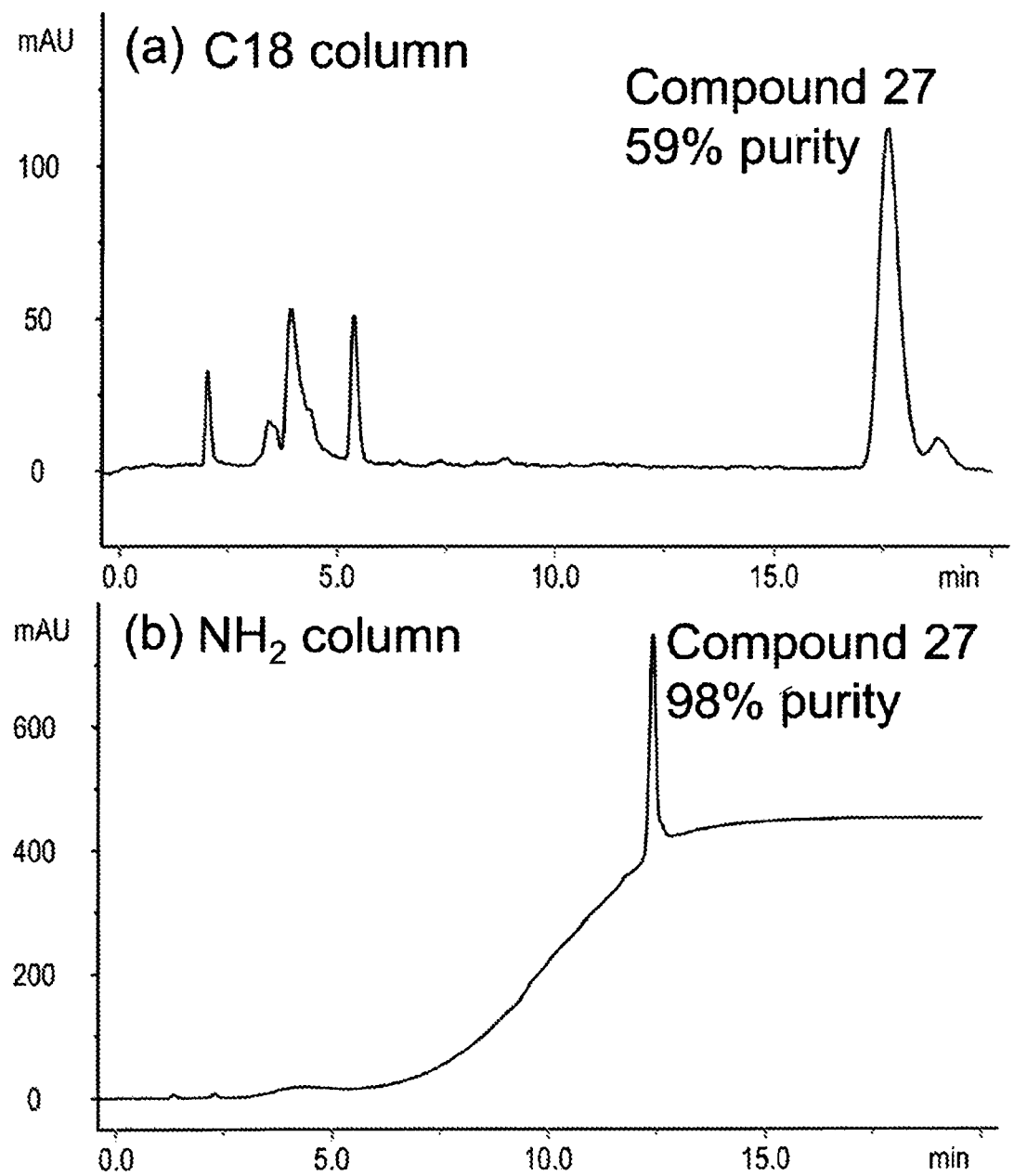
FIGS. 7A and 7B shows an example analytical profile of compound 27 after HPLC purification. The purity is 59% on C18 column (FIG. 7A) but 98% on amino column (FIG. 7B) proving the degradation of compound on C18 column. This result highlights the choice of analysis method for purity.

FIG. 3 shows the analytical profile of compound 25 after HPLC purification. FIGS. 6A and 6B show the comparison HPLC profiles of compound 25 on C18 and $NH_2$ columns. FIG. 4 shows the analytical profile of compound 27 after HPLC purification. FIGS. 7A and 7B show the comparison HPLC profiles of compound 27 on C18 and $NH_2$ columns. FIG. 5 shows the analytical profile of compound 28 after HPLC purification.

Example 4: Method for Producing Nanoparticles Comprising Compound 25

Soy-phosphatidyl choline (fully hydrogenated, HSPC), cholesterol (CHOL), Compound 25 and 1,2-distearoyl-sn-glycero-3-phosphoethanolamine-N-[amino(polyethylene glycol)-2000] (DSPE-PEG$_{2000}$), taken in 55:3:38:4 mol % ratios were dissolved in DCM/MeOH (1:1, v/v) mixture. All lipid solutions were mixed homogeneously in a round bottom flask, organic solvent was evaporated by rotary evaporator, and the lipid film was kept under high vacuum for 4-5 hr. The thin film was then hydrated by adding 40 ml of 5% lactose solution to it, and allowed to rotate in rotary water bath for 1.0 h at 65° C. Next, hydrated supra-molecules were sequentially extruded through 400 nm, 200 nm and 100 nm pore size membranes (Whatman® filters) supported by filter support for 10 times using a LIPEX™ extruder (100 mL) connected to a circulating water bath at 65° C. Atomic Absorption Spectrometer (AAS) measurement of Pt reveals the final Pt-equivalent of this formulation to be 2.33 mg/ml and % encapsulation efficiency to be 32.7 mol % of Compound 25.

The aforesaid supra-molecular formulation was lyophilized (5% Lactose solution was used as Cryo-Protectant) over 16-20 hrs. The white solid powder formed thereafter was reconstituted by adding the required volume of sterile water for injection. DLS study of this reconstituted supra-molecular formulation reveals similar size, PDI, surface potential of supra-molecules as it had before lyophilization.

Example 5: Method for Producing Fluorescent Nanoparticles Comprising Compound 25

HSPC, CHOL, Compound 25, DSPE-PEG$_{2000}$ and Liss Rhod PE (fluorescent dye) taken in 61.02:3.55:31.32:3.55:

0.56 mol % ratio, were dissolved in DCM/MeOH (1:1, v/v) mixture. All lipid solutions were mixed homogeneously in a round bottom flask (wrapped with Aluminium foil) and organic solvent was evaporated by rotary evaporator. The thin film was then hydrated by adding 2.5 mL of 5% lactose solution to it, and allowed to rotate in rotary water bath for 1.0 h at 65° C. Next, hydrated supra-molecules were sequentially extruded through 400 nm, 200 nm and 100 nm pore size membranes (Whatman® filters) supported by filter support for 10 times using a LIPEX™ extruder (10 mL) connected to a circulating water bath at 65° C. Atomic Absorption Spectrometer (AAS) measurement of Pt reveals the final Pt-equivalent of this formulation to be 1.2 mg/mL and % encapsulation efficiency to be 25 mol % of Compound 25.

The aforesaid supra-molecular formulation was lyophilized (5% Lactose solution was used as Cryo-Protectant) over 16-20 hrs. The white solid powder formed thereafter was reconstituted by adding the required volume of sterile water for injection. DLS study of this reconstituted supra-molecular formulation reveals similar size, PDI, surface potential of supra-molecules as it had before lyophilization.

Example 6: Method for Producing Nanoparticles Comprising Compound 25

HSPC, CHOL, Compound 25 and DSPE-PEG$_{2000}$, taken in 65.57:10.93:21.86:1.64 mol % ratios were dissolved in DCM/MeOH (1:1, v/v) mixture. All lipid solutions were mixed homogeneously in a round bottom flask and organic solvent was evaporated by rotary evaporator. The thin film was then hydrated by adding 4 mL of 5% Sucrose solution to it, and allowed to rotate in rotary water bath for 1.0 h at 65° C. Next, hydrated supra-molecules were sequentially extruded through 400 nm, 200 rim and 80 rim pore size membranes (Whatman® filters) at 65° C. supported by filter support for 11 times using Avanti extruder (1 mL) placed over a hot plate. The supra-molecular formulation, followed by extrusion, was passed through a Sephadex G-25 (PD-10) de-salting column equilibrated with 5% Sucrose solution, and different fractions were collected. The supra-molecule containing fractions were pooled together and concentrated to a final volume of 3 mL using a centrifugal filter unit (Amicon Ultra, 30 kD) at 3000 g for 15 min. Atomic Absorption Spectrometer (AAS) measurement of Pt reveals the final Pt-equivalent of this formulation to be 0.43 mg/mL and % encapsulation efficiency to be 12.8 mol % of Compound 25.

The aforesaid supra-molecular formulation was lyophilized (5% Sucrose solution was used as Cryo-Protectant) over 16-20 hrs. The white solid powder formed thereafter was reconstituted by adding the required volume of sterile water for injection. DLS study of this reconstituted supra-molecular formulation reveals similar size, PDI, surface potential of supra-molecules as it had before lyophilization.

Example 7: Method for Producing Nanoparticles Comprising Compound 25

HSPC, CHOL, Compound 25, DSPE-PEG$_{2000}$, taken in 62.54:324:32.45:1.77 mol % ratio in a glass vial, were dissolved in DCM/MeOH (1:1, v/v) mixture. 4 mL of 5% lactose solution was taken in a pear-shaped round bottom flask and the organic phase was slowly added to it. The mixture was gently vortexed for 1 min. The organic solvent was removed by N$_2$-flush through rotary evaporator at 65° C. for 1 hour resulting in a viscous suspension. It was sonicated for 5 cycles using a probe-sonicator. Next, hydrated supra-molecules were sequentially extruded through 400 nm, 200 nm and 80 nm pore size membrane (Whatman® filters) at 65° C. supported by filter support for 9 times using Avanti extruder (1 mL) placed over hot plate. Atomic Absorption Spectrometer (AAS) measurement of Pt reveals the final Pt-equivalent of this formulation to be 1.56 mg/mL and % encapsulation efficiency to be 19 mol % of Compound 25.

The aforesaid supra-molecular formulation was lyophilized (5% Lactose solution was used as Cryo-Protectant) over 16-20 hrs. The white solid powder formed thereafter was reconstituted by adding the required volume of sterile water for injection. DLS study of this reconstituted supra-molecular formulation reveals similar size, PDI, surface potential of supra-molecules as it had before lyophilization.

Example 8: Characterization of Supra-Molecular Formulation of Compound 25

Figure 8:
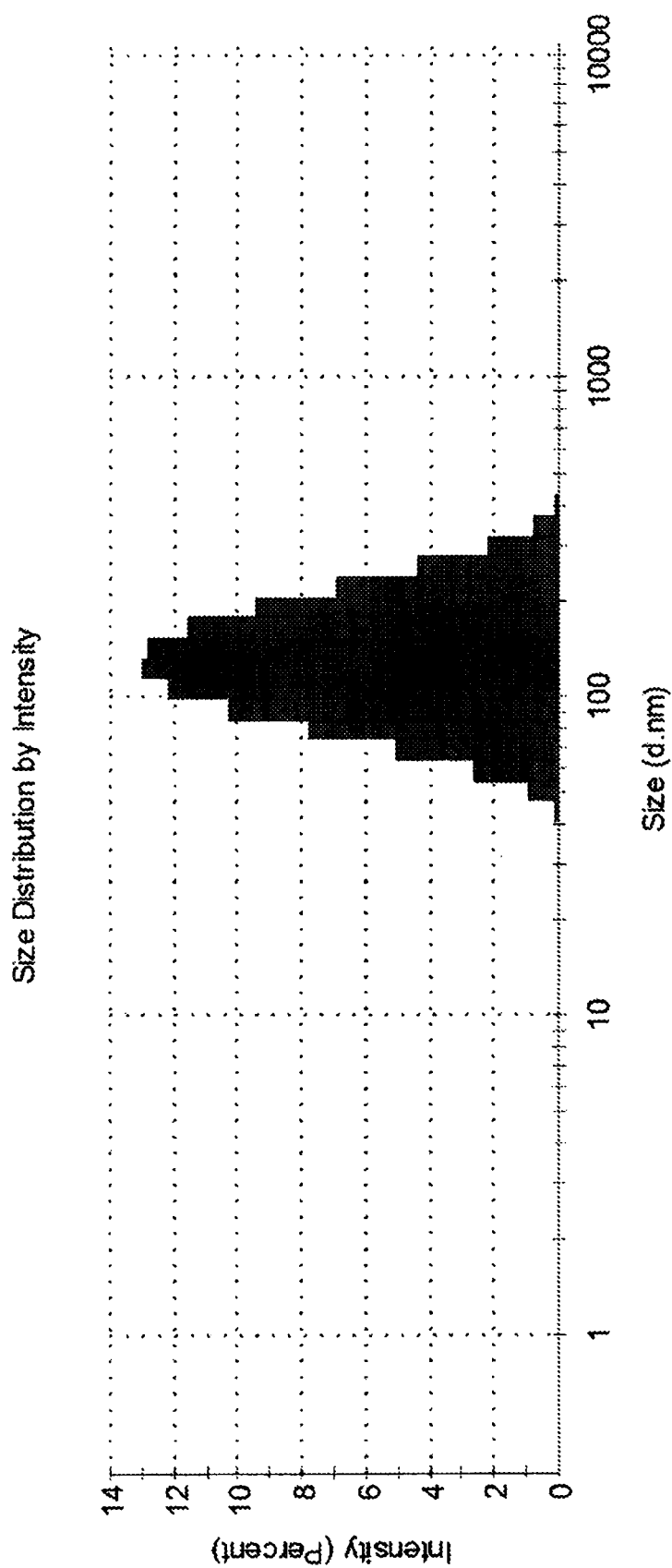
FIG. 8 shows a DLS histogram of the supramolecular formulation of compound 25.
Figure 9:
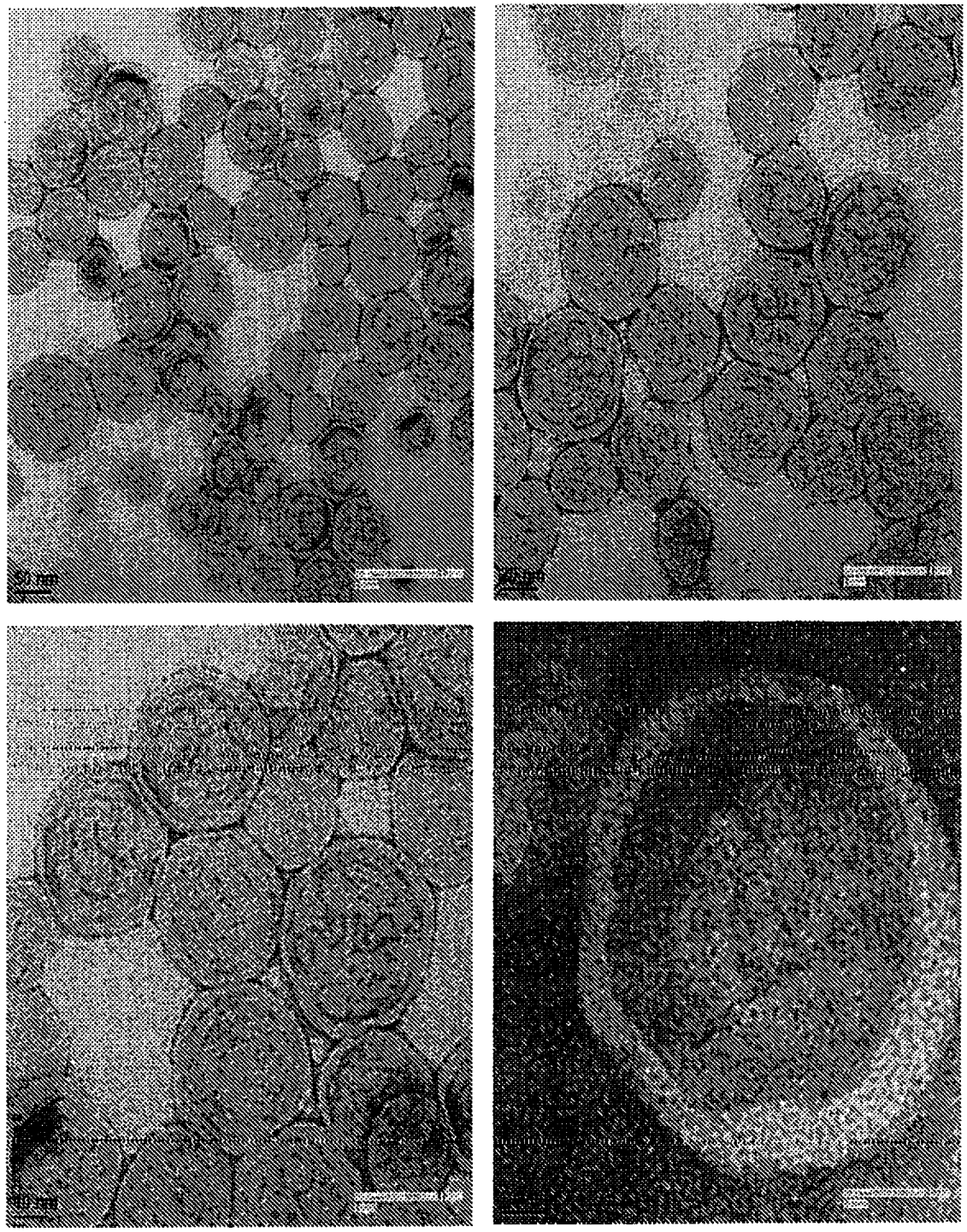
FIG. 9 shows transmission electron microscope (TEM) images of nanoparticles comprising lipid-conjugated platinum compounds according to the present invention. Nanoparticles are shown at various magnifications as can be seen from the scale bars on each image.
Figure 10:
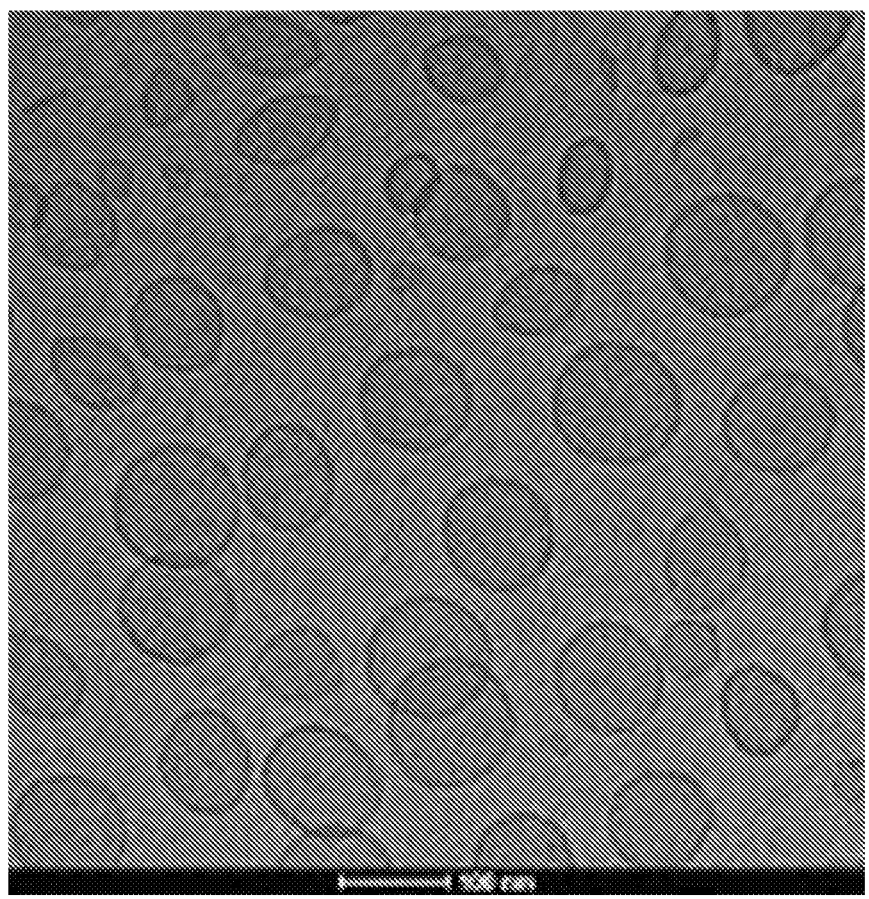
FIG. 10: Shows a Cryo-Transmission electron microscope (Cryo-TEM) image of nanoparticles comprising lipid-conjugated platinum compounds according to an embodiment of the present invention.

Characterization of Supra-Molecular Formulation by Dynamic Light Scattering (DLS):

The cumulative particle size of the formulation produced in Example 7 was measured by Dynamic Light Scattering method using Zetasizer Nano ZS90 (Malvern, UK). 50 µL of formulation was diluted to 1 mL using DI water and measurement was performed at 90 degree scattering angle at 25° C. to get the average particle size distribution. The DLS histogram of the exemplary formulation is shown in FIG. 8. As seen from FIG. 8, the average particle size was in the range of about 40 nm to about 300 nm. Transmission electron microscope (TEM) images of nanoparticles comprising lipid-conjugated platinum compounds according to an embodiment of the invention are shown in FIG. 9. Nanoparticles are shown at various magnifications as can be seen from the scale bars on each image The zeta potential was also measured using the same instrument, the Zetasizer ZS90. The results of the zeta potential measurements are summarized in Table 3.

TABLE 3

| DLS data (from prep-29 to 37) | | | | | |
|---|---|---|---|---|---|
| Before lyophilization | | | After lyophilization | | |
| Zavg (nm) | PDI | ZP (mV) | Zavg (nm) | PDI | ZP (mV) |
| 110.4 ± 4.74 | 0.117 ± 0.02 | −27.2 ± 4.27 | 111.14 ± 5.62 | 0.105 ± 0.028 | −24.06 ± 4.92 |

Atomic Absorption Spectroscopy (AAS):

The Pt-equivalent in formulation was quantified by using Atomic Absorption Spectrometer (AAS) measurement. The results of AAS are summarized in Table 4.

TABLE 4

AAS data (from prep-29 to 37)

| Formulation Start Pt | Before lyophilization | | After lyophilization | |
|---|---|---|---|---|
| (mg/ml) | (Pt mg/ml) | % EE | (Pt mg/ml) | % EE |
| 1.95 | 1.67 ± 0.085 | 85.7 ± 0.08 | 1.59 ± 0.106 | 81.6 ± 0.10 |

Stability of the exemplary supra-molecular formulation was determined and is reported in Table 5.

Stability Analysis of Compound 25 (IO-125, Prep-47):
Stability condition: ICH Q1 A (R2) Stability testing of New Drug Substances and Products
Accelerated study: (6 months)

TABLE 5

Compound 25 (IO-125, prep-47) stability data

| Conditions | Time points (month) | Zavg (nm) | PDI | ZP (mV) | Pt (mg/ml)- AAS | Comp 25 (IO-125) (mg/ml)- HPLC |
|---|---|---|---|---|---|---|
| Initial point | 0 | 117.0 ± 0.84 | 0.102 ± 0.02 | −31.5 ± 2.94 | 1.59 ± 0.04 | 7.95 ± 0.41 |
| 25° C. ± 2° C./ 60% RH ± 5% RH | $1^{st}$ | 117.0 ± 1.33 | 0.101 ± 0.01 | −24.6 ± 0.97 | 1.9 ± 0.15 | 7.52 ± 0.09 |
| | $3^{rd}$ | 114.1 ± 0.9 | 0.109 ± 0.02 | −26.0 ± 1.35 | 1.82 ± 0.02 | 8.06 ± 1.02 |
| | $6^{th}$ | 120.0 ± 1.21 | 0.107 ± 0.01 | −29.7 ± 0.57 | 1.70 ± 0.16 | 8.54 ± 0.17 |
| 40° C. ± 2° C./ 75% RH ± 5% RH | $1^{st}$ | 115.8 ± 1.24 | 0.088 ± 0.00 | −23.58 ± 1.66 | 2.02 ± 0.08 | 7.31 ± 0.10 |
| | $3^{rd}$ | 113.9 ± 2.06 | 0.109 ± 0.01 | −26.1 ± 0.84 | 2.31 ± 0.25 | 7.31 ± 0.10 |
| | $6^{th}$ | 120.0 ± 1.21 | 0.107 ± 0.01 | −29.7 ± 0.57 | 1.70 ± 0.16 | 8.54 ± 0.17 |

Example 9: Method for Producing pH Sensitive Nanoparticles Comprising Compound and DOPE as the Lipid Component DOPE is known to form pH sensitive supra molecular formulation (Pharmacy and Pharmacology 2007, 59, 469). Without wishing to be bound by a theory, the following factors are responsible for the pH sensitivity of DOPE: 1) protonatable acid group; 2) Low transition temperature; and 3) presence of double bond in the alkyl chains.

Procedure: 1,2-dioleoyl-sn-glycero-3-phosphoethanolamine (DOPE), hydro soya PC (HSPC), cholesterol, compound 25 and 1,2-distearoyl-sn-glycero-3-phosphoethanolamine-N-10 [amino(polyethylene glycol)-2000] (DSPE-PEG$_{2000}$), taken in 40:28:3:25:4 mol % (total phospholipids concentration was equal to 19.7 mM) ratios were dissolved in CHCl$_3$/MeOH (1:1, v/v) mixture. Table 6 summarizes the lipid compositions of the various formulations produced in this example.

TABLE 6

Difference in lipid composition of compound 25 formulations in presence and in absence of DOPE

| | mol % | |
|---|---|---|
| Lipids | IO-125 (Comp 25) Prep-77 | IO-125 (comp 25) Prep-78 |
| DOPE | — | 40.0 |
| HSPC | 55.0 | 28.0 |

TABLE 6-continued

Difference in lipid composition of compound 25 formulations in presence and in absence of DOPE

| | mol % | |
|---|---|---|
| Lipids | IO-125 (Comp 25) Prep-77 | IO-125 (comp 25) Prep-78 |
| Chol | 3.0 | 3.0 |
| IO-125 | 38.0 | 25.0 |
| PEG-DSPE$_{2000}$ | 4.0 | 4.0 |

All lipid solutions were mixed homogeneously in a round bottom flask, organic solvent was evaporated by rotary evaporator, and the lipid film was kept under high vacuum for 4-5 hr (*Experimental Biology and Medicine* 2012; 237: 973-984, *International Journal of Nanomedicine* 2012:7 5259-5269&*Journal of Liposome Research*, 2011; 21(1): 60-69). The thin film was then hydrated by adding 5% lactose solution to it, and allowed to rotate in rotary water bath for 1.0 h at 65° C. Next, the hydrated supra-molecular formulation was sequentially extruded through 400 nm, 200 nm and 100 nm pore size membranes (Whatman® filters) supported by filter support for 10 times using a LIPEX™ extruder (10 mL) connected to a circulating water bath at 65° C. Atomic Absorption Spectrometer (AAS) measurement of Pt reveals the final Pt-equivalent of this formulation to be 1.13 mg/mL.

Figure 11:
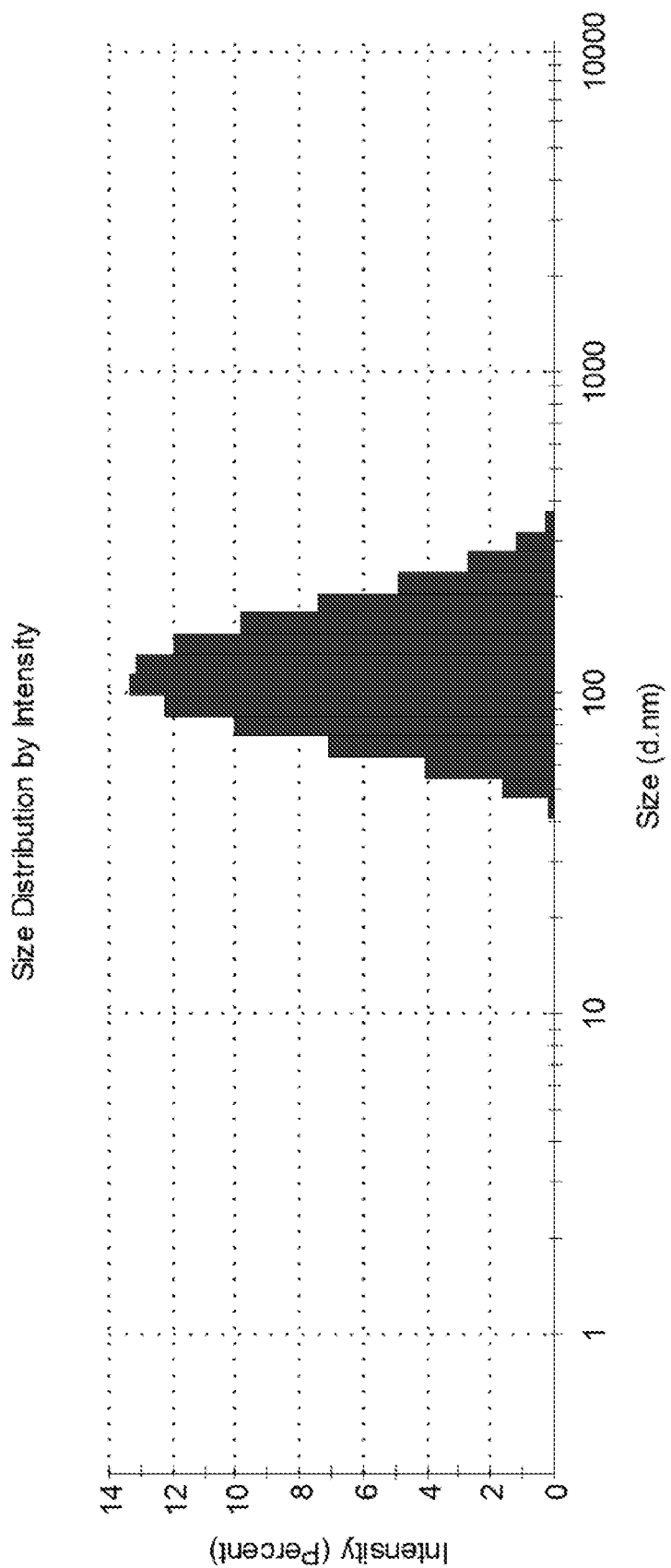
FIG. 11 shows a DLS histogram of the supramolecular formulation of compound 25 with dioleoyl phosphatidylethanolamine (DOPE).

The aforesaid supra-molecular formulation was lyophilized (5% Lactose solution was used as Cryo-Protectant) over 12-15 hrs. The white solid powder formed thereafter was reconstituted by adding the required volume of milliQ water and DLS measured. The DLS histogram can be seen in FIG. 11 and data is summarized in Table 7.

TABLE 7

Summary of DLS data for exemplary DOPE containing formulation

| Zavg (nm) | PDI | ZP (mV) |
|---|---|---|
| 150.9 ± 0.42 | 0.118 ± 0.013 | −29.4 ± 0.0 |

Figure 12:
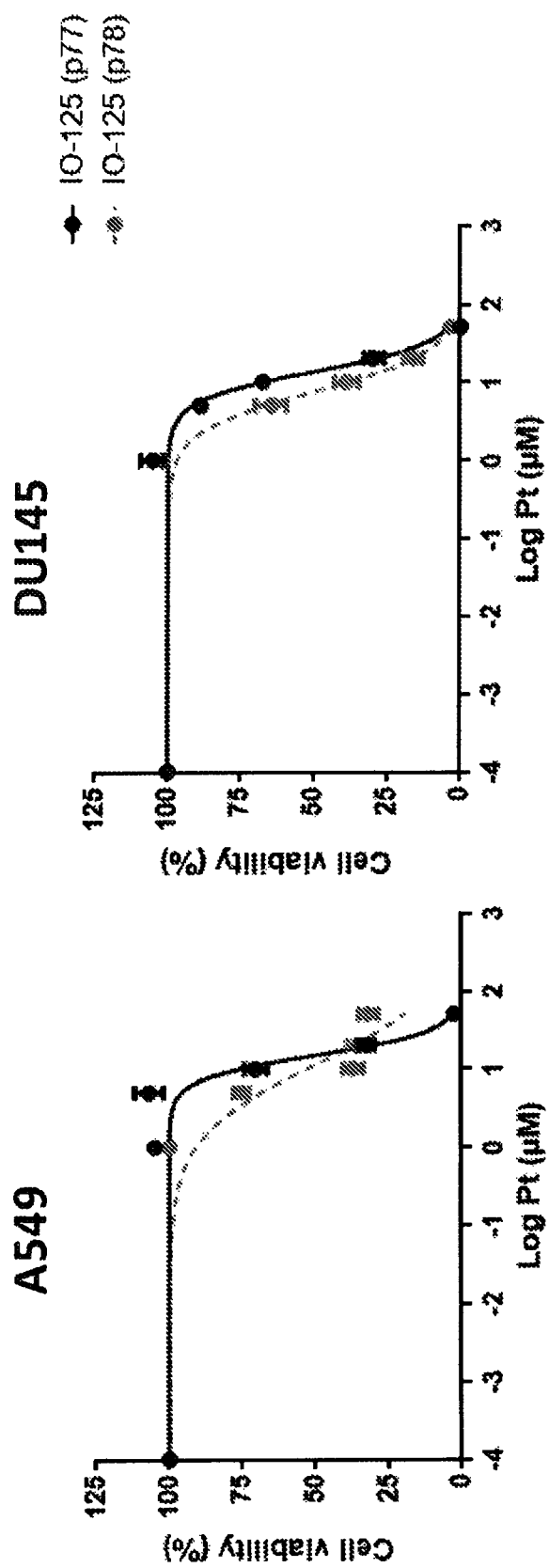
FIG. 12 shows DOPE containing formulation of Compound 25 (IO-125) has better efficacy than without DOPE formulations in A549 and DU145 cell lines.

Efficacy of the DOPE containing formulation was determined. As shown in FIG. 12 and summarized in TABLE 8, DOPE containing formulation showed relatively better efficacy in A549 and DU145 cells lines than a similar formulation lacking DOPE.

TABLE 8

Efficacy of DOPE containing formulation in A549 and DU145 cell lines

| Compound | IC$_{50}$ (μM) in A549 | IC$_{50}$ (μM) in DU145 |
|---|---|---|
| IO-125 (prep 77) | 14.88 | 13.54 |
| IO-125 (prep 78) | 11.31 | 7.506 |

Example 10: Improved Synthesis of Intermediate 6 (Im-06)

Purity of the intermediate 6 (Im-06) synthesized using the synthetic Scheme 3 shown in Example 2 varied from 88 to 92%. It was desired to improve the purity to the required specification of 95%. This was accomplished via forming an acid salt of the intermediate Im-06 followed by desaltification as shown in Scheme 8.

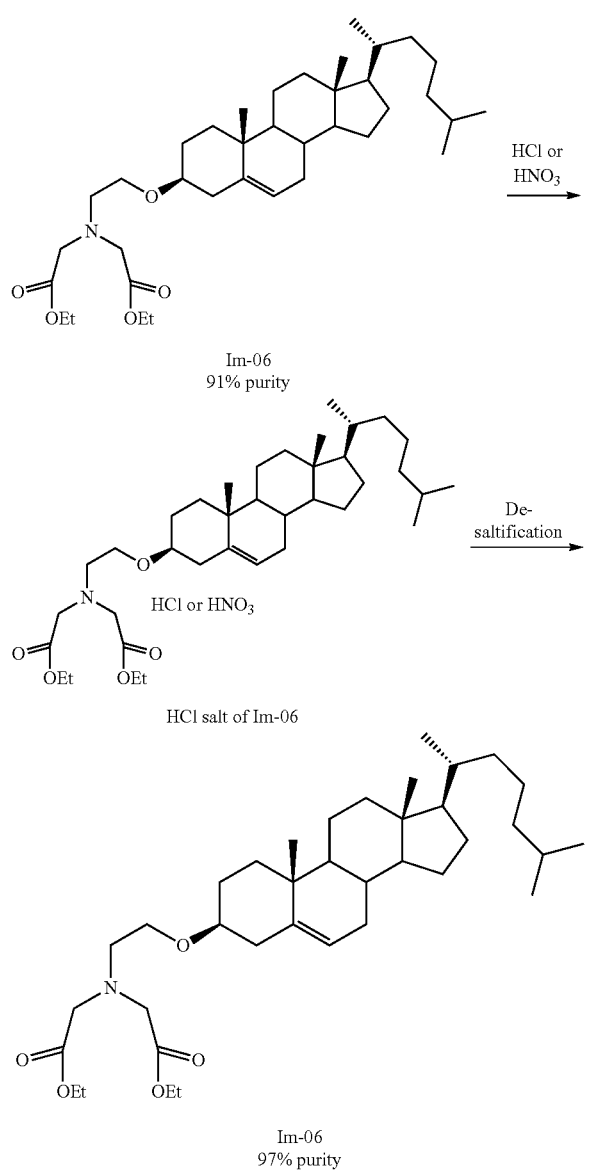

SCHEME 8

Figure 13:
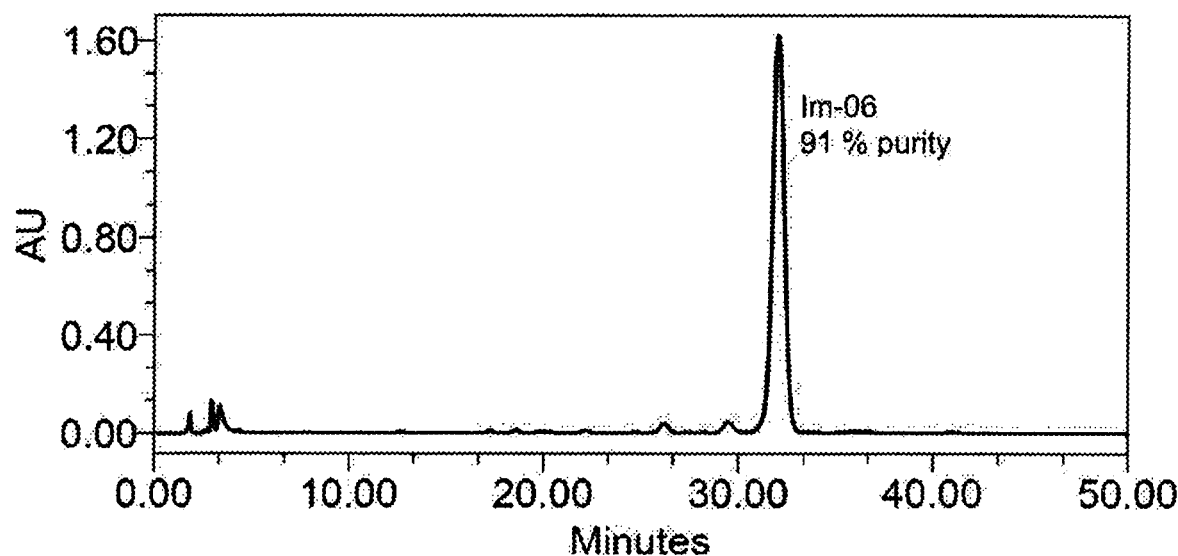
FIG. 13 shows the HPLC profile of intermediate Im-06 before HCl salt formation. As can be seen, purity of the Im-06 before HCl salt formation was 91%.

Step 1: HCl or HNO$_3$ Salt Formation at 10 g Scale:

To Im-06 (10.0 g, 91% purity seen in FIG. 13) in EtOAc (90 mL) at it, was added 5 N HCl or HNO$_3$/EtOAc (30 mL). The mixture was heated and stirred for 30 min. The white precipitate was filtrated. The cake was washed with cold EtOAc, dried to afford Im-06-HCl or HNO$_3$ salt (8 g, 80% yield, HPLC 96.0%) as a white solid.

Recrystallization: A mixture of Im-06-HCl or HNO$_3$ salt (8 g) in EtOAc/EtOH (50 ml/8 ml) was heated to 80° C. with agitation (until solubilize). The solution was cooled to room temperature for 2 h without agitation. The precipitate was collected by filtration, washed with EtOAc to afford Im-06-HCl or HNO$_3$ (crystalline)(5-6 g, HPLC 97%) as a white solid.

Figure 14:
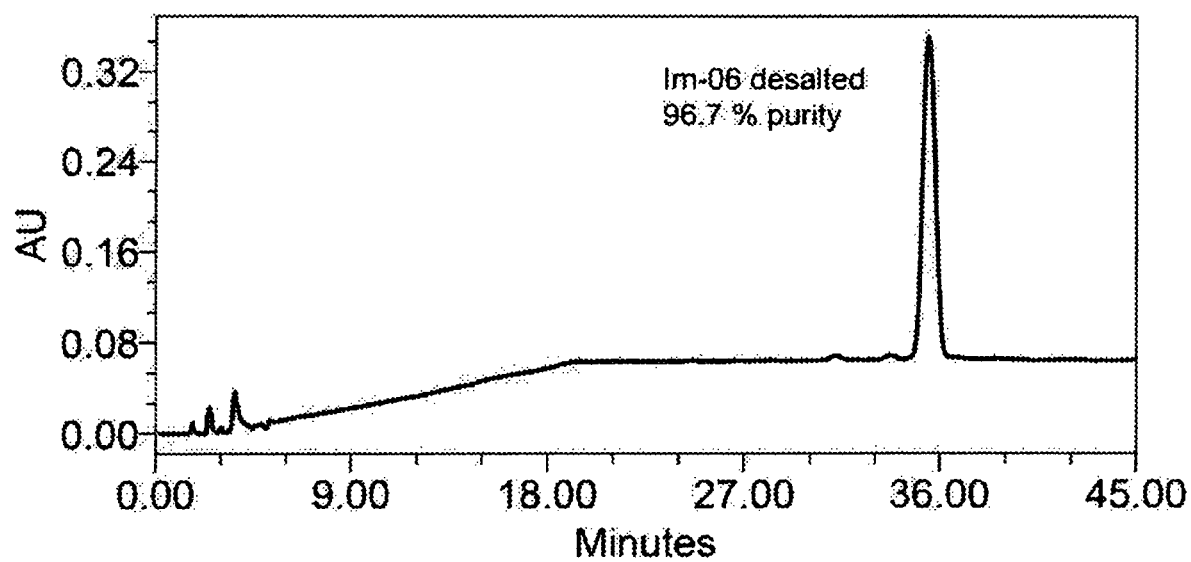
FIG. 14 shows the HPLC profile of intermediate Im-06 after HCl salt formation and desaltification. As can be seen, purity of the Im-06 after the HCl salt formation and desaltification improved to 96.7%.

Step 2: Free Salt Formation of Int-06.HCl or Im-06.HNO$_3$:

To a mixture of Im-06.HCl or Im-06.HNO$_3$ (100 mg) in EtOAc (10 ml) was added NaHCO$_3$ (2 mL, aqueous saturated). The mixture was stirred 10 min then separated. The organic layer was dried over Na$_2$SO$_4$ and concentrated to afford Im-06 (70-80 mg, 80-90% yield, HPLC purity at 210 nm for Im-06 recovered from HO salt is 96.7%, FIG. 14) as a colorless oil.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

Example 11: Improved Synthesis of Im-07

The synthesis of Im-07 was implemented with some minor modifications related to the work-up from the previously describe procedure. As shown in Scheme 9, LiOH is added until complete conversion is achieved (about 2.1 eq are needed). Work up was performed without extraction with dichloromethane and a clear product was obtained.

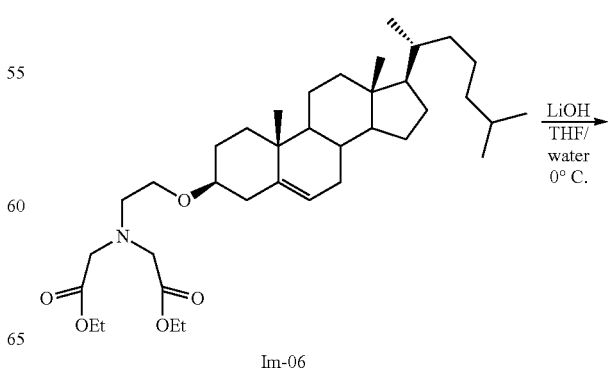

Scheme 9

-continued

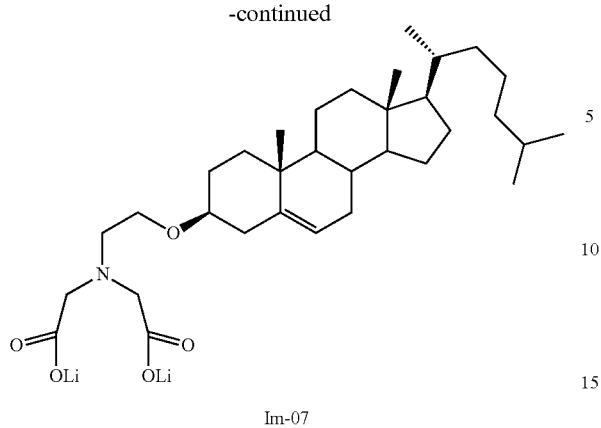

Im-07

Example 12: Synthesis of Compound 25

The goal of this study was to produce Compound 25 (COMP 25) suitable for toxicological studies, with purity near to 97% but without column chromatography. For this reason, in addition to the crystallization, some activities aimed to facilitate the isolation were carried out. In the initial trials, the two solutions Im-07 and Im-08 were mixed together according to the procedure and a precipitate was immediately formed. (Scheme 10)

Scheme 10

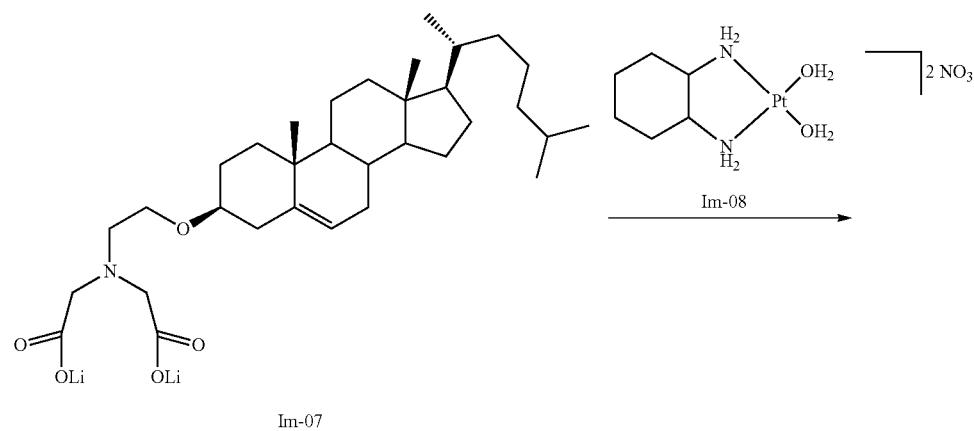

Im-07

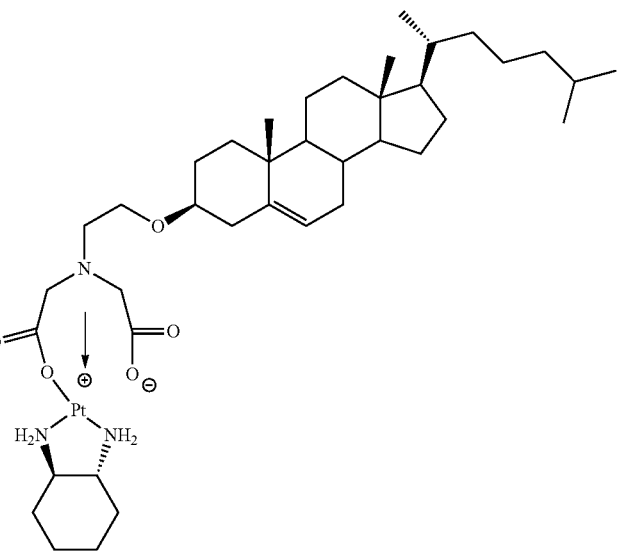

Comp 25

However, the filtration was not efficient because no solid remained on the filter. For this reason, in the final trials water was removed to obtain residue. The isolated product was then crystallized in DCM/methanol and slurried in a mixture of water/acetone. Crude contained high amounts of $NO_3$ (about 11%) before crystallization. This was easily explained by the fact that the product was isolated without washing and the amount of water in the reaction was not sufficient to remove them. Two slurries were done and nitrates were reduced. The purity of the final API was about 97%. Table 9 shows the gradual purification steps of crude Compound 25.

TABLE 9

Analytical results of stepwise purification of Compound 25

| | |
|---|---|
| Comp 25 after water removal | Comp 25: 85.2%<br>$NO_3$: 11.2% |
| Crystallization in EtOH/DCM | Comp 25: 89.4%<br>$NO_3$: 7.6% |
| 1° slurry | Comp 25: 95.8%<br>$NO_3$: 0.99% |
| 2° slurry | Comp 25: 96.7%<br>$NO_3$: 0.45% |

Reactions done with maximum 20 g Im-06 and 97% Compound 25 obtained in 57% yield. Reaction procedure can be comfortably implemented in KG scale. HPLC chromatogram of Compound 25 after crystallization and after two slurries is shown in FIG. 15 and peak results of FIG. 15 are shown in Table 10.

TABLE 10

Figure 15:
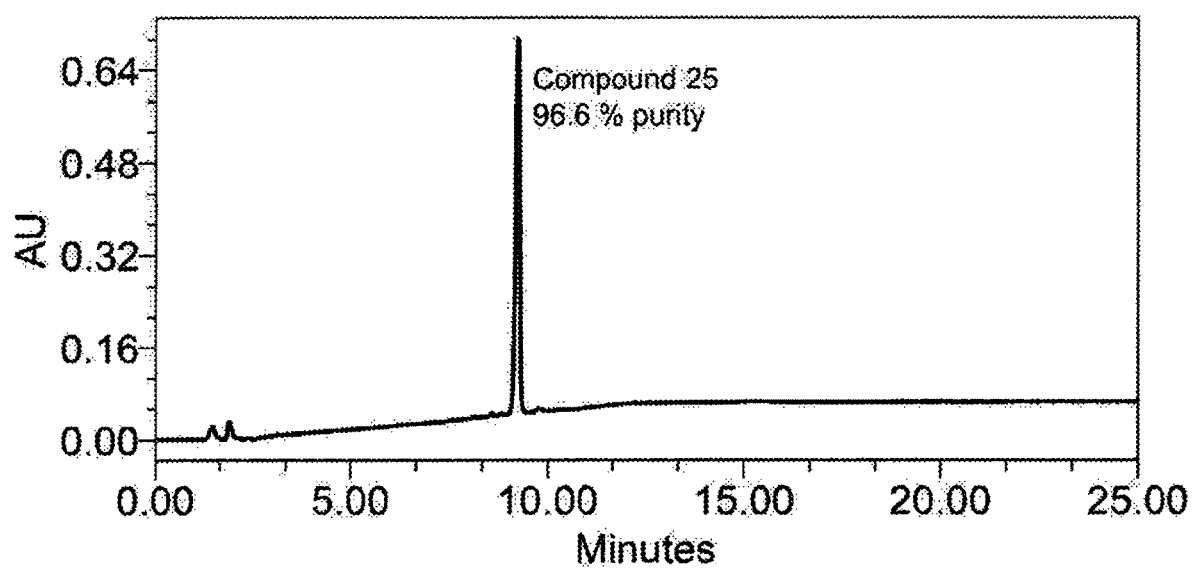
FIG. 15 shows the HPLC profile of Compound 25 after crystallization and after two slurries.

Peak results of FIG. 15
Peak Results

| | Name | RT | Area | Height | USP Tailing | USP Resolution | USP s/n | % Area |
|---|---|---|---|---|---|---|---|---|
| 1 | NO2 | 0.931 | 47301 | 6,723 | 1.5 | — | 40 | 0.45 |
| 2 | — | 1.894 | — | — | — | — | — | — |
| 3 | — | 8.546 | 16296 | 2418 | — | — | 14 | 0.15 |
| 4 | — | 8.744 | 47301 | 6567 | — | — | 41 | 0.45 |
| 5 | — | 8.845 | 29165 | 3696 | — | — | 23 | 0.25 |
| 6 | — | 8.922 | 5800 | 1450 | — | — | 8 | 0.06 |
| 7 | — | 9.115 | 62274 | 10406 | — | — | 62 | 0.59 |
| 8 | — | 9.304 | 31256 | 5078 | — | 1.1 | 30 | 0.30 |
| 9 | Comp 25 | 9.638 | 10184145 | 1299096 | 1.1 | 1.7 | 7387 | 96.7 |
| 10 | — | 10.345 | 108189 | 8962 | 1.1 | 2.5 | 54 | 1.03 |

Example 13. Crystallization of Compound 25

To improve the purity of Compound 25, a set of conditions were identified which resulted in the crystallisation of Compound 25 (COMP 25) and offered a clear purity uplift. During this work program, a number of amorphous solids were observed from a variety of solvent systems. PXRD and PLM analysis shows that the solid obtained during some of the crystallization studies were crystalline in nature Sequential steps for the analysis of the crude sample (e.g., Example 12, purity 94%) are as follows:
1) Crystallisation Screening on Crude comp 25 with selected solvents (20 mg trial)
2) Seeded Cooling Crystallisation of Crude COMP 25 (20 mg trial)
3) Cooling Crystallisation of Crude COMP 25 (20 mg trial)
4) Anti-Solvent/Cooling Crystallisation of Crude COMP 25 (20 mg and 50 mg trials)
5) Cooling Crystallisation of Crude COMP 25 (200-250 mg scale)
6) Seeded Cooling Crystallisation of Crude COMP 25 (250 mg trial)
7) Seeded, Anti-Solvent and Cooling Crystallisation of Crude COMP 25 (140-150 mg trial)

Initially a series of solvents and mixture of solvents were screened to select suitable solvents for the crystallization procedure. As shown in Table 11, mixture of alcohols such as 20 methanol/ethanol and chloroform/dichloromethane are suitable solvent mixtures for the crystallization procedure.

TABLE 11

Summary of Comp 25 solubility data in pure solvents and mixtures

| Solvent or Mixture of solvents | Approximate solubility | XRPD Analysis of material after temperature cycling |
| --- | --- | --- |
| 1,4-dioxane | ≤10 mg/ml | |
| 1-butanol | ≤10 mg/ml | |
| 1-propanol | ≤30 mg/ml | |
| 2-butanol | ≤10 mg/ml | |
| 2-methyl ethanol | ≤10 mg/ml | |
| 2-methyl THF | ≤10 mg/ml | |
| Acetone | ≤10 mg/ml | |
| acetonitrile | ≤10 mg/ml | |
| Anisole | ≤10 mg/ml | |
| Chloroform | ≤100 mg/ml | |
| Dichloromethane | ≤100 mg/ml | |
| Dimethylacetamide | ≤10 mg/ml | |
| Dimethylformamide | ≤10 mg/ml | |
| Dimethyl sulfoxide | ≤10 mg/ml | |
| Absolute Ethanol | ≤15 mg/ml | |
| Ethyl acetate | ≤10 mg/ml | |
| Ethylene glycol | ≤10 mg/ml | |
| Heptanes | ≤10 mg/ml | |
| Propane-2-ol | ≤10 mg/ml | |
| Methanol | ≤10 mg/ml | |
| Tert butyl methyl ether | ≤10 mg/ml | |
| Tetrahydrofuran | ≤10 mg/ml | |
| Toluene | ≤10 mg/ml | |
| Water | ≤10 mg/ml | |
| Methanol:Chloroform (50:50 v/v %) | ≤200 mg/ml | Crystalline |
| Methanol:Dichloromethane (50:50 v/v %) | ≤200 mg/ml | Crystalline |
| Ethanol:Chloroform (50:50 v/v %) | ≤200 mg/ml | Crystalline |
| Ethanol:Dichloromethane (50:50 v/v %) | ≤200 mg/ml | Crystalline |
| Methanol:Dichloromethane (90:10 v/v %) | ≤80 mg/ml | Crystalline |
| Ethanol:Dichloromethane (90:10 v/v %) | ≤80 mg/ml | Crystalline |
| Methanol:Dichloromethane (80:20 v/v %) | ≤200 mg/ml | Crystalline |
| Methanol:Dichloromethane (70:30 v/v %) | ≤200 mg/ml | Crystalline |
| Methanol:Dichloromethane (60:40 v/v %) | ≤200 mg/ml | Crystalline |
| Methanol:Dichloromethane (40:60 v/v %) | ≤200 mg/ml | Crystalline |
| Methanol:Dichloromethane (30:70 v/v %) | ≤200 mg/ml | Crystalline |
| Methanol:Dichloromethane (20:80 v/v %) | ≤200 mg/ml | Crystalline |
| Methanol:Dichloromethane (10:90 v/v %) | ≤200 mg/ml | Crystalline |
| Ethanol:Dichloromethane (80:20 v/v %) | ≤80 mg/ml | |
| Ethanol:Dichloromethane (70:30 v/v %) | ≤200 mg/ml | |
| Ethanol:Dichloromethane (60:40 v/v %) | ≤200 mg/ml | |
| Ethanol:Dichloromethane (40:60 v/v %) | ≤200 mg/ml | Crystalline |
| Ethanol:Dichloromethane (30:70 v/v %) | ≤200 mg/ml | Crystalline |
| Ethanol:Dichloromethane (20:80 v/v %) | ≤200 mg/ml | Crystalline |
| Ethanol:Dichloromethane (10:90 v/v %) | ≤200 mg/ml | Crystalline |

Figure 16:
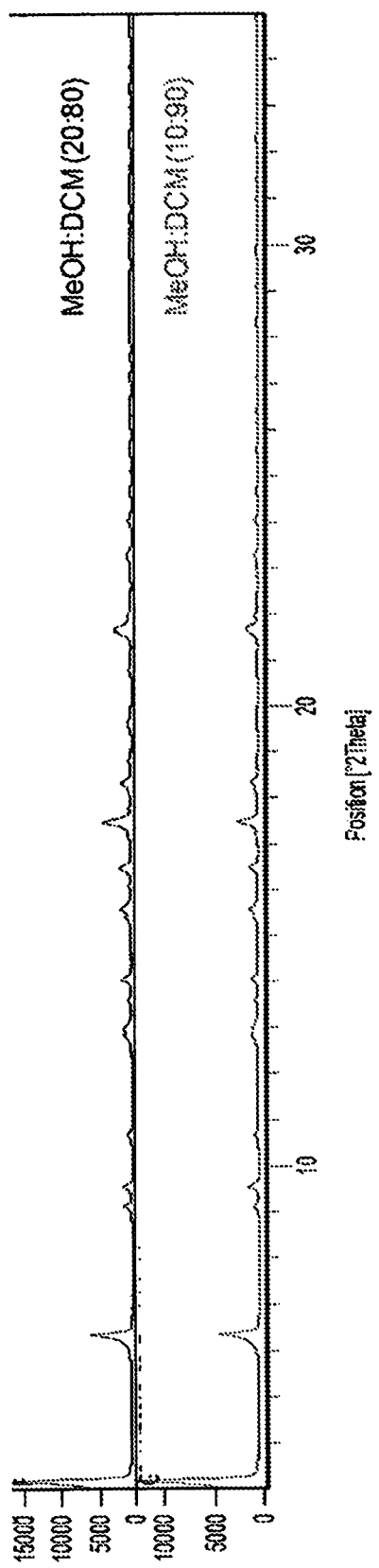
FIG. 16 shows the XRPD 2θ diffractograms of solids recovered from successful crystallisation screening of crude COMP 25.

Crystallisation Screening on Crude Compound 25 on Selected Solvents:

Crystallisation screening on crude compound 25 (COMP 25) was carried out using Methanol:Dichloromethane and Ethanol:Dichloromethane solvent mixtures. The material isolated from each experiment after temperature cycling was analysed by XRPD and the results are summarized in Table 12. Crystalline COMP 25 was obtained using methanol:dichloromethane (20:80% v/v) and (10:90% v/v) solvent systems. All other methanol:dichloromethane and ethanol:dichloromethane solvent mixtures produced amorphous material. XRPD 2θ diffractograms of solids recovered from successful crystallisation screening of crude COMP 25 are shown in FIG. 16.

TABLE 12

Crystallization Screening on Crude COMP 25

| Solvent System (% v/v) | Isolated material |
| --- | --- |
| Methanol:Dichloromethane (90:10) | Amorphous |
| Methanol:Dichloromethane (80:20) | Amorphous |
| Methanol:Dichloromethane (70:30) | Amorphous |
| Methanol:Dichloromethane (60:40) | Amorphous |
| Methanol:Dichloromethane (50:50) | Amorphous |
| Methanol:Dichloromethane (40:60) | Amorphous |
| Methanol:Dichloromethane (30:70) | Amorphous |
| Methanol:Dichloromethane (20:80) | Crystalline |
| Methanol:Dichloromethane (10:90) | Crystalline |
| Ethanol:Dichloromethane (90:10) | Amorphous |
| Ethanol:Dichloromethane (80:20) | Amorphous |
| Ethanol:Dichloromethane (70:30) | Amorphous |
| Ethanol:Dichloromethane (60:40) | Amorphous |
| Ethanol:Dichloromethane (50:50) | Amorphous |
| Ethanol:Dichloromethane (40:60) | Amorphous |
| Ethanol:Dichloromethane (30:70) | Amorphous |
| Ethanol:Dichloromethane (20:80) | Amorphous |
| Ethanol:Dichloromethane (10:90) | Amorphous |

Seeded Cooling Crystallization of Crude COMP 25

General Procedure:

Approximately 20 mg of Crude COMP 25 was weighed into a 2 ml glass vial and 100 NL of respective solvent system was added to the experiments at ca. 25° C. All solvents were dried over pre-dried 3 A molecular sieves (where appropriate) prior to use. Small amount of crystalline COMP 25 was added as a seed to the experiments. The experiments were heated to 40° C. The experiments were cooled down to 5° C. at ca. 0.11° C./minute. The experiments were stirred at 5° C. for 3 hours and temperature cycled between 5° C. to 40° C. at 0.2° C./minute overnight (ca. 18 hours). The experiments where solid material was observed, the solids were isolated using centrifuge at ambient (ca. 22° C.) and analysed by XRPD. Table 13 summarizes the solvent systems used for seeded, cooling crystallisation of crude COMP 25.

TABLE 13

Solvent systems used for seeded, cooling crystallization of crude COMP 25

| Solvent System | (% v/v) |
| --- | --- |
| Methanol:Dichloromethane | (30:70) |
| Methanol:Dichloromethane | (20:80) |
| Methanol:Dichloromethane | (10:90) |
| Ethanol:Dichloromethane | (30:70) |
| Ethanol:Dichloromethane | (20:80) |
| Ethanol:Dichloromethane | (10:90) |

Figure 17:
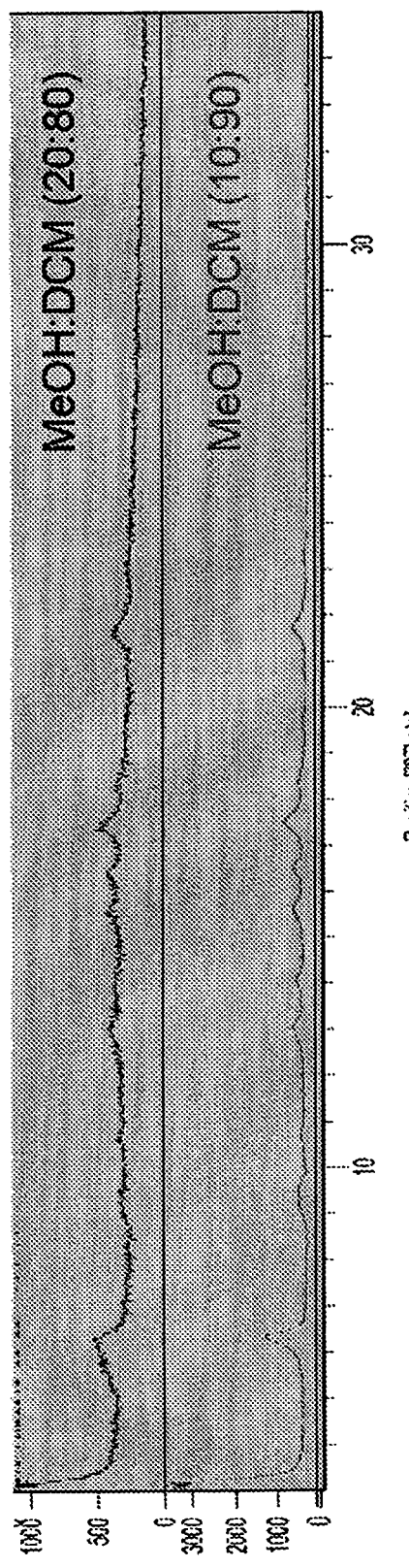
FIG. 17 shows XRPD 2θ diffractograms on solids after temperature cycling.
Figure 18:
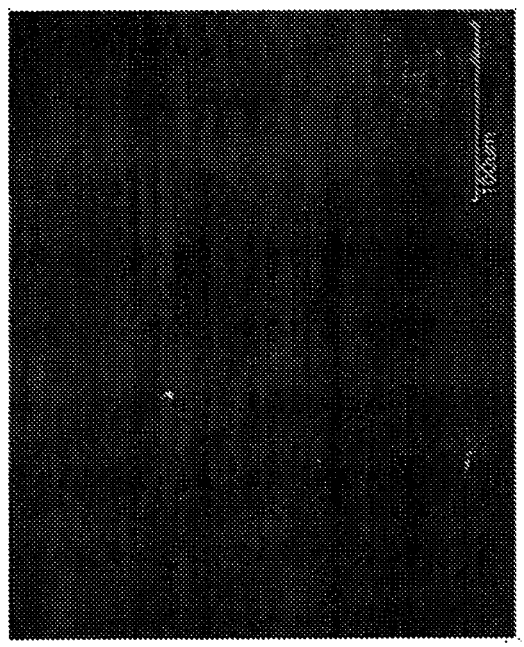
FIG. 18 shows PLM micrographs of crystalline material obtained from seeded methanol:dichloromethane (10:90% v/v).
Figure 18:
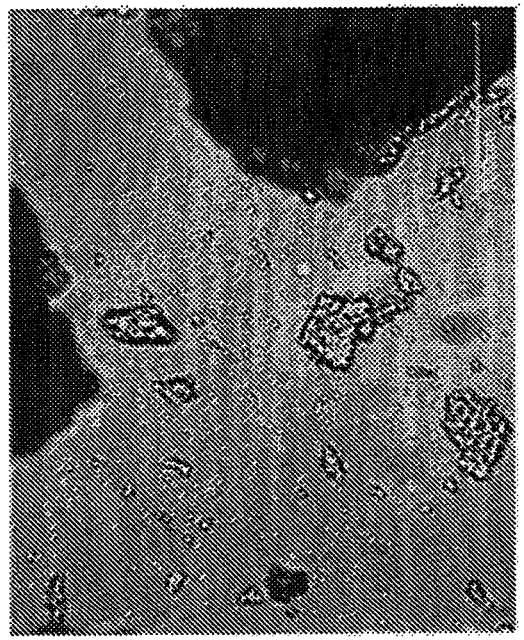

The only experimental conditions that returned the reoccurring crystalline form was methanol:dichloromethane (10:90% v/v). Methanol:dichloromethane (20:90% ov/v) returned weakly crystalline material. All Ethanol:Dichloromethane mixtures and methanol:dichloromethane (30:70% v/v) returned amorphous material. FIG. 17 shows XRPD 2θ diffractograms on solids after temperature cycling and FIG. 18 shows PLM micrographs of crystalline material obtained from seeded methanol:dichloromethane (10:90% v/v).

Cooling Crystallization of Crude COMP 25 (20 mg trial)

General Procedure:

Crude COMP 25 was weighed into a 2 mL sample vial and a known aliquot of solvent added at ca. 25° C. Stirred at 25° C. Cooled down from 25° C. to 5° C. at ca. 0.11° C./minute. Stirred at 5° C. for 3 hours. Temperature cycled between 5° C. to 40° C. at ca. 0.2° C./minutes. The experiments where solid material was observed, the solids were isolated at 25° C. using centrifuge and analysed by XRPD.

Figure 19:
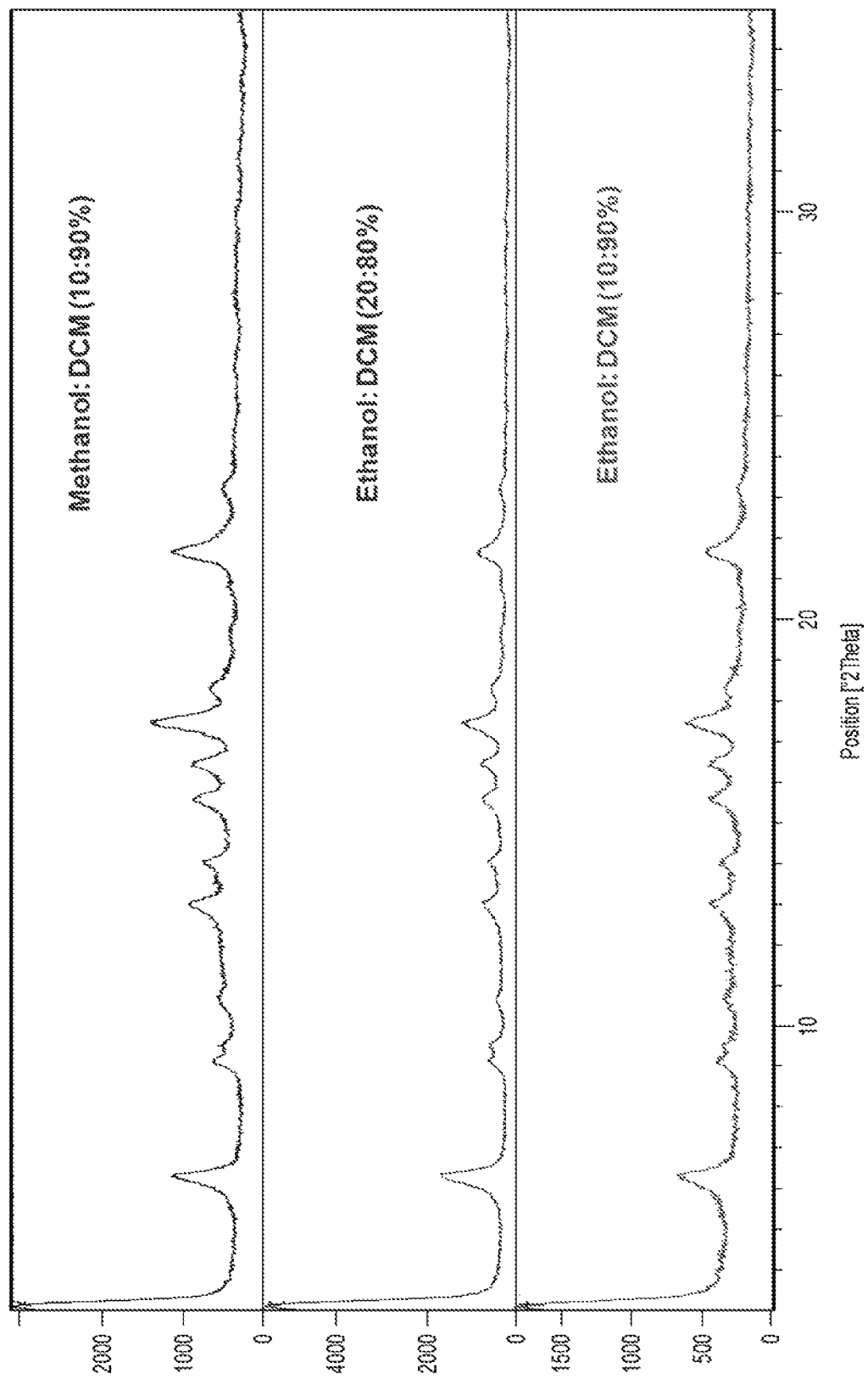
FIG. 19 shows XRPD 2θ diffractograms of Solids after temperature cycling at Concentration ca. 150 mg/ml.

Table 14 summarizes the conditions used for cooling crystallization and Table 15 summarizes the conditions for cooling crystallisation in double scale. Tables 16 and 17 summarize the results and observations for the cooling crystallization studies. XRPD 2θ diffractograms of exemplary solids after temperature cycling at concentration ca 150 mg/ml are shown in FIG. 19.

TABLE 14

Conditions for cooling crystallization

| Solvent system (% v/v) | Volume of solvent (μL) | Mass of crude IO-125 (mg) | Concentration (mg/mL) |
| --- | --- | --- | --- |
| Methanol:Dichloromethane (40:60) | 150 | 20.49 | 136.6 |
| Methanol:Dichloromethane (30:70) | 150 | 18.69 | 124.6 |
| Methanol:Dichloromethane (20:80) | 150 | 20.31 | 135.4 |
| Methanol:Dichloromethane (10:90) | 150 | 20.23 | 134.87 |
| Ethanol:Dichloromethane (40:60) | 150 | 20.56 | 137.07 |
| Ethanol:Dichloromethane (30:70) | 150 | 20.33 | 135.53 |
| Ethanol:Dichloromethane (20:80) | 150 | 19.46 | 129.73 |
| Ethanol:Dichloromethane (10:90) | 150 | 19.51 | 130.07 |

TABLE 15

Conditions for cooling crystallisation in double scale

| Solvent system (% v/v) | Volume of solvent (μL) | Mass of crude IO-125 (mg) | Concentration (mg/mL) |
| --- | --- | --- | --- |
| Methanol:Dichloromethane (23:80) | 333 | 49.38 | 148.29 |
| Methanol:Dichloromethane (10:90) | 333 | 50.13 | 150.54 |
| Ethanol:Dichloromethane (20:80) | 333 | 50.73 | 152.34 |
| Ethanol:Dichloromethane (10:90) | 333 | 49.84 | 149.67 |

TABLE 16

Summary of results and observations for the cooling crystallizations

| Solvent system (% v/v) | Concentration (mg/mL) | Observations After temperature cycling | XRPD Analysis Results |
| --- | --- | --- | --- |
| Methanol:Dichloromethane (40:60%) | 136.6 | Clear Solution, No precipitation | No Precipitation |
| Methanol:Dichloromethane (30:70%) | 124.6 | Clear Solution, No precipitation | No Precipitation |
| Methanol:Dichloromethane (20:80%) | 135.4 | Clear Solution, No precipitation | No Precipitation |
| Methanol:Dichloromethane (10:90%) | 134.87 | White Slurry | Crystalline |
| Ethanol:Dichloromethane (40:60%) | 137.07 | Clear Solution, No precipitation | No Precipitation |
| Ethanol:Dichloromethane (30:70%) | 135.53 | Clear Solution, No precipitation | No Precipitation |
| Ethanol:Dichloromethane (20:80%) | 129.73 | White Solid | Crystalline |
| Ethanol:Dichloromethane (10:90%) | 130.07 | White Solid | Crystalline |

TABLE 17

Summary of results and observations for the cooling crystallizations

| Solvent system (% v/v) | Concentration (mg/mL) | Observation After temperature cycling | XRPD Analysis Results |
|---|---|---|---|
| Methanol:Dichloromethane (20:80%) | 148.29 | Clear Solution, No precipitation | No Precipitation |
| Methanol:Dichloromethane (00:90%) | 150.54 | White Slurry | Crystalline |
| Methanol:Dichloromethane (20:80%) | 152.34 | White Solid | Crystalline |
| Methanol:Dichloromethane (10:90%) | 149.67 | White Solid | Crystalline |

Anti-Solvent/Cooling Crystallization of Crude COMP 25

Figure 20:
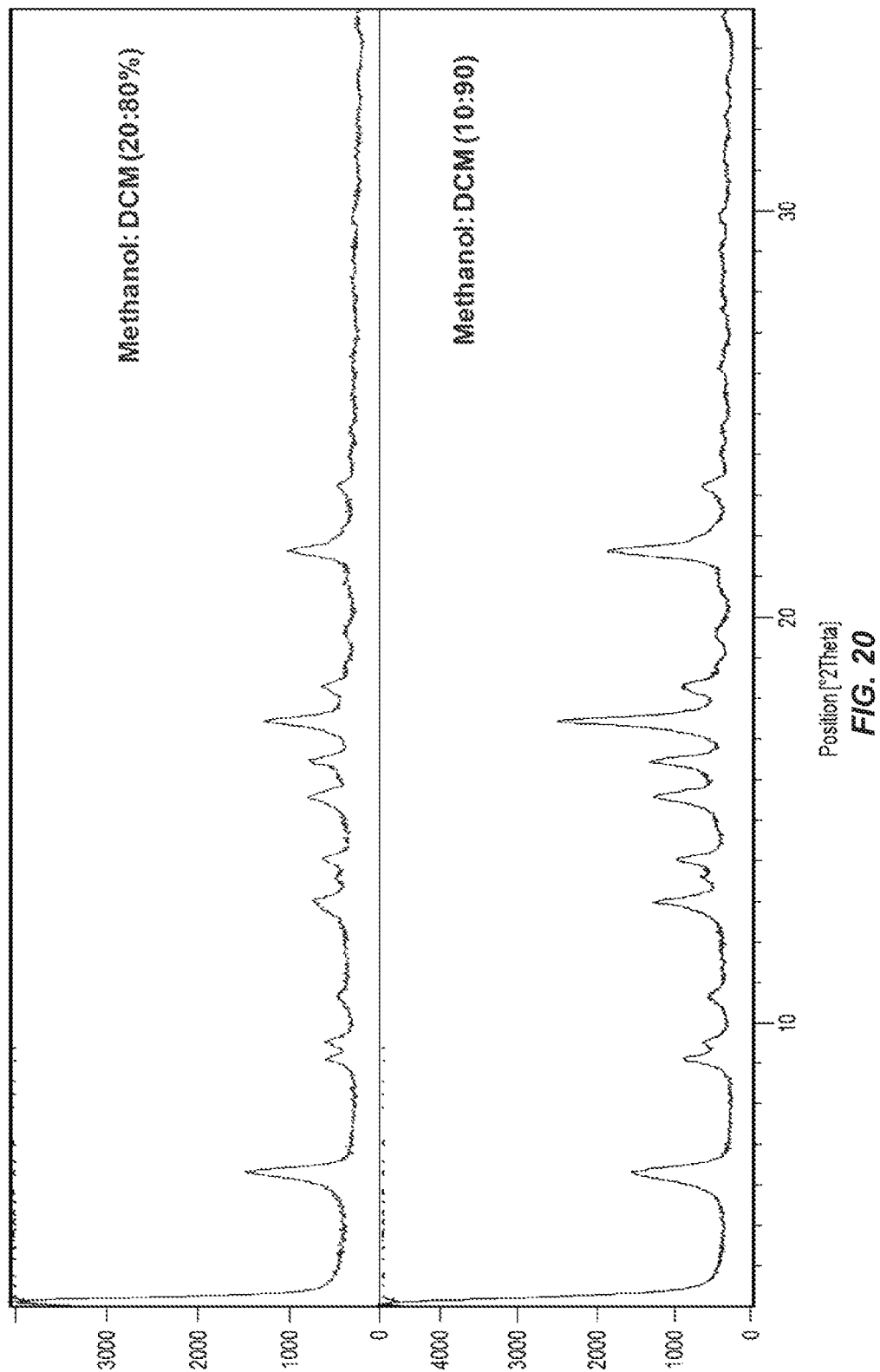
FIGS. 20 and 21 show XRPD 2θ diffractograms of solids after temperature cycling, heptanes used as the anti-solvent.
Figure 21:
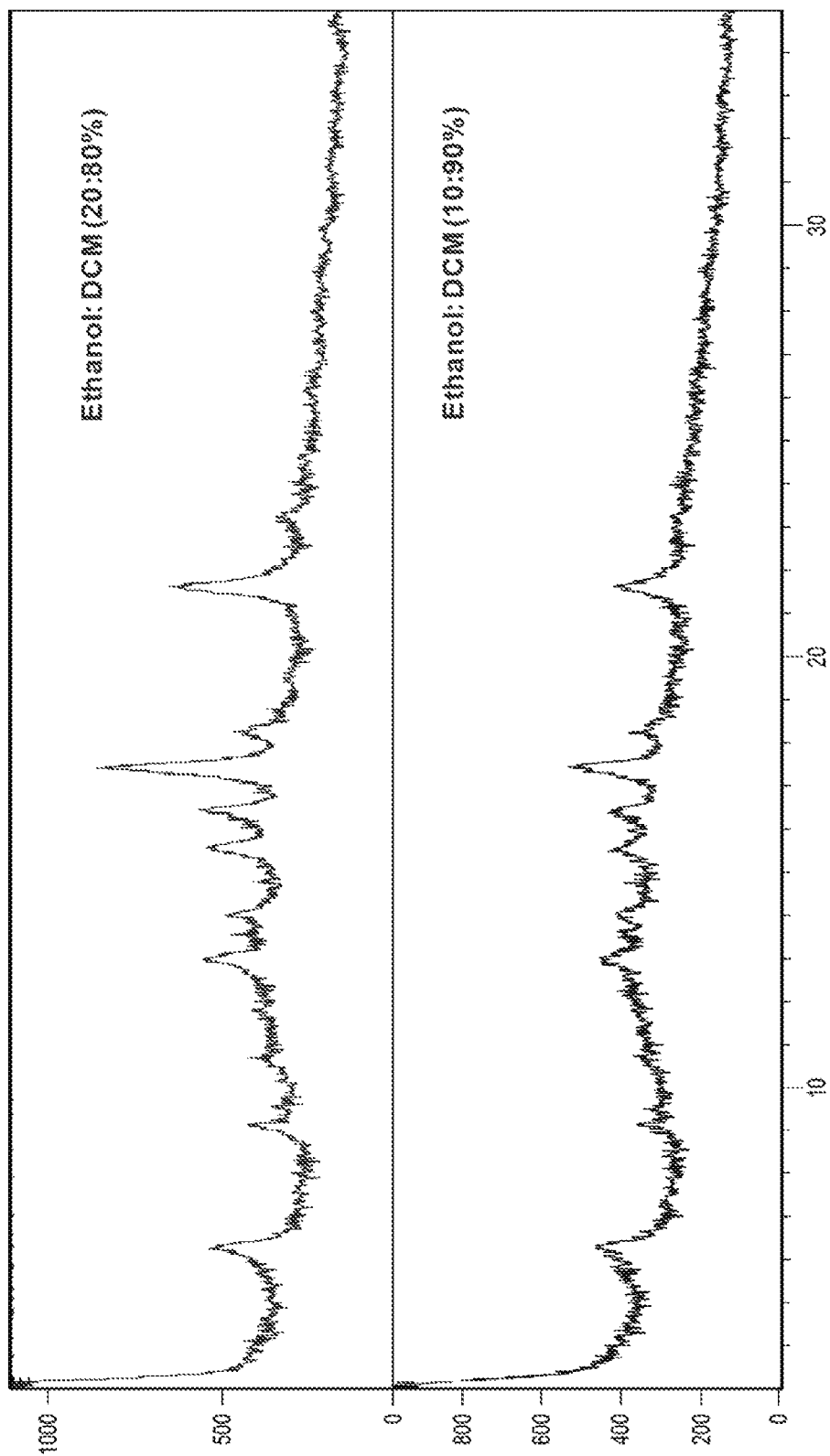

General Procedure:

Approximately 50 mg COMP 25 Crude was weighed into a 2 mL sample vial and appropriate volume of respective solvent was added at ca. 25° C. Respective anti-solvent was added to appropriate vial in 25NL aliquots at ca. 25° C. The experiments were cooled down from 25° C. to 5° C. at ca. 0.11° C./minute. Stirred at 5° C. for 3 hours. The experiments were temperature cycled between 5° C. to 40° C. at ca. 0.2° C./minute overnight (ca. 18 hours). The experiments where thin slurry or clear solution were observed further anti-solvent was added to the experiments at ca. 25° C. The experiments were cooled down from 25° C. to 5° C. at ca. 0.11° C./minute. Stirred at 5° C. for 3 hours. The experiments were temperature cycled overnight between 5° C. to 40° C. at ca. 0.2° C./minute overnight (ca. 18 hours). The experiments where solid material was observed, the solids were isolated at ambient (ca. 22° C.) using centrifuge and analysed by XRPD. Samples that were isolated were then dried under vacuum at ambient temperature overnight Using 2-methyl THF as an anti-solvent the crystallisation were resulted in formation of gel like material using methanol:dichloromethane solvent mixtures and ethanol:dichloromethane (30:70% v/v) solvent system. Using heptane as an anti-solvent crystalline material was observed using most of the solvent systems. As shown in Tables 18 and 19, using acetonitrile as an anti-solvent partially crystalline material was observed using most of the solvent systems. XRPD 2θ diffractograms of solids after temperature cycling, and-solvent used heptanes are shown in FIGS. 20 and 21.

TABLE 18

Observations and results for anti-solvent addition/cooling crystallizations

| Solvent system (% v/v) | Anti-Solvent | Concentration (mg/mL) | Observations | Observations after overnight temperature cycling | Observations after further temperature cycling | XRPD Analysis Results |
|---|---|---|---|---|---|---|
| Methanol:Dichloromethane (30:70) | Heptane | 198.9 | Clear Solution | White Slurry | Slurry | Crystalline |
| Methanol:Dichloromethane (20:80) | | 192.2 | Clear Solution | Thick White Slurry | Thick slurry | Crystalline |
| Methanol:Dichloromethane (10:90) | | 232.3 | Clear Solution | Thick White Slurry | Thick slurry | Crystalline |
| Methanol:Dichloromethane (30:70) | Acetonitrile | 109.14 | Thick precipitation further 75 μL of solvent system added to make thin slurry | Some Precipitation | Slurry | Partially crystalline |
| Methanol:Dichloromethane (20:80) | | 110.74 | Thick precipitation further 75 μL of solvent system added to make thin slurry | Some Precipitation | Shiny | Partially crystalline |
| Methanol:Dichloromethane (10:90) | | 184.55 | Thick precipitation further 100 μL of solvent system added to make thin slurry | Some Precipitation | Slurry | Partially crystalline |
| Methanol:Dichloromethane (30:70) | 2-methyl THF | 200.1 | Clear Solution | Clear Solution, No precipitation | Gel Like | N/A |
| Methanol:Dichloromethane (20:80) | | 212.9 | Clear Solution | Clear Solution, No precipitation | Gel Like | N/A |
| Methanol:Dichloromethane (10:90) | | 205.8 | Clear Solution | Thick clear gel | Gel Like | N/A |

TABLE 19

Observations and results for anti-solvent addition/cooling crystallizations

| Solvent system (% v/v) | Anti-Solvent | Concentration (mg/mL) | Observations | Observations after overnight temperature cycling | Observations after further temperature cycling | XRPD Analysis Results |
|---|---|---|---|---|---|---|
| Ethanol:Dichloromethane (30:70) | | 198.8 | Clear Solution | White Slurry | Slurry | Crystalline |
| Ethanol:Dichloromethane (20:80) | Heptane | 208.6 | Clear Solution | Thick White Slurry | Slurry | Crystalline |
| Ethanol:Dichloromethane (10:90) | | 211.9 | Clear Solution | Clear Gel | Gel | N/A |
| Ethanol:Dichloromethane (30:70) | | 141.33 | Thick precipitation | Some Precipitation | Slurry | Partially crystalline |
| Ethanol:Dichloromethane (20:80) | Acetonitrile | 139.33 | Thick precipitation | White Slurry | Slurry | Partially crystalline |
| Ethanol:Dichloromethane (10:90) | | 106 | Thick precipitation | White Gum | Slurry | Partially crystalline |
| Ethanol:Dichloromethane (30:70) | 2-methyl THF | 196 | Clear Solution | Gel Like | Gel Like | N/A |

Cooling Crystallization of Crude COMP 25 (200-250 mg Scale)

Figure 22:
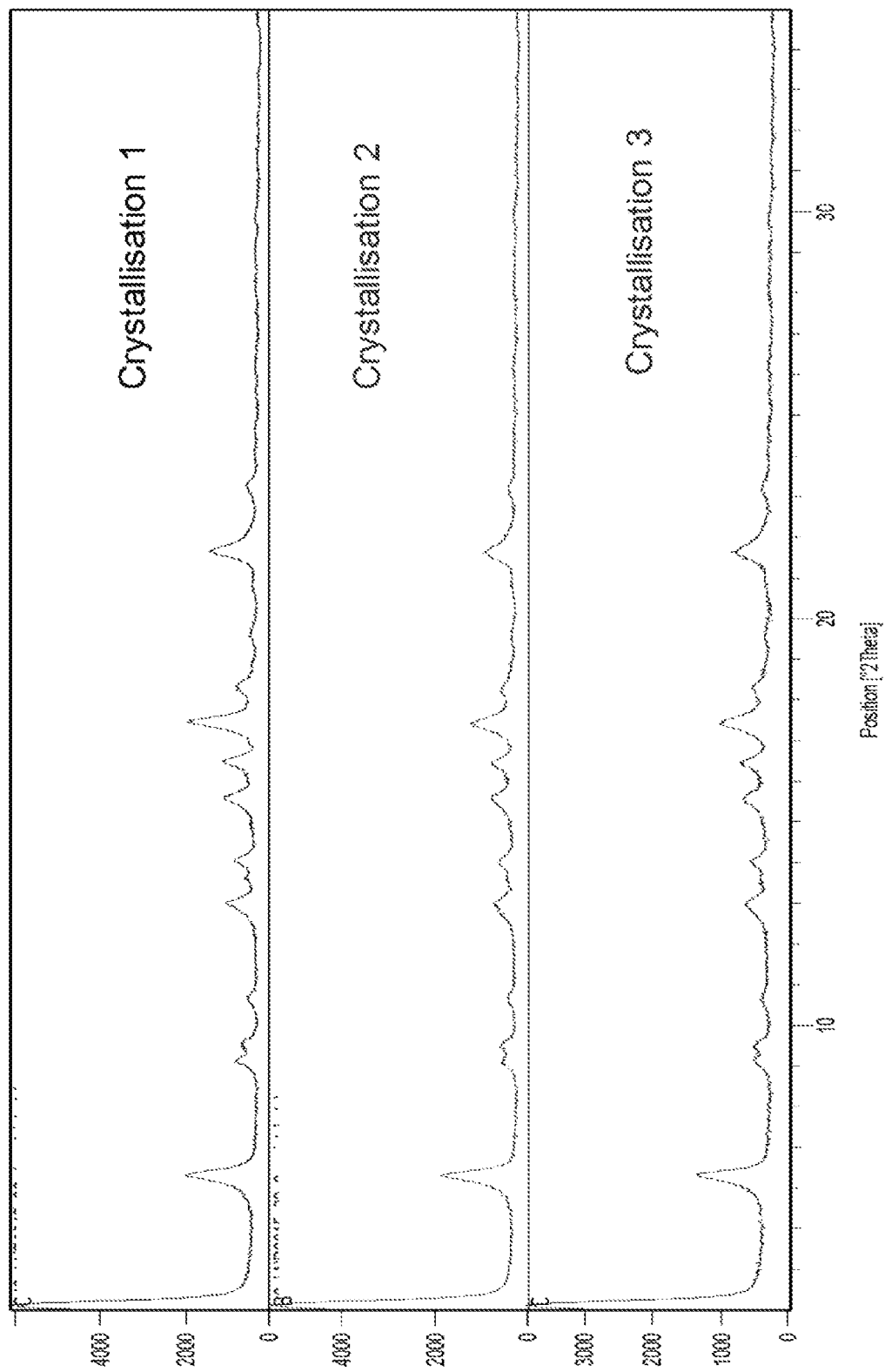
FIG. 22 shows XRPD 2θ diffractograms of cooling crystallization solids.
Figure 23:
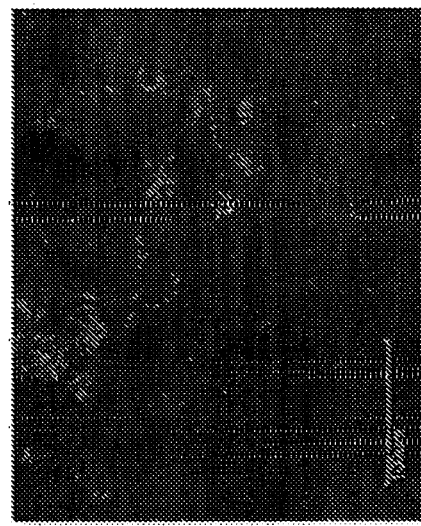
FIG. 23 shows PLM micrographs of dried solids.
Figure 23:
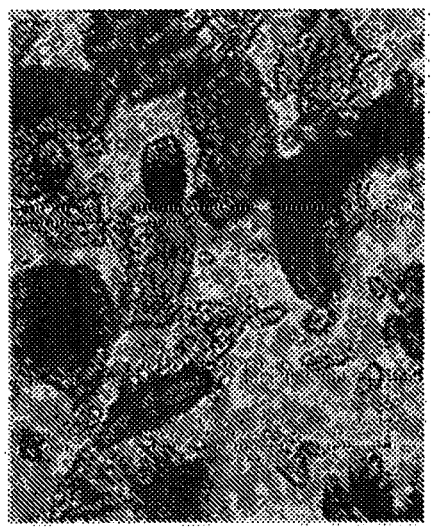
Figure 23:
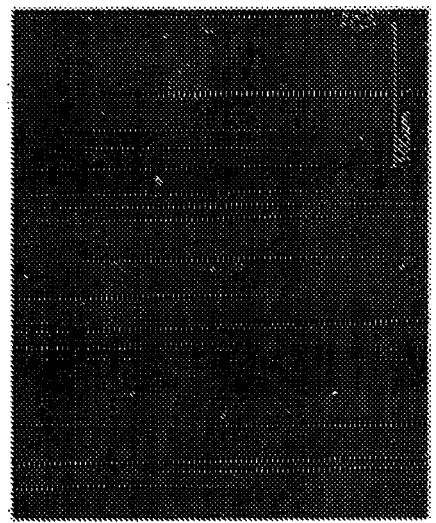
Figure 23:
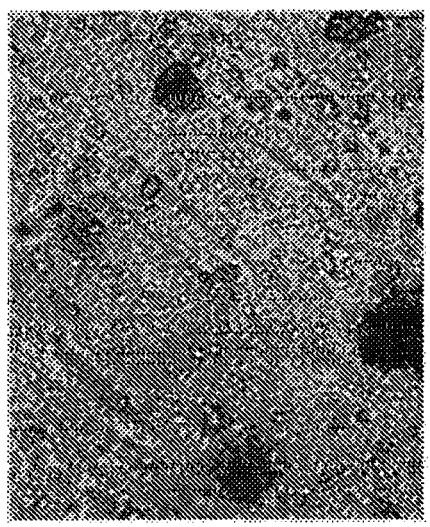
Figure 23:
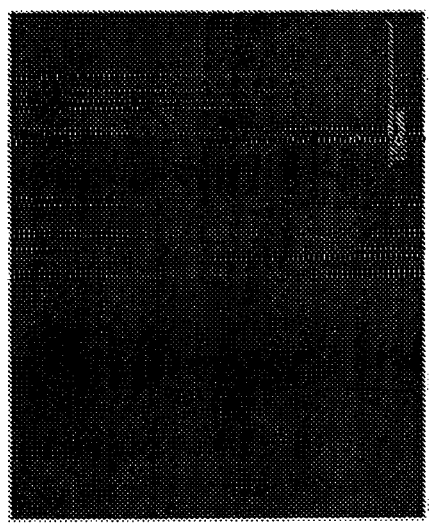
Figure 23:
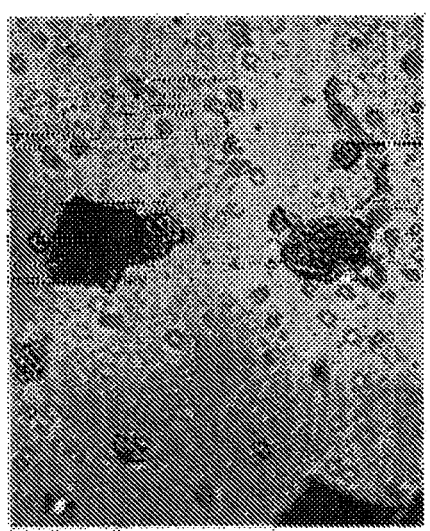
Figure 24:
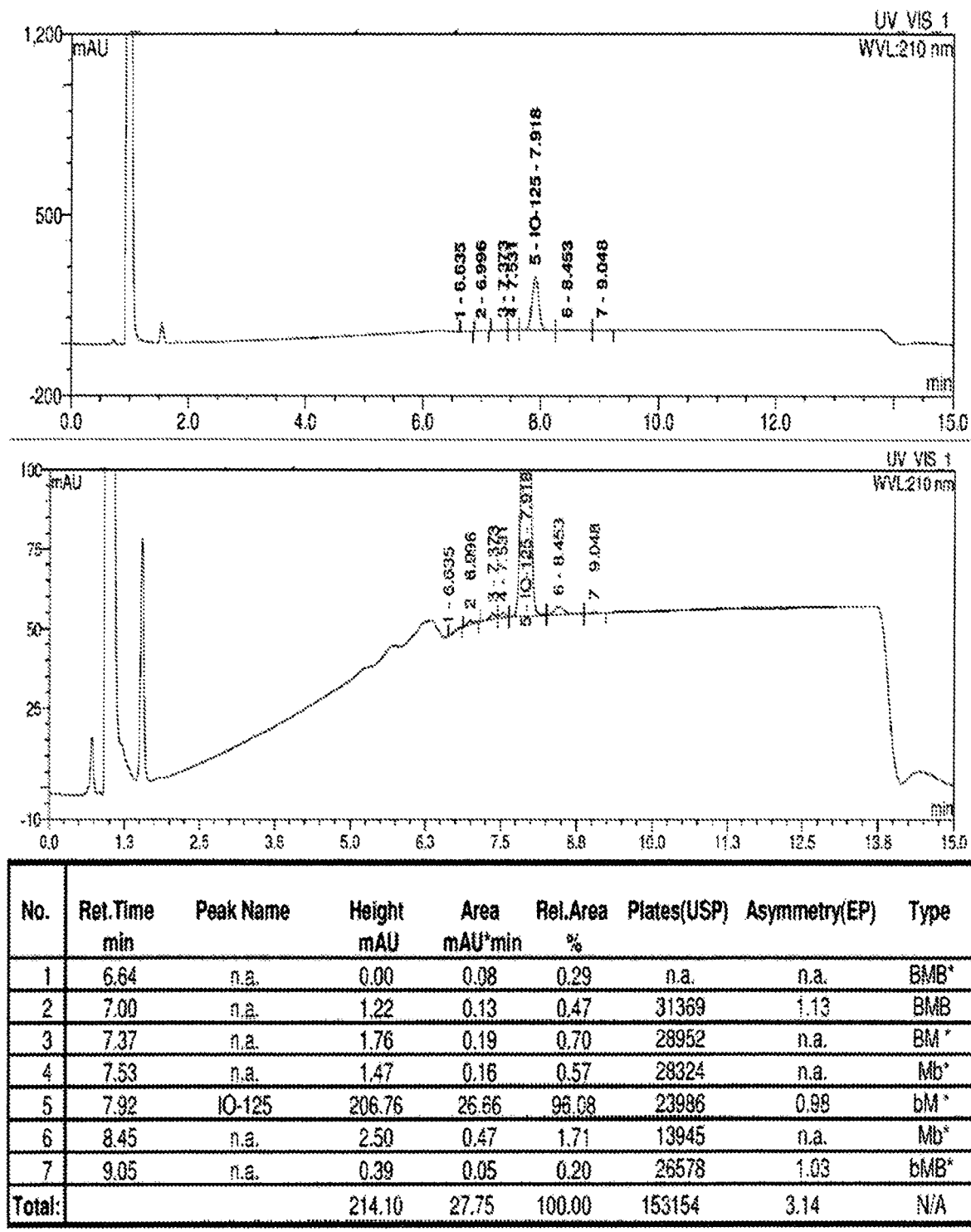
FIG. 24 is a HPLC chromatogram of cooling crystallization 2.

General Procedure:

Respective mass of COMP 25 Crude was weighed into a 20 mL sample vial and appropriate volume of respective solvent system was added at ca. 25° C. to dissolve the sample. The experiments were cooled down to 5° C. at ca. 0.1° C./min. Stirred at 5° C. for 2 hours. Temperature cycled between 5° C. to 40° C. Heated to 40° C. over 2 hours (ca. 0.3° C./minute). Stirred at 40° C. for 2 hours. Cooled down to 5° C. over 2 hours (ca. 0.3° C./minute). Stirred at 5° C. for 2 hours. Samples were isolated at ambient (ca. 22° C.) by filtering over Buchner funnel under vacuum using Whatmann filter paper No. 1, then dried under vacuum at ambient temperature overnight (approx. 18 hrs). The solid material was then analysed by XRPD and PLM. Results are summarized in Table 20 and shown in FIGS. 22 and 23. HPLC chromatogram of an exemplary cooling crystallization 2 is shown in FIG. 24.

TABLE 20

Observations and Results for cooling crystallization

| Solvent system (% v/v) | Concentration (mg/mL) | XRPD analysis | Isolated yield | HPLC purity | Crystallization Number |
|---|---|---|---|---|---|
| Methanol:Dichloromethane (20:80) | 250 | Crystalline | 30% | 93.98% | 1 |
| Methanol:Dichloromethane (10:90) | 250 | Crystalline | 51% | 96.08% | 2 |
| Methanol:Dichloromethane (10:90) | 200 | Crystalline | 20% | 95.04% | 3 |

Seeded Cooling Crystallization of Crude COMP 25 (250 mg Scale)

Figure 25:
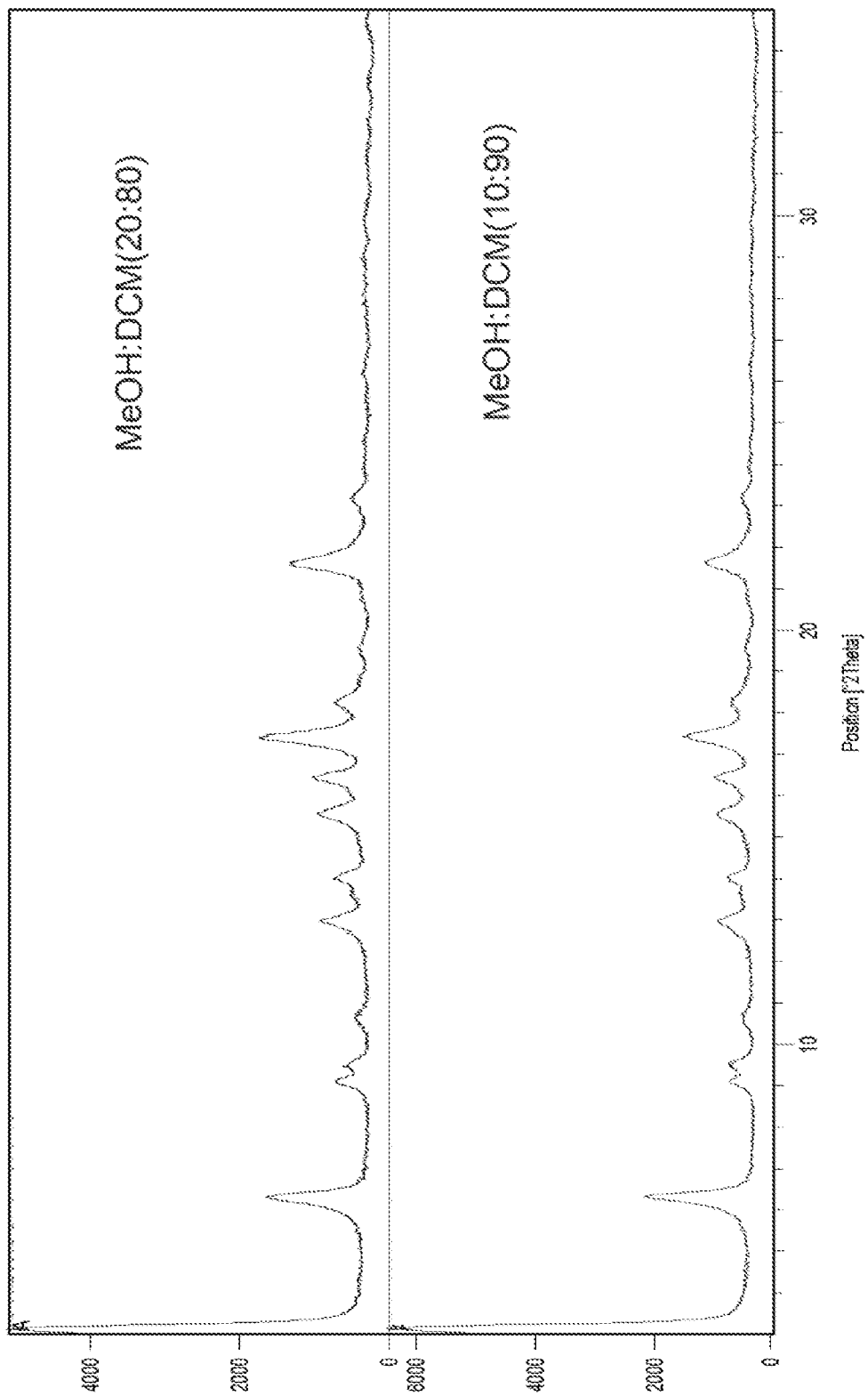
FIG. 25 shows XRPD 2θ diffractograms of dried solids.
Figure 26:
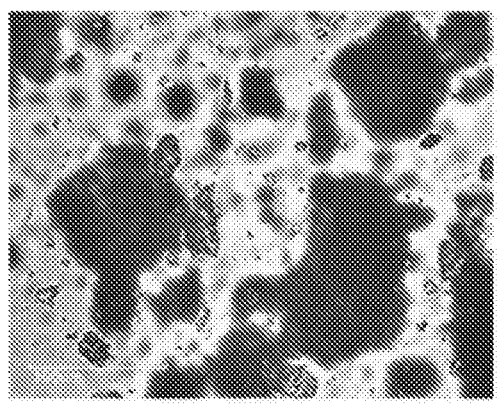
FIG. 26 shows PLM micrographs of dried solids.
Figure 26:
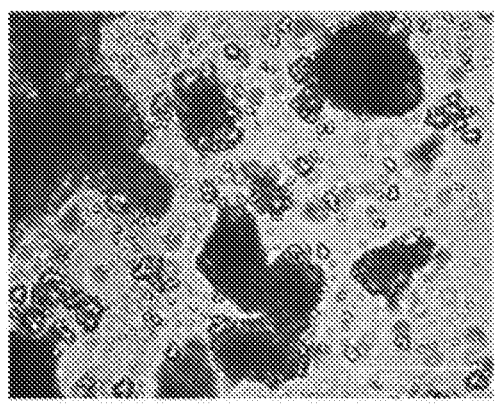
Figure 26:
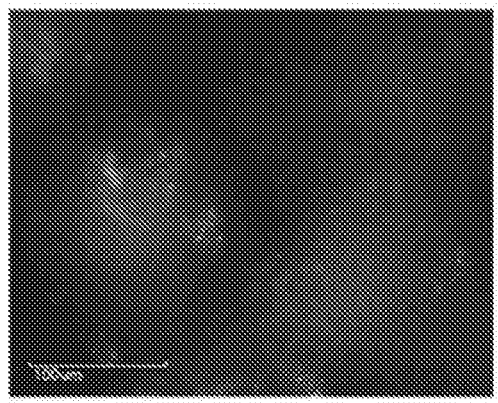
Figure 26:
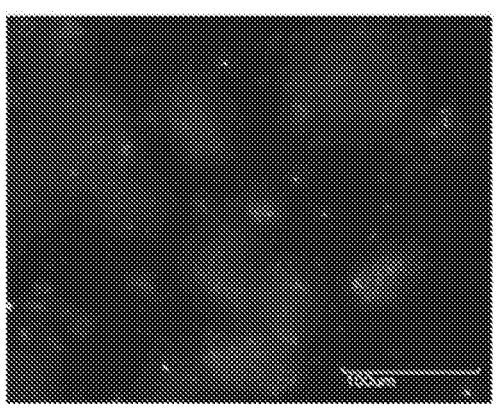

General Procedure:

Respective mass of Crude COMP 25 was weighed into a 20 mL sample vial and appropriate volume of respective solvent system was added at ca. 25° C. to dissolve the sample. Crystalline COMP 25 was added to the experiments as a seed. The experiments were cooled down to 5° C. at ca. 0.1° C./min. Stirred at 5° C. for 2 hours. Temperature cycled between 5° C. to 40° C. Heated to 40° C. over 2 hours (ca. 0.3° C./minute) Stirred at 40° C. for 2 hours. Cooled down to 5° C. over 2 hours (ca. 0.3° C./minute). Stirred at 5° C. for 2 hours. Samples were isolated at ambient (ca. 22° C.) by filtering over Buchner funnel under vacuum using Whatmann filter paper No. 1, then dried under vacuum at ambient temperature overnight (ca. 18 hours). The solid material was then analysed by XRPD and PLM. Results are summarized in Table 21 and shown in FIGS. 25 and 26.

Figure 27:
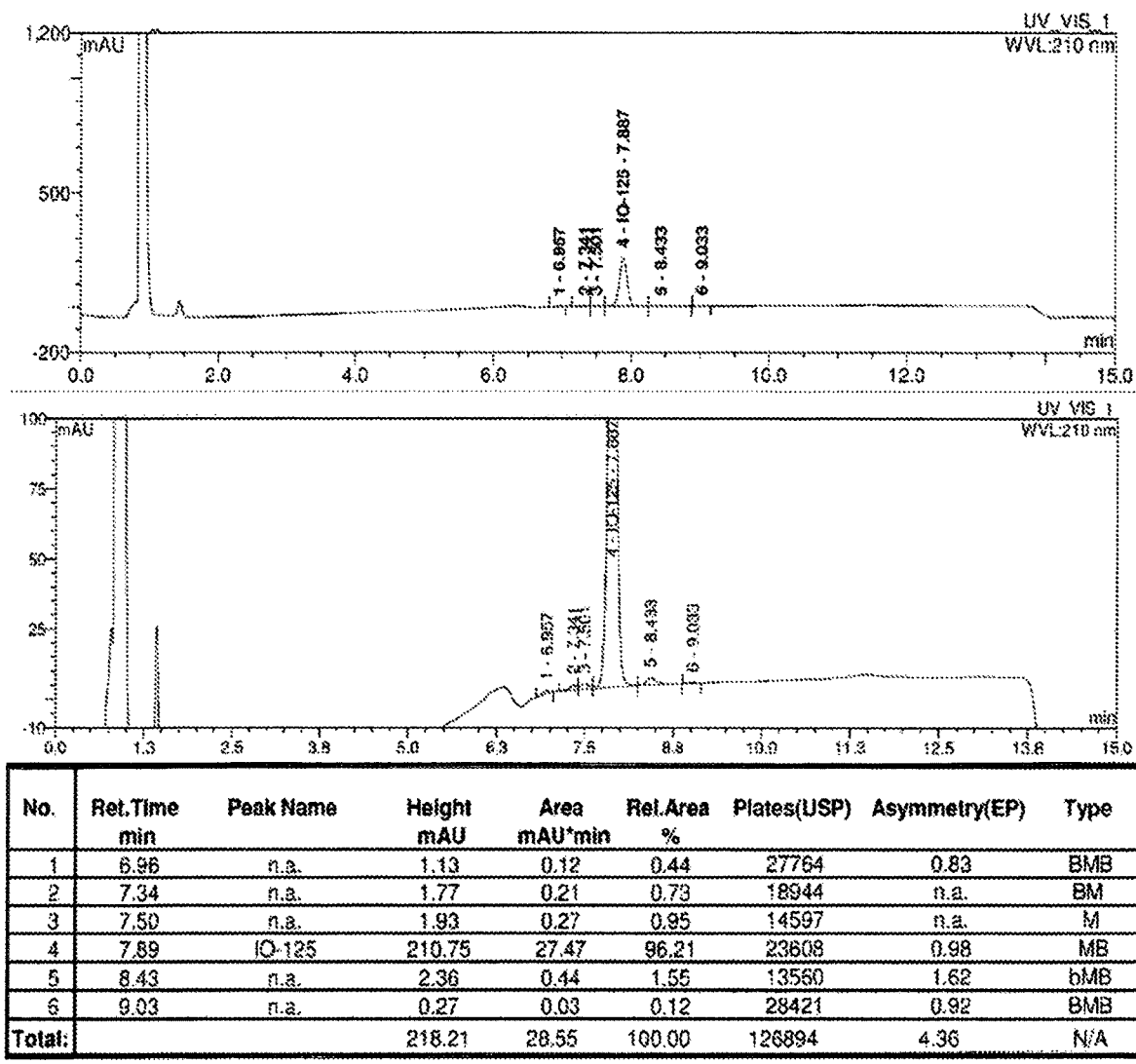
FIG. 27 is a HPLC chromatogram of solids isolated using methanol:dichloromethane (20:80% v/v).

Solvent mixture methanol:dichloromethane (10:90% v/v). Concentration 160 mg/ml. The material returned was crystalline and had a purity of 96.65% by HPLC. The calculated yield for this experiment was 36%. Solvent mixture methanol:dichloromethane (20:80% v/v). Concentration 190 mg/ml. The material returned was crystalline and had a purity of 96.21% by HPLC (FIG. 27). The calculated yield for this experiment was 41%.

TABLE 21

Conditions for seeded cooling crystallization

| Solvent system (% v/v) | Input (mg) | Solvent (mL) | Concentration (mg/mL) |
|---|---|---|---|
| Methanol:Dichloromethane (20:80) | 254.01 | 1.32 | 190.00 |
| Methanol:Dichloromethane (10:90) | 250.08 | 1.56 | 160.00 |

Seeded, Anti-Solvent and Cooling Crystallization

Figure 28:
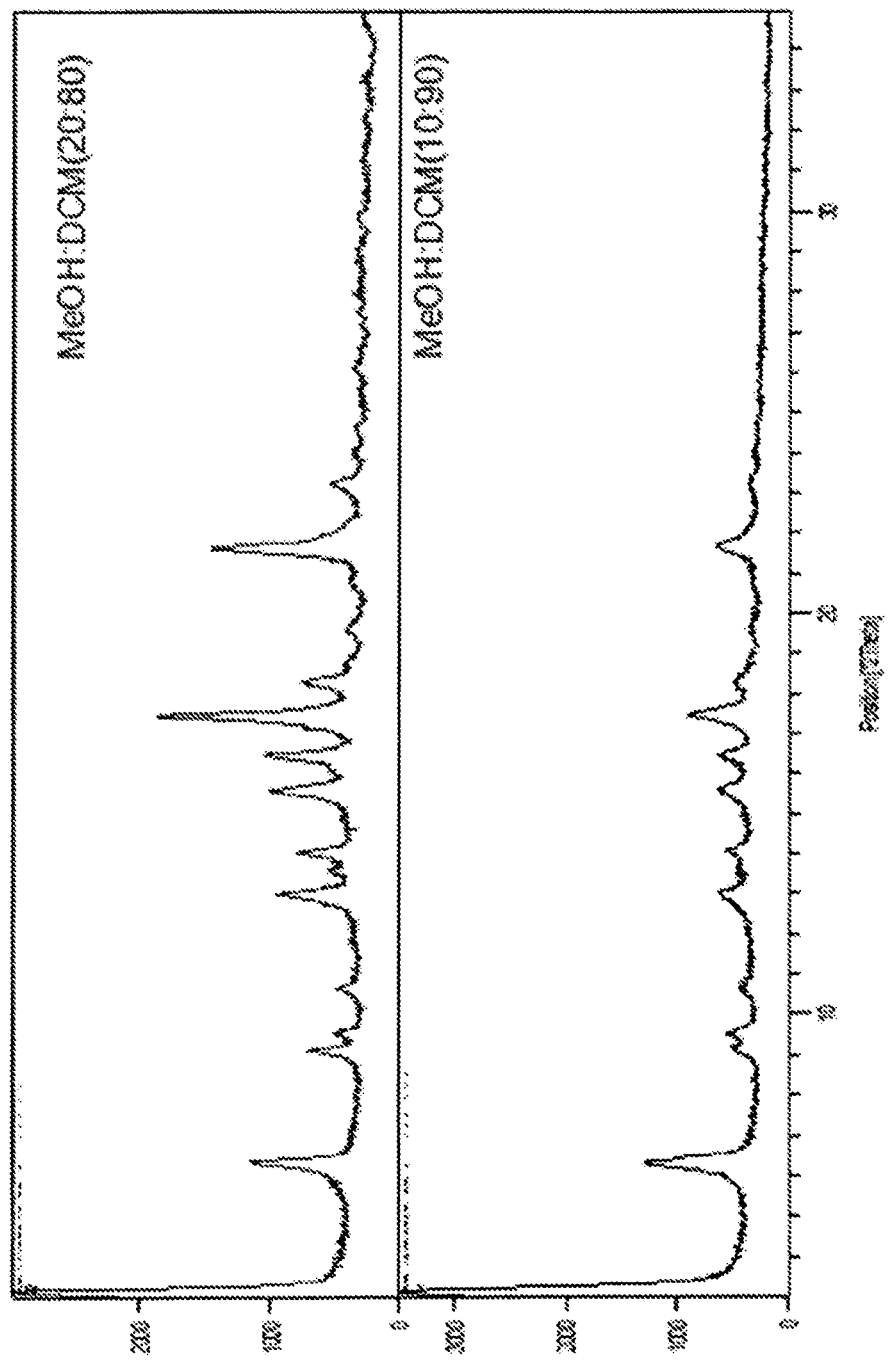
FIG. 28 shows XRPD 2θ diffractograms of dried solids.
Figure 29:
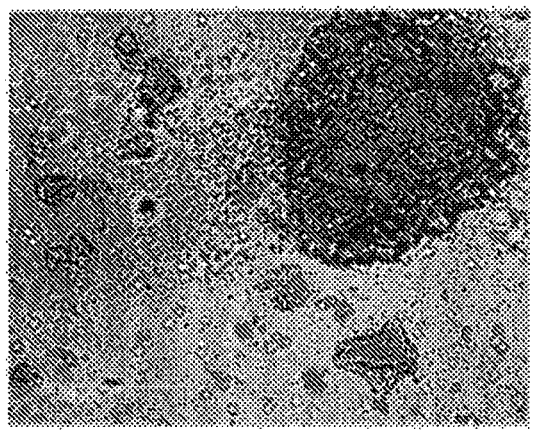
FIG. 29 shows PLM micrographs of dried solids.
Figure 29:
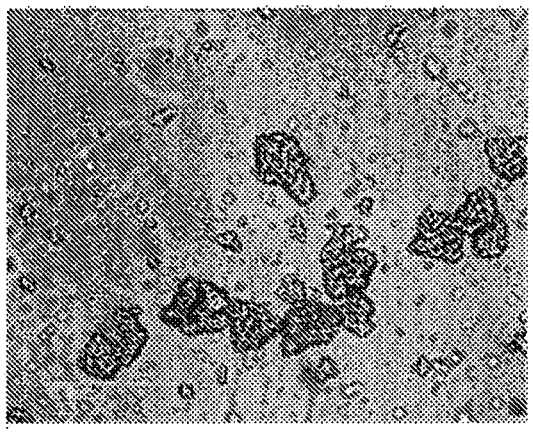
Figure 29:
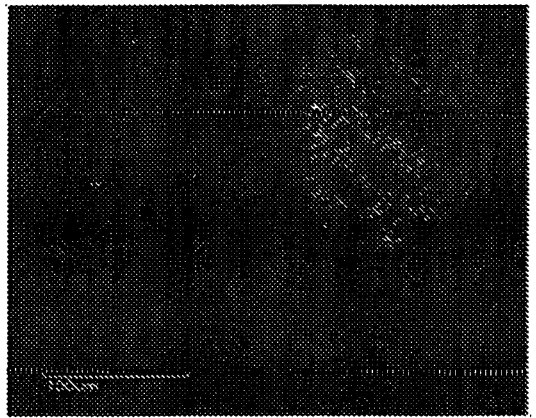
Figure 29:
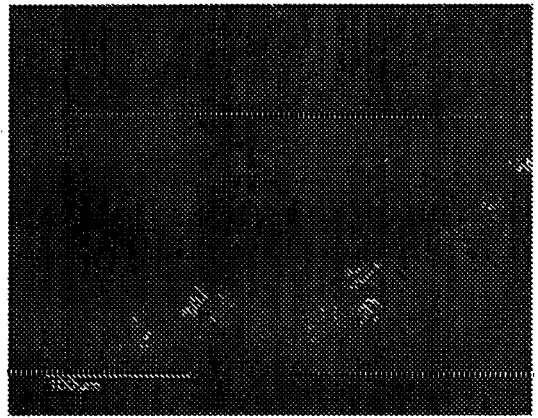
Figure 30:
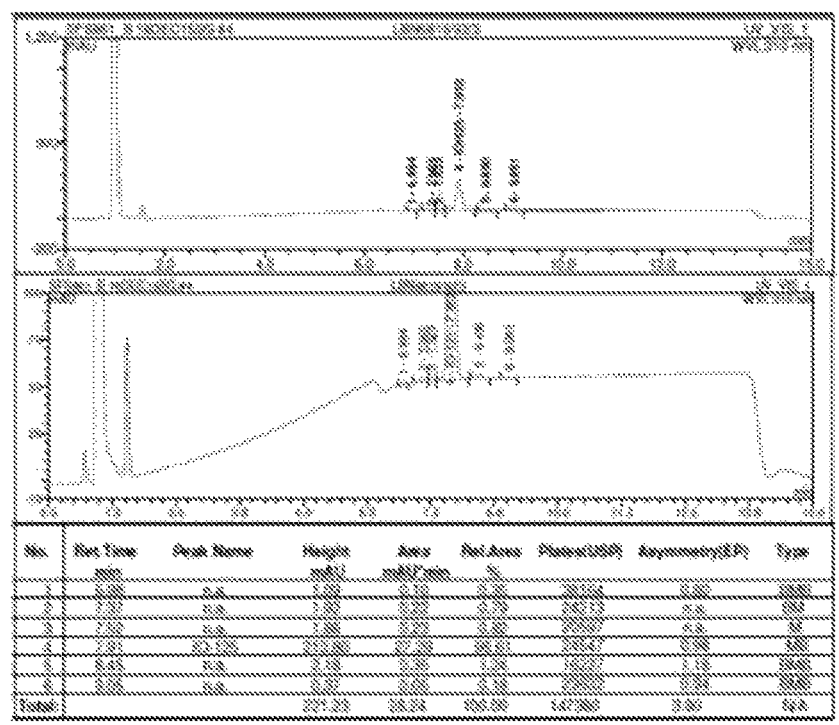
FIG. 30 is a HPLC chromatogram of solids isolated using methanol:dichloromethane (20:80% v/v) with heptanes as anti-solvent.

General Procedure:

Approximately 250 mg Crude COMP 25 was weighed into a 20 mL sample vial and appropriate volume of respective solvent system was added at ca. 250 to dissolve the IO-125. Heptane was added as an and-solvent in 250NL aliquots. Total 1 ml heptane was added to each experiment. The experiments were seeded using crystalline COMP 25. The experiments were stirred at 25° C. for ca. 1 hour and then cooled down to 5° C. at ca. 0.1° C./minute. Stirred at 5° C. for 2 hours. Temperature cycled between 5° C. to 40° C. Heated to 40° C. over 2 hours (ca. 0.3° C./minute). Stirred at 40° C. for 2 hours. Cooled down to 5° C. over 2 hours (ca. 0.3° C./minute). Stirred at 5° C. for 2 hours. The experiments were isolated at ambient (ca. 22° C.) by filtering over Buchner funnel under vacuum using Whatmann filter paper no 1 and then dried under vacuum at ambient temperature overnight (ca. 18 hours). The solid material was then analysed by XRPD (FIG. 28) and PLM (FIG. 29). The combination of all three techniques was used to see if there was any difference in the material produced from solvent systems and also to see if the best crystallisation conditions have been found. Yield calculations were carried out and are summarized in Table 22. HPLC chromatogram of an isolated solid using methanol:dichloromethane (20:80% v/v) with heptanes as anti-solvent is shown in FIG. 30.

TABLE 22

Experimental observation of seeded, anti-solvent and cooling crystallization

| Solvent system (% v/v) | Concentration (mg/mL) | Anti-solvent | Concentration (mg/mL) | XRPD Analysis | Yield | HPLC purity |
|---|---|---|---|---|---|---|
| Methanol:Dichloromethane (20:80) | 333 | Heptane | 142.96 | Crystalline | 48% | 96.61% |
| Methanol:Dichloromethane (10:90) | 333 | Heptane | 142.86 | Crystalline | 51% | 96.35% |

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

We claim:

1. A method for preparing a cholesterol-conjugated platinum compound, the method comprising:
   a. reacting a cholesterol or a cholesterol derivative with a linker that is:

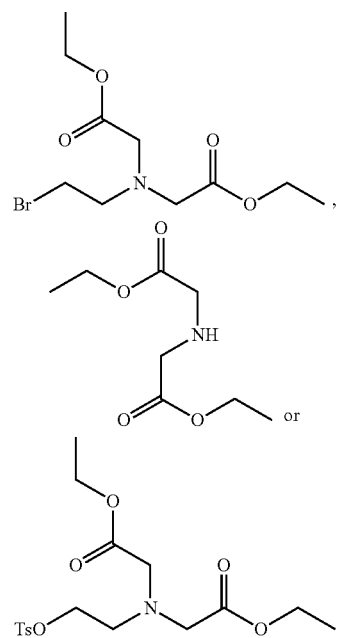

to obtain,

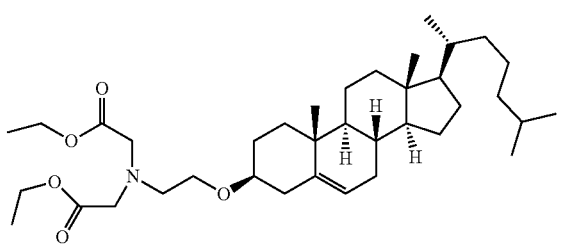

b. reacting the product obtained in step a) with a base that is LiOH, NaOH, KOH, RbOH, CsOH, Mg(OH)$_2$, Ca(OH)$_2$, Sr(OH)$_2$, Ba(OH)$_2$, an acid or any combination thereof to obtain a water-soluble salt of a cholesterol; and
   c. reacting the water-soluble salt of the cholesterol with a water-soluble platinum compound in a substantially aqueous solution to obtain the cholesterol-conjugated platinum compound as a precipitate;
   wherein the method provides a yield of >50% purity of >70% for the cholesterol-conjugated platinum compound.

2. The method of claim 1, further comprising the step of:
   filtering or centrifuging to separate the precipitate from the substantially aqueous solution, and optionally washing the precipitate with water.

3. The method of claim 1, further comprising the step of:
purifying the cholesterol-conjugated platinum compound using HPLC.

4. The method of claim 1, wherein the purity of the cholesterol-conjugated platinum compound is determined using analytical HPLC on a $NH_2$, C18 or phenyl column.

5. The method of claim 3, wherein the HPLC purification uses a preparative reverse-phase column.

6. The method of claim 5, wherein the column comprises an $NH_2$ stationary phase, a phenyl stationary phase, or a C18 stationary phase.

7. The method of claim 4, wherein the column comprises $NH_2$ or phenyl stationary phase, and the cholesterol-conjugated platinum compound is eluted using a gradient method.

8. The method of claim 7, wherein the gradient method comprises eluting with a mobile phase comprising a mixture of water and methanol, wherein elution begins with the mixture having a higher percentage of water and linearly progresses over time to the mixture having a higher percentage of methanol.

9. The method of claim 4, wherein the column comprises C18, and the cholesterol-conjugated platinum compound is eluted using an isocratic method.

10. The method of claim 9, wherein the isocratic method comprises eluting with a mobile phase comprising 98% methanol and 2% water.

11. The method of claim 3, wherein the HPLC purification step provides a purity of >99.5% for the cholesterol-conjugated platinum compound.

12. The method of claim 1, wherein the method provides a yield of >70% for the cholesterol-conjugated platinum compound.

13. The method of claim 1, wherein the substantially aqueous solution comprises at least 90% water.

14. The method of claim 1, wherein the substantially aqueous solution is water.

15. The method of claim 1, wherein the step c) is performed at room temperature and at about one atmosphere of pressure.

16. The method of claim 1, wherein the water-soluble salt of the cholesterol is a lithium salt, a sodium salt, a potassium salt, a rubidium salt, a cesium salt, a magnesium salt, a calcium salt, a strontium salt, a barium salt, a trifluoroacetic acid (TFA) salt, or any combination thereof.

17. The method of claim 1, wherein the water-soluble platinum compound is of Formula V:

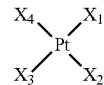

wherein:
$X_1$, $X_2$, $X_3$ and $X_4$ are independently halide, alkyl, amino, alkylamino, dialkylamino, hydroxyl, $H_2O$, alkoxy, thiol, thioalkyl, or O-acyl.

18. The method of claim 1, wherein the water-soluble platinum compound is of Formula V:

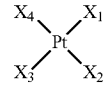

wherein, $X_1$ and $X_2$ are monodentate ligands or bidentate ligands and $X_3$ and $X_4$ are independently halide, alkyl, amino, alkylamino, dialkylamino, hydroxyl, $H_2O$, alkoxy, thiol, thioalkyl, or O-acyl.

19. The method of claim 17, wherein $X_1$ and $X_2$ are amino.

20. The method of claim 18, wherein $X_1$ and $X_2$ are diaminocyclohexyl (DACH).

21. The method of claim 17, wherein $X_3$ and $X_4$ are each $H_2O$.

22. The method of claim 18, wherein the water-soluble platinum compound is prepared by
reacting a platinum compound of Formula V, wherein $X_1$ and $X_2$ comprise a bidentate amino ligand and $X_3$ and $X_4$ each comprise a halide,
with $AgNO_3$ and $H_2O$.

23. The method of claim 22, wherein $X_1$ and $X_2$ are DACH and $X_3$ and $X_4$ are each Cl.

* * * * *